(12) United States Patent
Bhugra et al.

(10) Patent No.: US 11,690,774 B2
(45) Date of Patent: *Jul. 4, 2023

(54) ORTHOSIS SYSTEMS AND REHABILITATION OF IMPAIRED BODY PARTS

(71) Applicant: NeuroLutions, Inc., Santa Cruz, CA (US)

(72) Inventors: Kern Bhugra, Santa Cruz, CA (US); August Anderson, Santa Cruz, CA (US)

(73) Assignee: Neurolutions, Inc., Santa Cruz, CA (US)

(*) Notice: Subject to any disclaimer, the term of this patent is extended or adjusted under 35 U.S.C. 154(b) by 444 days.

This patent is subject to a terminal disclaimer.

(21) Appl. No.: 17/069,433

(22) Filed: Oct. 13, 2020

(65) Prior Publication Data

US 2021/0106490 A1 Apr. 15, 2021

Related U.S. Application Data

(63) Continuation of application No. 17/068,426, filed on Oct. 12, 2020, now Pat. No. 11,534,358.
(Continued)

(51) Int. Cl.
*A61H 1/02* (2006.01)
*A61N 1/36* (2006.01)
(Continued)

(52) U.S. Cl.
CPC ......... *A61H 1/0288* (2013.01); *A61H 1/0285* (2013.01); *A61N 1/36003* (2013.01);
(Continued)

(58) Field of Classification Search
CPC ........ A61H 1/02; A61H 1/0237; A61H 1/024; A61H 1/0244; A61H 1/0255;
(Continued)

(56) References Cited

U.S. PATENT DOCUMENTS 3,631,542 A 1/1972 Potter
3,967,321 A 7/1976 Ryan et al.
(Continued)

FOREIGN PATENT DOCUMENTS

WO WO 2005/074369 8/2005
WO WO 2005/074370 8/2005
(Continued)

OTHER PUBLICATIONS

PCT International Search Report and Written Opinion in International Application No. PCT/US2020/055238, dated Mar. 18, 2021, 16 pages.
(Continued)

*Primary Examiner* — Justine R Yu
*Assistant Examiner* — Christopher E Miller
(74) *Attorney, Agent, or Firm* — Fish & Richardson P.C.

(57) ABSTRACT

A system for moving or assisting in movement of a body part of a subject, as well as a rehabilitation system including such a movement assistance system, includes a body part interface configured to be secured to the body part, and a motor-actuated assembly connected to the body part interface to move the body part interface to cause flexion or extension movement of the body part. A force sensing module is configured to measure forces applied between the body part interface and the motor-actuated assembly to ascertain at least one of volitional flexion and volitional extension movement of the body part by the subject, among other functions that may be implemented in movement assistance and rehabilitation systems using the disclosed force sensing module designs.

22 Claims, 31 Drawing Sheets

Related U.S. Application Data

(60) Provisional application No. 62/914,162, filed on Oct. 11, 2019.

(51) Int. Cl.
*A63B 21/00* (2006.01)
*A63B 23/16* (2006.01)
*G06F 3/01* (2006.01)

(52) U.S. Cl.
CPC ........ *A63B 21/00181* (2013.01); *A63B 23/16* (2013.01); *G06F 3/014* (2013.01); *G06F 3/015* (2013.01); *A61H 2201/10* (2013.01); *A61H 2201/123* (2013.01); *A61H 2201/14* (2013.01); *A61H 2201/165* (2013.01); *A61H 2201/1635* (2013.01); *A61H 2201/1654* (2013.01); *A61H 2201/1664* (2013.01); *A61H 2201/1669* (2013.01); *A61H 2201/1676* (2013.01); *A61H 2201/5012* (2013.01); *A61H 2201/5025* (2013.01); *A61H 2201/5061* (2013.01); *A61H 2201/5097* (2013.01); *A61H 2205/065* (2013.01); *A61H 2205/067* (2013.01); *A61H 2230/105* (2013.01); *A61N 1/36031* (2017.08)

(58) Field of Classification Search
CPC .. A61H 1/0266; A61H 1/0274; A61H 1/0281; A61H 1/0285; A61H 1/0288
See application file for complete search history.

(56) References Cited

U.S. PATENT DOCUMENTS

| | | | |
|---|---|---|---|
| 4,576,148 A | 3/1986 | Koerner et al. |
| 4,875,469 A | 10/1989 | Brook et al. |
| 4,962,756 A | 10/1990 | Shamir et al. |
| 5,067,479 A | 11/1991 | Saringer et al. |
| 5,178,137 A | 1/1993 | Gooer et al. |
| 5,327,882 A | 7/1994 | Saringer et al. |
| 5,458,560 A | 10/1995 | Kaiser et al. |
| 5,466,213 A | 11/1995 | Hogan et al. |
| 5,516,249 A | 5/1996 | Brimhall |
| 5,638,826 A | 6/1997 | Wolpaw et al. |
| 5,683,351 A | 11/1997 | Kaiser et al. |
| 5,697,892 A | 12/1997 | Torgerson |
| 5,738,636 A | 4/1998 | Saringer et al. |
| 5,765,228 A | 6/1998 | Bieling |
| 6,042,555 A | 3/2000 | Kramer et al. |
| 6,613,000 B1 | 9/2003 | Reinkensmeyer et al. |
| 7,058,445 B2 | 6/2006 | Kemere et al. |
| 7,090,650 B2 | 8/2006 | Ou et al. |
| 7,120,486 B2 | 10/2006 | Leuthardt et al. |
| 7,826,894 B2 | 11/2010 | Masallam et al. |
| 8,058,823 B2 | 11/2011 | Horst et al. |
| 8,165,685 B1 | 4/2012 | Knutson et al. |
| 8,177,732 B2 | 5/2012 | Einav et al. |
| 8,214,029 B2 | 7/2012 | Koeneman et al. |
| 8,274,244 B2 | 9/2012 | Horst et al. |
| 8,353,854 B2 | 1/2013 | Horst et al. |
| 8,532,756 B2 | 9/2013 | Schalk et al. |
| 8,679,043 B2 | 3/2014 | Bonutti |
| 8,938,289 B2 | 1/2015 | Einav et al. |
| 9,198,793 B2 | 12/2015 | Bonutti |
| 9,278,012 B2 | 3/2016 | Gill |
| 9,333,107 B2 | 5/2016 | Potter et al. |
| 9,375,382 B2 | 6/2016 | Fausti et al. |
| 9,387,112 B2 | 7/2016 | Bryant |
| 9,402,749 B2 | 8/2016 | Gill et al. |
| 9,532,916 B2 | 1/2017 | Tsui et al. |
| 9,539,118 B2 | 1/2017 | Leuthardt et al. |
| 9,730,816 B2 | 8/2017 | Leuthardt et al. |
| 10,028,880 B2 | 7/2018 | Arata et al. |
| 10,271,967 B2 | 4/2019 | Arakawa |
| 10,307,319 B2 | 6/2019 | Bonuti et al. |
| 10,350,105 B2 | 7/2019 | Eriksson |
| 10,405,764 B2 | 9/2019 | Leuthardt et al. |
| 10,449,677 B1 | 10/2019 | Al Najjar et al. |
| 10,817,056 B2 | 10/2020 | Gu |
| 11,534,358 B2 | 12/2022 | Kern et al. |
| 2002/0065580 A1 | 5/2002 | Derakhshan |
| 2003/0073939 A1 | 4/2003 | Taylor et al. |
| 2005/0131311 A1 | 6/2005 | Leuthardt et al. |
| 2006/0167371 A1 | 7/2006 | Flaherty et al. |
| 2006/0173259 A1 | 8/2006 | Flaherty et al. |
| 2006/0293617 A1 | 12/2006 | Einav et al. |
| 2007/0282228 A1 | 12/2007 | Einav et al. |
| 2008/0070752 A1 | 3/2008 | Einav |
| 2008/0288020 A1 | 11/2008 | Einav et al. |
| 2009/0099627 A1 | 4/2009 | Molnar et al. |
| 2009/0221928 A1 | 9/2009 | Einav et al. |
| 2009/0306531 A1 | 12/2009 | Leuthardt et al. |
| 2009/0306548 A1 | 12/2009 | Bhugra et al. |
| 2009/0312817 A1 | 12/2009 | Hogle et al. |
| 2010/0094154 A1 | 4/2010 | Schalk et al. |
| 2010/0121232 A1 | 5/2010 | Sankai |
| 2010/0152628 A1 | 6/2010 | Kaiser |
| 2010/0204620 A1 | 8/2010 | Smith et al. |
| 2010/0305717 A1 | 12/2010 | Tong et al. |
| 2011/0009788 A1 | 1/2011 | Kelly et al. |
| 2011/0021959 A1 | 1/2011 | Brown |
| 2011/0282253 A1 | 11/2011 | Menon et al. |
| 2011/0295338 A1 | 12/2011 | Rickert et al. |
| 2011/0307079 A1 | 12/2011 | Oweiss et al. |
| 2012/0025945 A1 | 2/2012 | Yazadi et al. |
| 2012/0029399 A1 | 2/2012 | Sankai |
| 2012/0052905 A1 | 3/2012 | Lim et al. |
| 2012/0059290 A1 | 3/2012 | Yip |
| 2012/0157263 A1 | 6/2012 | Sivak et al. |
| 2012/0165158 A1 | 6/2012 | Ren et al. |
| 2012/0245713 A1 | 9/2012 | Chen et al. |
| 2013/0072829 A1 | 3/2013 | Fausti et al. |
| 2013/0096453 A1 | 4/2013 | Chung et al. |
| 2013/0219585 A1 | 8/2013 | Bergelin et al. |
| 2013/0226350 A1 | 8/2013 | Bergelin et al. |
| 2013/0278500 A1 | 10/2013 | Kawasaki et al. |
| 2013/0338556 A1 | 12/2013 | Hoffman et al. |
| 2014/0142483 A1 | 5/2014 | Jackson |
| 2014/0200432 A1 | 7/2014 | Banetji et al. |
| 2014/0277582 A1 | 9/2014 | Leuthardt et al. |
| 2014/0330394 A1 | 11/2014 | Leuthardt et al. |
| 2015/0148728 A1 | 5/2015 | Sallum et al. |
| 2015/0164731 A1 | 6/2015 | Kwak et al. |
| 2015/0245972 A1 | 9/2015 | Arakawa |
| 2015/0342818 A1 | 12/2015 | Ikebe et al. |
| 2015/0374575 A1 | 12/2015 | Kamper et al. |
| 2016/0015590 A1 | 1/2016 | Arata et al. |
| 2016/0018892 A1 | 1/2016 | Gu |
| 2016/0198971 A1 | 7/2016 | Adachi et al. |
| 2016/0270999 A1 | 9/2016 | Masia |
| 2017/0095391 A1 | 4/2017 | Sapin |
| 2017/0119271 A1 | 5/2017 | Leuthardt et al. |
| 2017/0132947 A1 | 5/2017 | Maeda et al. |
| 2017/0165144 A1 | 6/2017 | Ban |
| 2017/0168565 A1 | 6/2017 | Cohen et al. |
| 2017/0181915 A1 | 6/2017 | Ang et al. |
| 2017/0266075 A1 | 9/2017 | Becchi et al. |
| 2017/0325705 A1 | 11/2017 | Murguialday et al. |
| 2018/0085616 A1 | 3/2018 | Makiyama et al. |
| 2018/0177666 A1 | 6/2018 | Tsui et al. |
| 2018/0296419 A1 | 10/2018 | Tong et al. |
| 2018/0303698 A1 | 10/2018 | Wijesundara et al. |
| 2018/0325766 A1 | 11/2018 | Arzanpour |
| 2019/0038222 A1 | 2/2019 | Krimon et al. |
| 2019/0125612 A1 | 5/2019 | Takai et al. |
| 2019/0152049 A1 | 5/2019 | Luijten |
| 2019/0192371 A1 | 6/2019 | Tsui et al. |
| 2019/0209412 A1 | 7/2019 | Lindemann |
| 2019/0336381 A1 | 11/2019 | Koltzi et al. |
| 2019/0350478 A1 | 11/2019 | Leuthardt et al. |
| 2019/0384391 A1 | 12/2019 | Li |
| 2020/0093677 A1 | 3/2020 | Mak |
| 2020/0113770 A1 | 4/2020 | Yang et al. |

(56) References Cited

U.S. PATENT DOCUMENTS

| | | | |
|---|---|---|---|
| 2020/0163787 A1 | 5/2020 | Goldfarb et al. |
| 2020/0237250 A1 | 7/2020 | Ushiba |
| 2020/0315486 A1 | 10/2020 | Hirata et al. |
| 2020/0329991 A1 | 10/2020 | Ushiba |
| 2020/0345574 A1 | 11/2020 | Sankai |
| 2021/0106488 A1 | 4/2021 | Bhugra et al. |
| 2021/0106489 A1 | 4/2021 | Bhugra et al. |

FOREIGN PATENT DOCUMENTS

| | | |
|---|---|---|
| WO | WO 2005/074373 | 8/2005 |
| WO | WO 2005/075155 | 8/2005 |
| WO | WO 2005/086574 | 9/2005 |
| WO | WO 2005/087307 | 9/2005 |
| WO | WO 2005/105203 | 11/2005 |
| WO | WO 2007/096269 | 8/2007 |
| WO | WO 2011/123072 | 10/2011 |

OTHER PUBLICATIONS

International Preliminary Report on Patentability in International Appln. No. PCT/US2020/055238, dated Apr. 21, 2022, 11 pages.
[No Author Listed] [online], "L300 Plus System (Right, Left), L300 Plus System Upgrade Kit (Right, Left)," Apr. 2011, retrieved on Jan. 31, 2012, retrieved from URL <http://www.accessdata.fda.gov/SCRIPTs/cdrh/devicesatfda/index.cfm?db=pmn&id=K103>, 1 page.
[No Author Listed] "Ness H2000® Wireless," 2011, Bioness Inc., product brochure, 3 pages.
[No Author Listed], "Cigna Medical Coverage Policy," Cigna, Aug. 15, 2011, 41 pages.
[No Author Listed], CyberGrasp, CyberGlove Systems Brochure, 2009, 1 page.
[No Author Listed], Hand of Hope Brochure, 6 pages.
[No Author Listed], JAS GL Finger Brochure, 3 pages.
[No Author Listed], Kurzweil accelerating intelligence stories on progress: A thought-controlled robotic exoskeleton for the hand, Sep. 26, 2016, 2 pages.
[No Author Listed], Passive Mobilization Brochure, 7 pages.
aac-rerc.psu.edu [online], "IpsiHand: Direct recoupling of intention and movement," RESNA Student Design Competition, Apr. 27, 2011, retrieved on Jun. 17, retrieved from URL http://aac-rerc.psu.edu/wordpressmu/RESNA-SDC/2011/04/27/ipsihand-direct-recoupling-of-intention-and-movement-washington-university-in-st-louis/>, 8 pages.
accessdata.fda.gov [online] "MAUDE Adverse Event Report: Bioness Bioness Bioness H200 4.5 AMPS," Jan. 21, 2011, retrieved on Jan. 31, 2012, retrieved URL <http://www.accessdata.fda.gov/scripts/cdrh/cfdocs/cfmaude/detail.cfm?mdrfoi_id=2023489>, 1 page.
accessdata.fda.gov [online], "Encephalogram Telemetry System," 1998, retrieved on Jan. 31, 2012, retrieved from URL <http://www.accessdata.fda.gov/scripts/cdrh/cfdocs/cfPCD/classification.cfm?ID=3230>, 1 page.
accessdata.fda.gov [online], "Mentor Hand Therapy Device," 1998, retrieved on Jan. 31, 2012, retrieved from URL <http://www.accessdata.fda.gov/scripts/cdrh/cfdocs/cfRL/LDetails.cfm?LID=81677>, 3 pages.
accessdata.fda.gov [online], "mPower 1000 EMG Sensor," retrieved on Jan. 31, 2012, retrieved from URL <http://www.accessdata.fda.gov/scripts/cfdrh/cfdocs/cfRL/LDetails.cfm?LID=226356>, 2 pages.
accessdata.fda.gov [online], "mPower 1000, Orthosis, Limb Brace," retrieved on Jan. 31, 2012, retrieved from URL <http://www.accessdata.fda.gov/scripts/cfdrh/cfdocs/cfRL/LDetails.cfm?LID=220937>, 1 page.
accessdata.fda.gov [online], "Saeboflex; Saebostetch orthosis, limb brace," retrieved on Jan. 14, 2012, retrieved from URL <http://www.accessdata.fda.gov/scripts/cdrh/cfdocs/cfRL/LDetails.cfm?LID=99358>, 2 pages.
Aggogeri, "Robotics for rehabilitation of hand movement in stroke survivors," Advances in Mechanical Engineering, Apr. 2019, 11(4):1-32.
Arnold et al., "Combination Neuromuscular Electrical Stimulator, Interferential Stimulator, and Transcutaneous Electrical Nerve Stimulator, Model NexWare, 510(k) No. K111279," [letter, indications for use], Sep. 2011, 3 pages.
Barry et al., "Effects of the saeboFlex® orthosis and a home exercise program on upper extremity recovery in individuals with chronic," Journal of Neurologic Physical Therapy, Dec. 2006, 30(4):207.
blue.regence.com [online], "Regence Medical Policy: Durable medical equipment section—functional neuromuscular electrical stimulation," Jul. 2000, retrieved on Jan. 31, 2012, retrieved from URL ,http://blue.regence.com/trgmedpol/dme/dme56.html>, 8 pages.
Broetz et al., "Combination of brain computer interface training and goal-directed physical therapy in chronic stroke: A case report," Neurorehabilitation and Neural Repair, Sep. 2010, 24(7):674-679.
Buch et al., "Think to move: a neuromagnetic brain-computer interface (BCI) system for chronic stroke," Stroke, Mar. 2008, 39(3):910-917.
Cervera et al., "Brain-computer interfaces for post-stroke motor rehabilitation: a meta-analysis," Annals of clinical and translational neurology, May 2018, 5(5):651-663.
clinicaltrials.gov [online], "Bilateral versus unilateral task retraining using the SaeboFlex orthosis," May 6, 2009, retrieved on Jan. 14, 2012, retrieved from URL: <http://clinicaltrials.gov/ct2/show/NCT00893776>, 4 pages.
Daly and Wolpaw, "Brain-computer interfaces in neurological rehabilitation," The Lancet Neurology, Nov. 2008, 7(11):1032-1043.
Devine et al., "OmniPro™ System, 510(k) No. K050143," [summary, letter, indications for use] dated Feb. 1, 2005, 7 pages.
Dorenfeld, "Design of a powered hand orthosis," Project report submitted to the faculty of the Worcester Polytechnic Institute, 2013, 102 pages.
EP Office Action in European Appln. No. 14767543.3, dated Mar. 9, 2017, 11 pages.
EP Office Action in European Appln. No. 14767543.3, dated Nov. 7, 2016, 6 pages.
Fok et al., "An EEG-based brain computer interface for rehabilitation and restoration of hand control following stroke using ipsilateral cortical physiology," Poster, Presented at Annual International Conference of the IEEE Engineering in Medicine and Biology Society, Washington University in St. Louis, Sep. 2011, 1 page.
Holmes et al., "IpsiHand Bravo: an improved EEG-based brain-computer interface for hand motor control rehabilitation," Annual International Conference of the IEEE Engineering in Medicine and Biology Society, Dec. 14, 2012, pp. 1749-1752.
Jones et al., "Design and development of the cable actuated finger exoskeleton for hand rehabilitation following stroke," IEEE/ASME Transactions on Mechatronics, Nov. 2012, 19(1):131-140.
Jones et al., "Impairment and Recovery of Ipsilateral Sensory-Motor Function Following Unilateral Cerebral Infarction," Brain, Feb. 1989, 112(1):113-132.
Lambercy et al., "Robot-assisted rehabilitation of forearm and hand function after stroke," Doctoral dissertation, 2009, 164 pages.
Lehneis and Wilson, "An electric arm orthosis," Bulletin of prosthetics research, 1969, 17 pages.
Leuthardt et al., "The emerging world of motor neuroprosthetics: a neurosurgical perspective," Neurosurgery, Jul. 2006, 59(1):1-14.
Mehring et al., "Comparing information about arm movement direction in single channels of local and epicortical field potentials from monkey and human motor cortex," Journal of Physiology, Jul. 2004, 98(4-6):498-506.
Meng et al., "Design and control of a robotic wrist orthosis for rehabilitation," IEEE International Conference on Advanced Intelligent Mechatronics, Jul. 7, 2015, pp. 1235-1240.
Meng et al., "BCI-FES training system design and implementation for rehabilitation of stroke patients," IEEE, International Joint Conference on Neural Networks, Jun. 1, 2008, pp. 4103-4106.
PCT International Preliminary Report on Patentability and Written Opinion in International Appln. No. PCT/US2008/065953, dated Dec. 7, 2009, 6 pages.
PCT International Search Report in International Appln. No. PCT/US2008/065953, dated Oct. 1, 2008, 1 page.

(56) References Cited

OTHER PUBLICATIONS

Porro et al., "Ipsilateral involvement of primary motor cortex during motor imagery," European Journal of Neuroscience, Aug. 12, 2000, 12(8):3059-3063.

Portnova, "Design of a 3D-printed, open-source wrist-driven orthosis for individuals with spinal cord injury," PloS one, Feb. 2018, 13(2):1-23.

Prasad et al., "Using motor imagery based brain-computer interface for post-stroke rehabilitation," Proceedings of the 4th International IEEE/EMBS Conference on Neural Engineering, Apr. 29, 2009, pp. 258, 262.

Saebo Arm Training Program, SaeboReach®, SaeboFlex® , SaeboStretch® , SaeboGlide®, product brochure, 2008, 8 pages.

Schalk et al., "BCI2000: a general-purpose brain-computer interface (BCI) system," IEEE Transactions on Biomedical Engineering, May 24, 2004, 51(6):1034-1043.

Shoustal et al., "NESS L300 Plus system 510(k) No. K103343," [summary, letter, indications for use] dated Apr. 29, 2011, 8 pages.

Silveira et al., "From the past to the future of therapeutic orthoses for upper limbs rehabilitation," Research on Biomedical Engineering, Oct. 2018, 34(4):368-380.

Soekadar et al., "Brain-machine interfaces in neurorehabilitation of stroke," Neurobiology of disease, Nov. 2015, 83:172-179.

Stein et al., "Biomove 3000 System, 510(k) No. K042650," [summary, letter, indications for use] dated Jan. 27, 2005, 6 pages.

Stein et al., "Biomove 5000 System, 510(k) No. K080787," [summary, letter, indications for use] dated Apr. 17, 2008, 6 pages.

Tsai et al., "Usability assessment of a cable-driven exoskeletal robot for hand rehabilitation," Frontiers in neurorobotics, Feb. 2019; 13:1-21.

Verma et al., "BIS EEG VISTA Monitor System, 510(k) No. K072286," [summary, letter, indications for use] dated Nov. 20, 2007, 8 pages.

Wang et al., "A feasibility study of non-invasive motor-imagery BCI-based robotic rehabilitation for stroke patients," Proceedings of the 4th International IEEE/EMBS Conference on Neural Engineering, Apr. 29, 2009, pp. 271-274.

Wisneski et al., "Unique cortical physiology associated with ipsilateral hand movements and neuroprosthetic implications," Stroke, Dec. 2008, 39(12):3351-3359.

Zebrose et al., "Myomo e100, 510(k) No. K062631," [summary, letter, indications for use] dated Apr. 12, 2007, 7 pages.

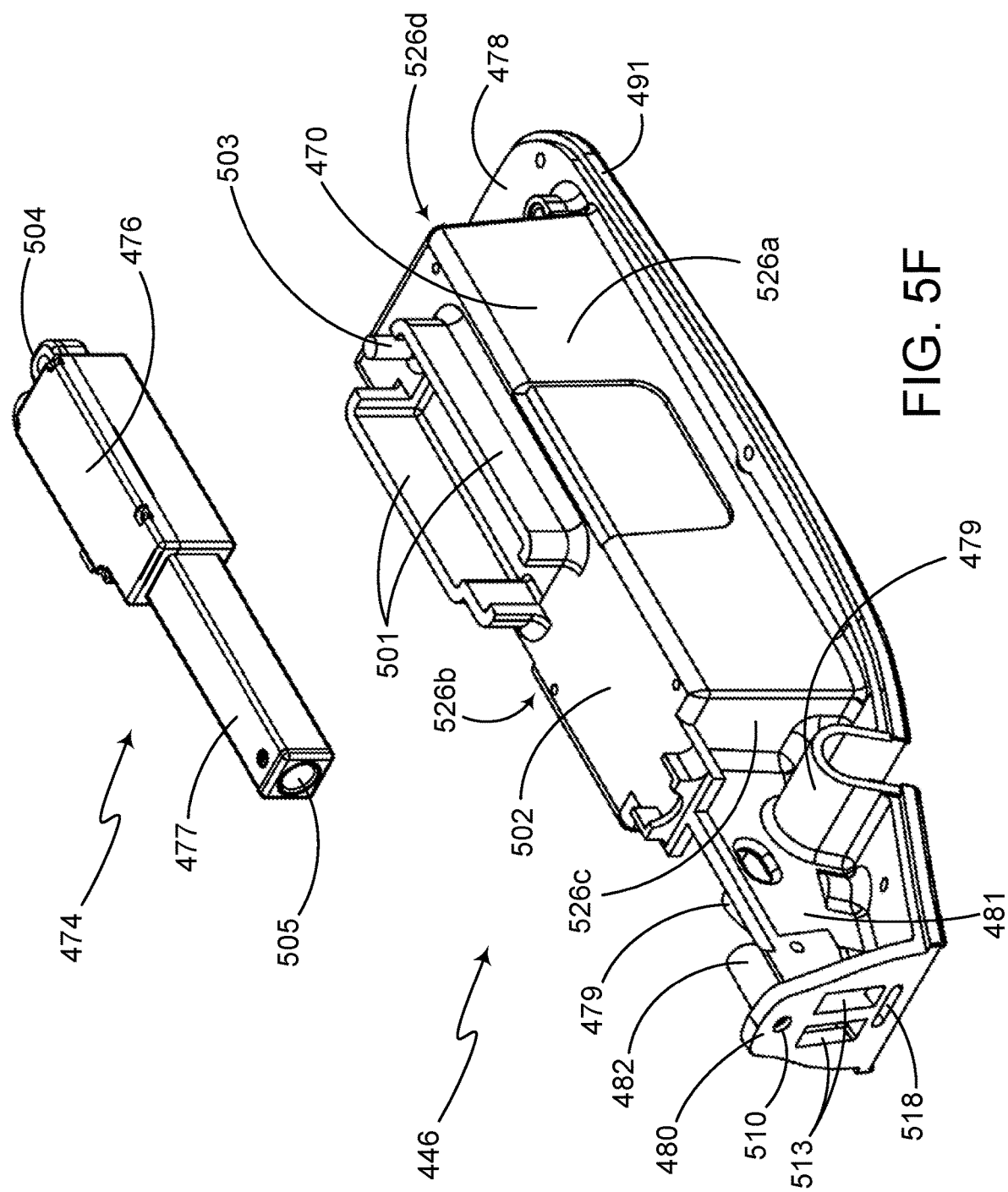

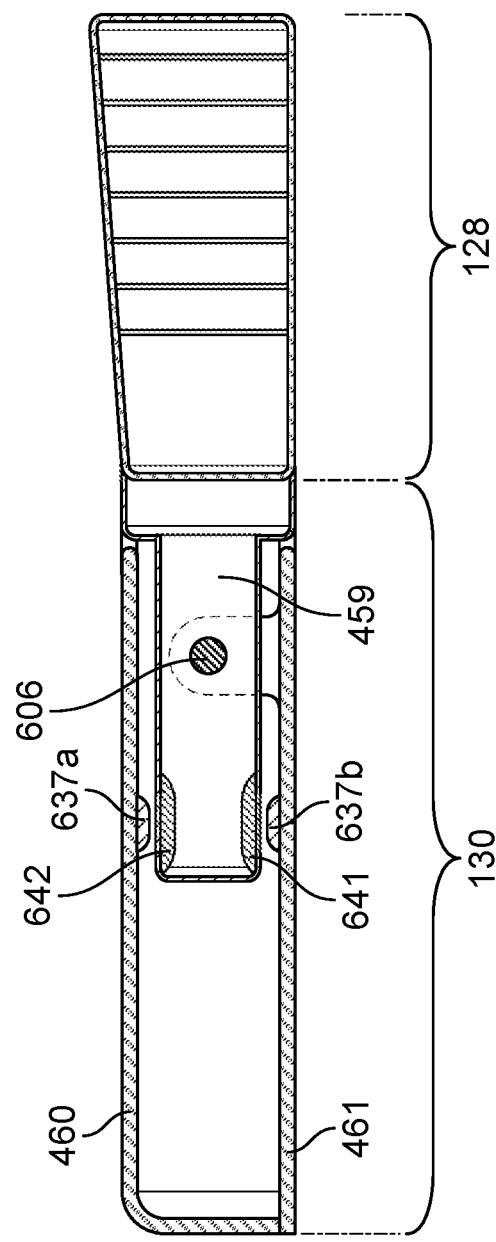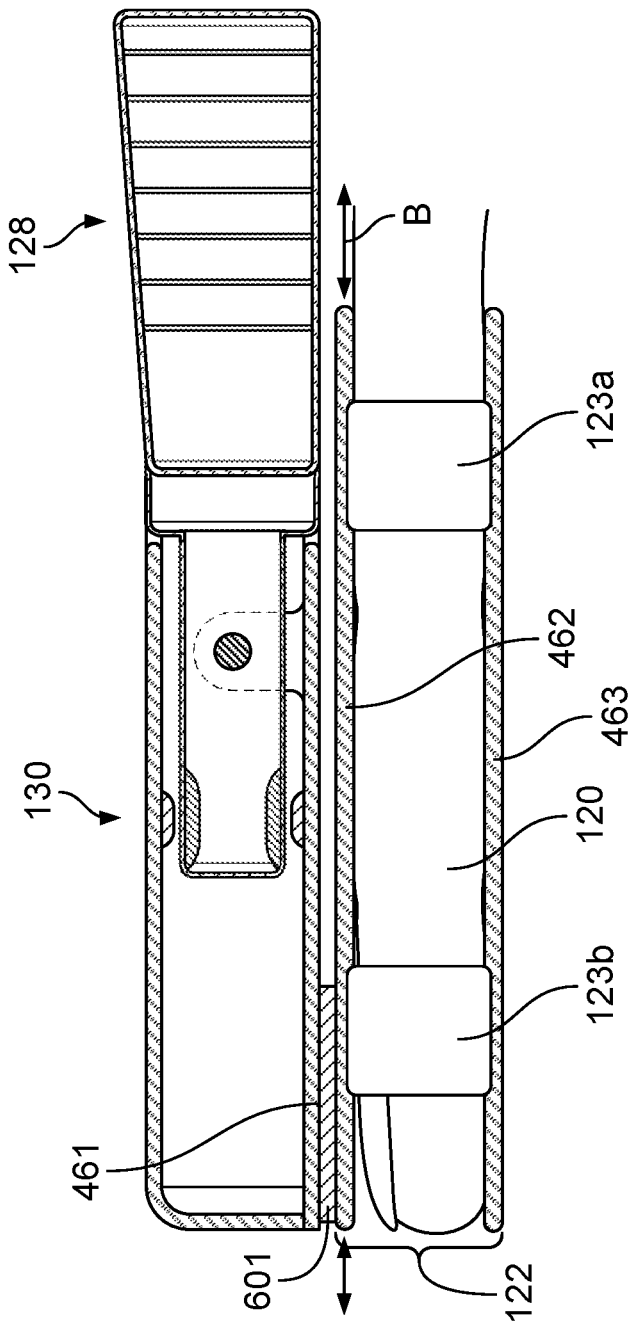

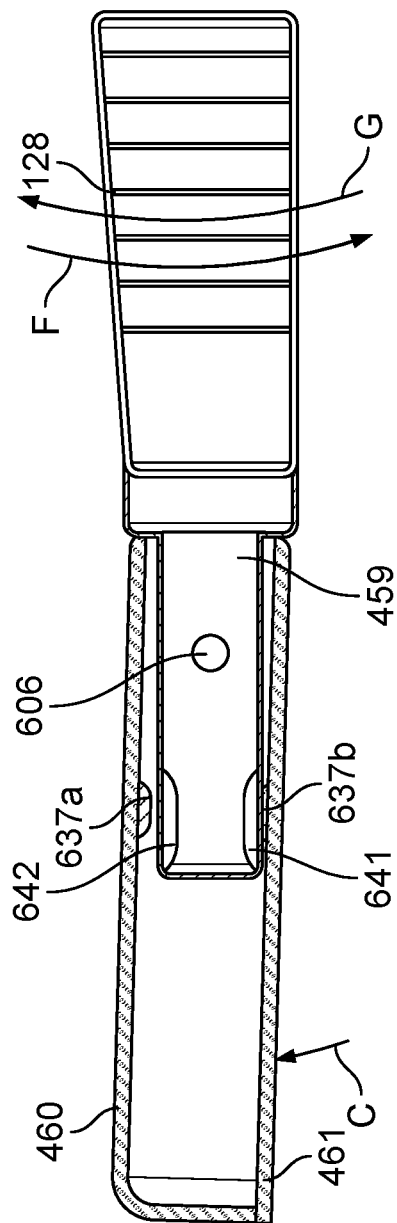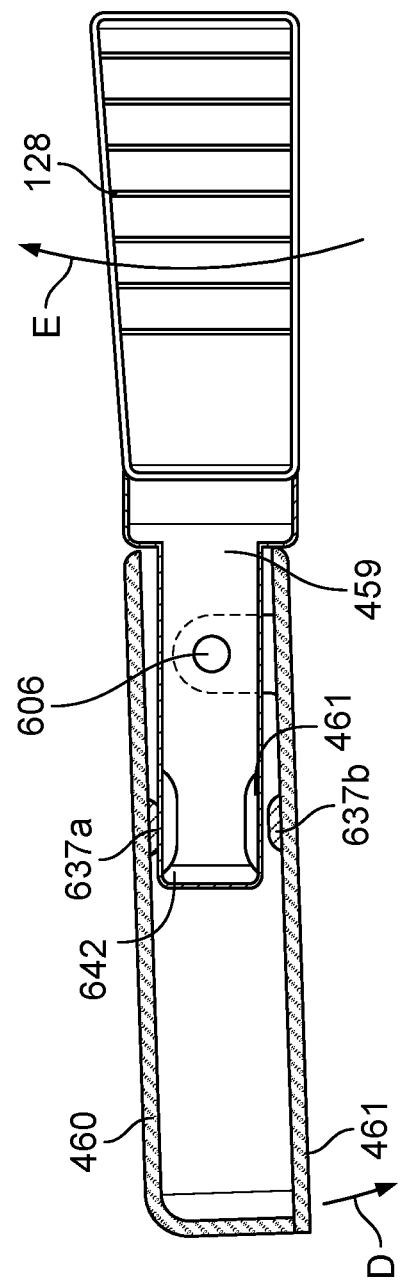

ORTHOSIS SYSTEMS AND REHABILITATION OF IMPAIRED BODY PARTS

CROSS-REFERENCE TO RELATED APPLICATIONS

This is a continuation application of U.S. application Ser. No. 17/068,426, filed on Oct. 12, 2020, which claims the benefit of U.S. Provisional Application Ser. No. 62/914,162, filed on Oct. 11, 2019. The contents of the aforementioned applications are hereby fully incorporated herein by reference.

TECHNICAL FIELD

This specification relates to orthosis systems and to the rehabilitation of impaired limbs, for example, the rehabilitation of an upper limb impaired due to a hemispheric stroke event.

BACKGROUND

Orthosis device designs exist that operate to move or assist in the movement of a subject's body part, for example, upper or lower extremities of a human body. Some orthosis device designs are designed for use in rehabilitating an impaired body part, such as impairment caused by a stroke event.

Brain-computer interface (BCI) technology involves the acquisition and interpretation of brain signals to determine intentions of the person that produced the brain signals and using the determined intentions to carry out intended tasks. BCI technology has been explored in connection with the rehabilitation of impaired body parts, for example, rehabilitation of upper extremity body parts such as arm and hand function impaired due to a stroke event.

Examples of BCI-based systems for use with impaired body parts include descriptions in U.S. Pat. No. 9,730,816 to Leuthardt et al. ('816 patent), under license to the assignee of the present patent application, the content of which is incorporated by reference herein. The '816 patent describes the use of BCI techniques to assist a hemiparetic subject, or in other words, a subject who has suffered a unilateral stroke brain insult and thus has an injury in, or mainly in, one hemisphere of the brain. For that patient, the other hemisphere of the brain may be normal. The '816 patent describes an idea of ipsilateral control, in which brain signals from one side of the brain are adapted to be used, through a BCI training process, to control body functions on the same side of the body. Additional examples of BCI-based systems for use with impaired body parts include descriptions in U.S. Pat. No. 9,539,118 to Leuthardt et al. ('118 patent), commonly assigned with the present patent application, the content of which is incorporated herein by reference. The '118 patent describes wearable orthosis device designs that operate to move or assist in the movement of impaired body parts, impaired due to a stroke event, for example, among other conditions described in the '118 patent. For example, the '118 patent describes rehabilitation approaches for impaired fingers, among other body parts including upper as well as lower extremities, using wearable orthosis devices that operate to move or assist in the movement of the impaired body part and that are controlled using BCI techniques. The '118 patent further elaborates BCI-based rehabilitation techniques that utilize brain plasticity to "rewire" the brain to achieve motor control of impaired body parts.

Orthoses have used various mechanisms to accomplish the movement and/or assistance in the movement of impaired body parts. One such mechanism is to physically attach or secure an active movable portion of the orthosis device to the body part that is to be moved or with which movement is to be assisted. The active movable portion of the orthosis device secured to the body part may then be activated to move by a motor or some other form of actuation, and as such accomplish or assist in the movement of the impaired body part secured thereto. Another such mechanism to accomplish or assist in the movement of a body part is through a technique called functional electrical stimulation ("FES"), which involves the application of mild electrical stimuli to muscles that help the muscles move or move better.

Rehabilitation of an impaired body part may also involve the application of continuous passive motion ("CPM") to the impaired body part, wherein the body part is moved with no volition on the part of the subject. In many cases, a therapist may manually apply CPM to a patient, in essence "working" the body part to rehabilitate it. Additionally, various machines exist that are designed to apply CPM to body parts for rehabilitating that body part.

Despite the existence of various orthosis device designs and rehabilitation systems and techniques utilizing various orthosis device designs, there is much room for improvement to achieve improved rehabilitation outcomes.

SUMMARY

This specification describes systems, devices, and methods for the movement and/or rehabilitation of body parts, for example, the rehabilitation of an upper limb impaired due to a hemispheric stroke event.

In one aspect, a system is provided for use in rehabilitating an impaired body part of a subject. The rehabilitation system includes a brain signal acquisition system configured to collect brain signals from the subject, an orthosis system configured to attach to the impaired body part and to move or assist in movement of the impaired body part; and a control system configured to operate the orthosis system in (a) a first mode in which the orthosis system operates to move or assist in the movement of the impaired body part based on an intention of the subject determined from an analysis of the brain signals, and (b) a second mode in which the orthosis system operates to move the impaired body part.

In various implementations the rehabilitation system may include one or more of the following. The orthosis system, when operating under the second mode, may operate to move the impaired body in a plurality of repetitions of an exercise. The second mode may be a continuous passive mode of operation.

The control system may be further configured to operate the orthosis system in (c) a third mode in which the orthosis system first allows the subject to move or attempt to move the impaired body part in a predefined motion and then operates to move or assist in the predefined motion of the impaired body part. The orthosis system, when operating in the third mode, may operate to move or assist in the predefined motion of the impaired body part in response to the control system detecting that the impaired body part has not completed the predefined motion, operates to move or assist in the predefined motion of the impaired body part. In this case, the control system may be configured to detect that the impaired body part has not completed the predefined motion by determining whether the predefined motion has occurred within a predetermined period of time, and/or the control system may be configured to detect that the impaired body part has not completed the predefined motion by determining whether the predefined motion has occurred to a predefined degree. The predefined degree may correspond to a predefined amount of extension of the impaired body part. For the third mode of operation, the control system may be configured to send a cue to indicate to a subject to begin to move or attempt to move the impaired body part in the predefined motion. In addition, the control system may be configured to detect that the impaired body part has not completed the predefined motion by determining whether the predefined motion has commenced within a predetermined period of time.

The rehabilitation system may be used in a case wherein the impaired body part is impaired due to a stroke event experienced by the subject. The orthosis device may be configured to be worn on a hand of the subject and to operate to move or assist in the movement of the hand. The orthosis device may be configured to operate to move or assist in the movement of the impaired body part using motor-driven actuation. The orthosis device may be configured to operate to move or assist in the movement of the impaired body part using functional electrical stimulation.

In a second aspect, a rehabilitation system is provided for use in rehabilitating an impaired body part of a subject, which includes an orthosis system configured to attach to the impaired body part and to move or assist in movement of the impaired body part, and a control system configured to operate the orthosis system in a volitional movement mode in which the orthosis system first allows the subject to move volitionally or attempt to move volitionally the impaired body part in a predefined motion and then operates to move or assist in the predefined motion of the impaired body part.

In various implementations the rehabilitation system of this second aspect may include one or more of the following. The orthosis system may operate to move or assist in the predefined motion of the impaired body part in response to the control system detecting that the impaired body part has not completed the predefined motion. The control system may be configured to detect that the impaired body part has not completed the predefined motion by determining whether the predefined motion has occurred within a predetermined period of time. The control system may be configured to detect that the impaired body part has not completed the predefined motion by determining whether the predefined motion has occurred to a predefined degree, which may correspond to a predefined amount of extension of the impaired body part. The control system may be configured to send a cue to indicate to a subject to begin to move or attempt to move the impaired body part in the predefined motion. The control system may be configured to detect that the impaired body part has not completed the predefined motion by determining whether the predefined motion has commenced within a predetermined period of time. In addition, the rehabilitation system may further include a brain signal acquisition system configured to collect brain signals from the subject, and in this case, the control system may be further configured to operate in a mode in which the orthosis system operates to move or assist in the movement of the impaired body part based on an intention of the subject determined from an analysis of the brain signals.

The rehabilitation system may be used in a case wherein the impaired body part is impaired due to a stroke event experienced by the subject. The orthosis device may be configured to be worn on a hand of the subject and to operate to move or assist in the movement of the hand. The orthosis device may be configured to operate to move or assist in the movement of the impaired body part using motor-driven actuation. The orthosis device may be configured to operate to move or assist in the movement of the impaired body part using functional electrical stimulation.

In a third aspect, a rehabilitation system is provided for use in rehabilitating an impaired body part of a subject. In this case, the rehabilitation system includes a brain signal acquisition system configured to collect brain signals from the subject, an orthosis system configured to attach to the impaired body part and to move or assist in movement of the impaired body part, and a control system configured to operate the orthosis system in (a) a first mode in which the orthosis system operates to move or assist in the movement of the impaired body part based on an intention of the subject determined from an analysis of the brain signals, (b) a second mode in which the orthosis system operates in a continuous passive mode of operation comprising a plurality of repetitions of an exercise to move the impaired body part, and (c) a third mode in which the orthosis system first allows the subject to move volitionally or attempt to move volitionally the impaired body part in a predefined motion and then operates to move or assist in the predefined motion of the impaired body part.

In various implementations the rehabilitation system of this third aspect may include one or more of the following. The impaired body part may be impaired due to a stroke event experienced by the subject. The orthosis device may be configured to be worn on a hand of the subject and to operate to move or assist in the movement of the hand. In addition, the orthosis device may be configured to operate to move or assist in the movement of the impaired body part using motor-driven actuation. Additional features and details described above in connection with the first and second aspects of the rehabilitation may also be provided in connection with this third aspect of a rehabilitation system.

In a fourth aspect, an orthosis device is provided for a subject. The orthosis device includes a main housing assembly configured to be worn on an upper extremity of the subject and comprising a motor mechanism configured to actuate movement of a body part of the upper extremity of the subject, a body part interface assembly configured to be secured to the portion of the upper extremity and induce, as actuated by the motor mechanism, flexion and extension motion of the secured body part, and a flexible intermediate member interposed between the main housing assembly and the body part interface assembly, wherein the flexible intermediate member is configured to flex or extend responsive to actuation by the motor mechanism to cause the body part interface assembly to flex or extend the secured body part.

In various implementations the orthosis device of this fourth aspect may include one or more of the following. The main housing assembly may be configured to be worn on a forearm of the upper extremity of the subject, the body part may be at least one finger of the upper extremity of the subject, and the body part interface assembly may be a finger and/or thumb interface assembly configured to be secured to the at least one finger and/or thumb of the upper extremity of the subject in a manner that enables extension and flexion movement of the secured at least one finger and/or thumb about a joint associated with the finger and/or thumb. Alternatively, the main housing assembly may be configured to be worn, entirely or in part, on a hand of the upper extremity of the subject, the body part in this case may be at least one digit (at least one finger and/or thumb) of the upper extremity of the subject, and the body part interface assembly may be a finger and/or thumb interface assembly configured to be secured to the at least one finger and/or thumb of the upper extremity of the subject in a manner that enables extension and flexion movement of the secured at least one finger and/or thumb about a joint associated with the finger and/or thumb. Further yet, the main housing assembly may be configured to be worn on a forearm of the upper extremity of the subject, the body part may be a hand of the upper extremity of the subject, and the body part interface assembly may be configured to be secured to the hand of the upper extremity of the subject in a manner that enables extension and flexion movement of the hand about the wrist and relative to the forearm.

Additionally, the orthosis device may be configured such that, when worn, the flexible intermediate member spans the knuckles of the subject. In this case, the orthosis device is further configured such that, when worn, the flexible intermediate member maintains a spaced relationship above the knuckles of the subject during flexion and extension of the flexible intermediate member. The flexible intermediate member may include a plurality of baffle members, with each of the baffle members oriented generally perpendicular to an axis along a length of the forearm of the subject when the orthosis device is worn by the subject. The orthosis device may also include a pushing-and-pulling wire extending longitudinally through each of the baffle members and connected between the motor mechanism of the main housing assembly and the body part interface assembly. Each of the baffle members may have an opening through which the pushing-and-pulling wire extends, with each opening aligned with openings of the other baffle members. The motor mechanism may be configured to push or pull the pushing-and-pulling wire to cause the baffle members to extend or compress with respect to each other to cause the body part interface assembly to rotate downwards or upwards. The motor mechanism comprises a linear actuator.

Further yet, the orthosis device may be configured such that the motor mechanism pushing the pushing-and-pulling wire may cause an upper portion of the baffle members of the flexible intermediate member to extend away from each other and the body part interface assembly to rotate downward. The orthosis device may be configured such that the motor mechanism pulling the pushing-and-pulling wire causes an upper portion of the baffle members of the flexible intermediate member to compress towards each other and the body part interface assembly to rotate upward. The flexible intermediate member may include a flat bottom structure attached to a bottom surface of each of the baffle members such that an opposite top surface of each of the baffle members are free to compress or expand with respect to each other. In this case, the flat bottom surface structure may maintain a spacing between each of the plurality of baffle members at a bottom portion of the baffle members even as an upper portion of the baffle members are being extended and compressed by operation of the pushing-and-pulling wire.

In a fifth aspect, a rehabilitation system for a subject is provided, in which the rehabilitation system includes a brain signal acquisition device configured to collect brain signals from the subject and an orthosis device. The orthosis device includes a main housing assembly configured to be worn on an upper extremity of the subject and comprising a motor mechanism configured to actuate movement of a body part of the upper extremity of the subject in response to the brain signals, a body part interface assembly configured to be secured to the portion of the upper extremity and induce, as actuated by the motor mechanism, flexion and extension motion of the secured body part, and a flexible intermediate member interposed between the main housing assembly and the body part interface assembly, wherein the flexible intermediate member is configured to flex or extend responsive to actuation by the motor mechanism to cause the body part interface assembly to flex or extend the secured body part.

In various implementations the rehabilitation system of this fifth aspect may include one or more of the following. In terms of the orthosis system of the rehabilitation system, the main housing assembly may be configured to be worn on a forearm of the upper extremity of the subject, the body part may be at least one finger of the upper extremity of the subject, and the body part interface assembly may be a finger and/or thumb interface assembly configured to be secured to the at least one finger and/or thumb of the upper extremity of the subject in a manner that enables extension and flexion movement of the secured at least one finger and/or thumb about a joint associated with the finger and/or thumb. Alternatively, the main housing assembly may be configured to be worn, entirely or in part, on a hand of the upper extremity of the subject, the body part in this case may be at least one digit (at least one finger and/or thumb) of the upper extremity of the subject, and the body part interface assembly may be a finger and/or thumb interface assembly configured to be secured to the at least one finger and/or thumb of the upper extremity of the subject in a manner that enables extension and flexion movement of the secured at least one finger and/or thumb about a joint associated with the finger and/or thumb. Further yet, the main housing assembly may be configured to be worn on a forearm of the upper extremity of the subject, the body part may be a hand of the upper extremity of the subject, and the body part interface assembly may be configured to be secured to the hand of the upper extremity of the subject in a manner that enables extension and flexion movement of the hand about the wrist and relative to the forearm.

Additionally, the orthosis device of the rehabilitation system may be configured such that, when worn, the flexible intermediate member spans the knuckles of the subject. In this case, the orthosis device is further configured such that, when worn, the flexible intermediate member maintains a spaced relationship above the knuckles of the subject during flexion and extension of the flexible intermediate member. The flexible intermediate member may include a plurality of baffle members, with each of the baffle members oriented generally perpendicular to an axis along a length of the forearm of the subject when the orthosis device is worn by the subject. The orthosis device may also include a pushing-and-pulling wire extending longitudinally through each of the baffle members and connected between the motor mechanism of the main housing assembly and the body part interface assembly. Each of the baffle members may have an opening through which the pushing-and-pulling wire extends, with each opening aligned with openings of the other baffle members. The motor mechanism may be configured to push or pull the pushing-and-pulling wire to cause the baffle members to extend or compress with respect to each other to cause the body part interface assembly to rotate downwards or upwards. The motor mechanism comprises a linear actuator.

Further yet, the orthosis device of the rehabilitation system may be configured such that the motor mechanism pushing the pushing-and-pulling wire may cause an upper portion of the baffle members of the flexible intermediate member to extend away from each other and the body part interface assembly to rotate downward. The orthosis device may be configured such that the motor mechanism pulling the pushing-and-pulling wire causes an upper portion of the baffle members of the flexible intermediate member to compress towards each other and the body part interface assembly to rotate upward. The flexible intermediate member may include a flat bottom structure attached to a bottom surface of each of the baffle members such that an opposite top surface of each of the baffle members are free to compress or expand with respect to each other. In this case, the flat bottom surface structure may maintain a spacing between each of the plurality of baffle members at a bottom portion of the baffle members even as an upper portion of the baffle members are being extended and compressed by operation of the pushing-and-pulling wire.

In a sixth aspect, an orthosis device for a subject is provided that includes a main housing assembly configured to be worn on an upper extremity of the subject and comprising a motor mechanism configured to actuate movement of at least one finger of the subject, and a finger interface assembly connected to the main housing assembly and configured to be secured to at least one finger of the subject and to induce, as actuated by the motor mechanism, flexion and extension motion of the at least one secured finger. The orthosis device is also to leave unsecured to the orthosis device at least one finger that is not the at least one finger secured to the finger stay assembly.

In various implementations the orthosis device of this sixth aspect may include one or more of the following. The orthosis device may include a thumb interface assembly configured to maintain a thumb of the subject in an extended position. The finger interface assembly may be configured to be secured to two fingers of the subject, for example, an index finger and a middle finger. The finger interface assembly may be configured to allow free motion of two unsecured fingers of the subject while securing two fingers of the subject. The finger interface assembly, in response to flexion and extension motion of the at least one secured finger, may be configured to slide longitudinally along an axis along a length of the at least one secured finger in relation to a remainder of the orthosis device. In this case, the finger interface assembly may include a sleeve bearing at an upper surface of the finger interface assembly, the sleeve bearing configured to mate with a corresponding sleeve carriage of a separate portion of the orthosis device such that the sleeve bearing slides along the sleeve carriage. The sleeve bearing may include a generally flat rectangular bottom plate and a plurality of rails extending upward from the bottom plate, the rails configured to mate with the sleeve carriage. The finger interface assembly may include a finger stay foam pad configured to contact the at least one secured finger of the subject. The finger interface assembly may have at least one opening configured to receive at least one strap for securing the finger interface assembly to the at least one secured finger.

In a seventh aspect, a rehabilitation system for a subject is provided, which includes a brain signal acquisition device configured to collect brain signals from the subject, and an orthosis device. The orthosis device of this rehabilitation system includes a main housing assembly configured to be worn on an upper extremity of the subject and comprising a motor mechanism configured to actuate movement of a hand of the subject in response to the brain signals; and a finger interface assembly connected to the main housing assembly and configured to be secured to at least one finger of the subject and to induce, as actuated by the motor mechanism, flexion and extension motion of the at least one secured finger. The orthosis device is configured to leave unsecured to the orthosis device at least one finger that is not the at least one finger secured to the finger stay assembly.

In various implementations the rehabilitation system of this seventh aspect may include one or more of the following. In terms of the orthosis system of the rehabilitation system, the orthosis device may include a thumb interface assembly configured to maintain a thumb of the subject in an extended position. The finger interface assembly may be configured to be secured to two fingers of the subject, for example, an index finger and a middle finger. The finger interface assembly may be configured to allow free motion of two unsecured fingers of the subject while securing two fingers of the subject. The finger interface assembly, in response to flexion and extension motion of the at least one secured finger, may be configured to slide longitudinally along an axis along a length of the at least one secured finger in relation to a remainder of the orthosis device. In this case, the finger interface assembly may include a sleeve bearing at an upper surface of the finger interface assembly, the sleeve bearing configured to mate with a corresponding sleeve carriage of a separate portion of the orthosis device such that the sleeve bearing slides along the sleeve carriage. The sleeve bearing may include a generally flat rectangular bottom plate and a plurality of rails extending upward from the bottom plate, the rails configured to mate with the sleeve carriage. The finger interface assembly may include a finger stay foam pad configured to contact the at least one secured finger of the subject. The finger interface assembly may have at least one opening configured to receive at least one strap for securing the finger interface assembly to the at least one secured finger.

In an eighth aspect, a system is provided for moving or assisting in movement of a body part of a subject. The system includes a body part interface configured to be secured to the body part; a motor-actuated assembly connected to the body part interface to move the body part interface to cause flexion or extension movement of the body part; and a force sensing module configured to measure forces applied between the body part interface and the motor-actuated assembly to ascertain at least one of volitional flexion and volitional extension movement of the body part by the subject.

In various implementations the system of this eighth aspect may include one or more of the following. The force sensing module may include a plurality of force sensors, at least one force sensing resistor, and/or at least one load cell force sensor.

The motor-actuated assembly and the body part interface may be pivotally connected such that the motor-actuated assembly and the body part interface are configured to pivot relative to each other such that the body part interface is configured to rotate in a first direction and a second direction opposite to the first direction. In a case with a plurality of force sensors, this may include a first force sensor and a second force sensor, and the motor-actuated assembly may be configured to cause force to be applied to the first force sensor when the motor-actuated assembly rotates the body part interface in the first direction and to cause force to be applied to the second force sensor when the motor-actuated assembly rotates the body part interface in the second direction. One of the motor-actuated assembly or the body part interface assembly may include an extension member having an upper surface and a lower surface opposite the upper surface.

The first force sensor may be located on the upper surface, and the second force sensor may be located on the lower surface of the extension member. The first force sensor on the upper surface may be aligned with a downwardly facing structure provided on one of the motor-actuated assembly or the body part interface assembly that does not have the extension member, wherein the first force sensor may be applied against the downwardly facing structure when the motor-actuated assembly and the body part interface pivot relative to one another in the first direction. The second force sensor on the lower surface may be aligned with an upwardly facing structure provided on the one of the motor-actuated assembly or the body part interface assembly that does not have the extension member, wherein the second force sensor may be applied against the upwardly facing structure when the motor-actuated assembly and the body part interface rock relative to one another in the second direction.

The system of this eighth aspect may be configured so that the first force sensor is used to detect when the motor-actuated assembly is operating to cause extension motion of the secured body part and the subject is providing little or no contribution to the extension motion, and/or detect when the subject is volitionally causing flexion motion of the secured body part and the motor-actuated assembly is not operating to move or assist in the flexion motion. In addition, the system may be configured so that the second force sensor is used to detect when the motor-actuated assembly is operating to cause flexion motion of the secured body part and the subject is providing little or no contribution to the flexion motion, and/or detect when the subject is volitionally causing extension motion of the secured body part and the motor-actuated assembly is not operating to move or assist in the extension motion.

In addition, the system may be an orthosis device configured to be worn on an upper extremity of the subject, and the body part may be associated with a hand of the subject, for example, a finger, thumb, hand/wrist, elbow, or shoulder of an upper extremity or body parts of the lower extremity.

In a ninth aspect, a rehabilitation system is provided that includes a brain signal acquisition device configured to collect brain signals from the subject; and an orthosis system for moving or assisting in movement of a body part of the subject in response to the brain signals. The orthosis system includes a body part interface configured to be secured to the body part; a motor-actuated assembly connected to the body part interface to move the body part interface to cause flexion or extension movement of the body part; and a force sensing module configured to measure forces applied between the body part interface and the motor-actuated assembly to ascertain volitional flexion and extension movement of the body part by the subject.

In various implementations the rehabilitation system of this ninth aspect may include one or more of the following. In terms of the orthosis system of the rehabilitation system, the force sensing module may include a plurality of force sensors, at least one force sensing resistor, and/or at least one load cell force sensor. The motor-actuated assembly and the body part interface may be pivotally connected such that the motor-actuated assembly and the body part interface are configured to pivot relative to each other such that the body part interface is configured to rotate in a first direction and a second direction opposite to the first direction. In a case with a plurality of force sensors, this may include a first force sensor and a second force sensor, and the motor-actuated assembly may be configured to cause force to be applied to the first force sensor when the motor-actuated assembly rotates the body part interface in the first direction and to cause force to be applied to the second force sensor when the motor-actuated assembly rotates the body part interface in the second direction. One of the motor-actuated assembly or the body part interface assembly may include an extension member having an upper surface and a lower surface opposite the upper surface.

The first force sensor may be located on the upper surface, and the second force sensor may be located on the lower surface of the extension member. The first force sensor on the upper surface may be aligned with a downwardly facing structure provided on one of the motor-actuated assembly or the body part interface assembly that does not have the extension member, wherein the first force sensor may be applied against the downwardly facing structure when the motor-actuated assembly and the body part interface pivot relative to one another in the first direction. The second force sensor on the lower surface may be aligned with an upwardly facing structure provided on the one of the motor-actuated assembly or the body part interface assembly that does not have the extension member, wherein the second force sensor may be applied against the upwardly facing structure when the motor-actuated assembly and the body part interface rock relative to one another in the second direction.

The rehabilitation system of this ninth aspect may be configured so that the first force sensor is used to detect when the motor-actuated assembly is operating to cause extension motion of the secured body part and the subject is providing little or no contribution to the extension motion, and/or detect when the subject is volitionally causing flexion motion of the secured body part and the motor-actuated assembly is not operating to move or assist in the flexion motion. In addition, the system may be configured so that the second force sensor is used to detect when the motor-actuated assembly is operating to cause flexion motion of the secured body part and the subject is providing little or no contribution to the flexion motion, and/or detect when the subject is volitionally causing extension motion of the secured body part and the motor-actuated assembly is not operating to move or assist in the extension motion.

In addition, the rehabilitation system may include an orthosis device that is configured to be worn on an upper extremity of the subject, and the body part may be associated with a hand of the subject, for example, a finger, thumb, hand/wrist, elbow, or shoulder of an upper extremity or body parts of the lower extremity.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 5A-5F are diagrams of the orthosis device also shown in FIGS. 4A-4G, except without the finger stay component for clarity.

FIGS. 6A-6H are diagrams illustrating further detail of the structure and operation of a connecting/force sensing module assembly included in the orthosis device shown in FIGS. 4A-4G and 5A-5F.

Like reference numbers and designations in the various drawings indicate like elements.

DETAILED DESCRIPTION

This specification describes systems, devices, and methods for the improved rehabilitation of impaired limbs, for example, for the improved rehabilitation of an upper limb impaired due to a hemispheric stroke event. While stroke rehabilitation will be described in this specification in detail, the techniques described in this specification have much broader applicability beyond stroke rehabilitation.

Figure 1A:
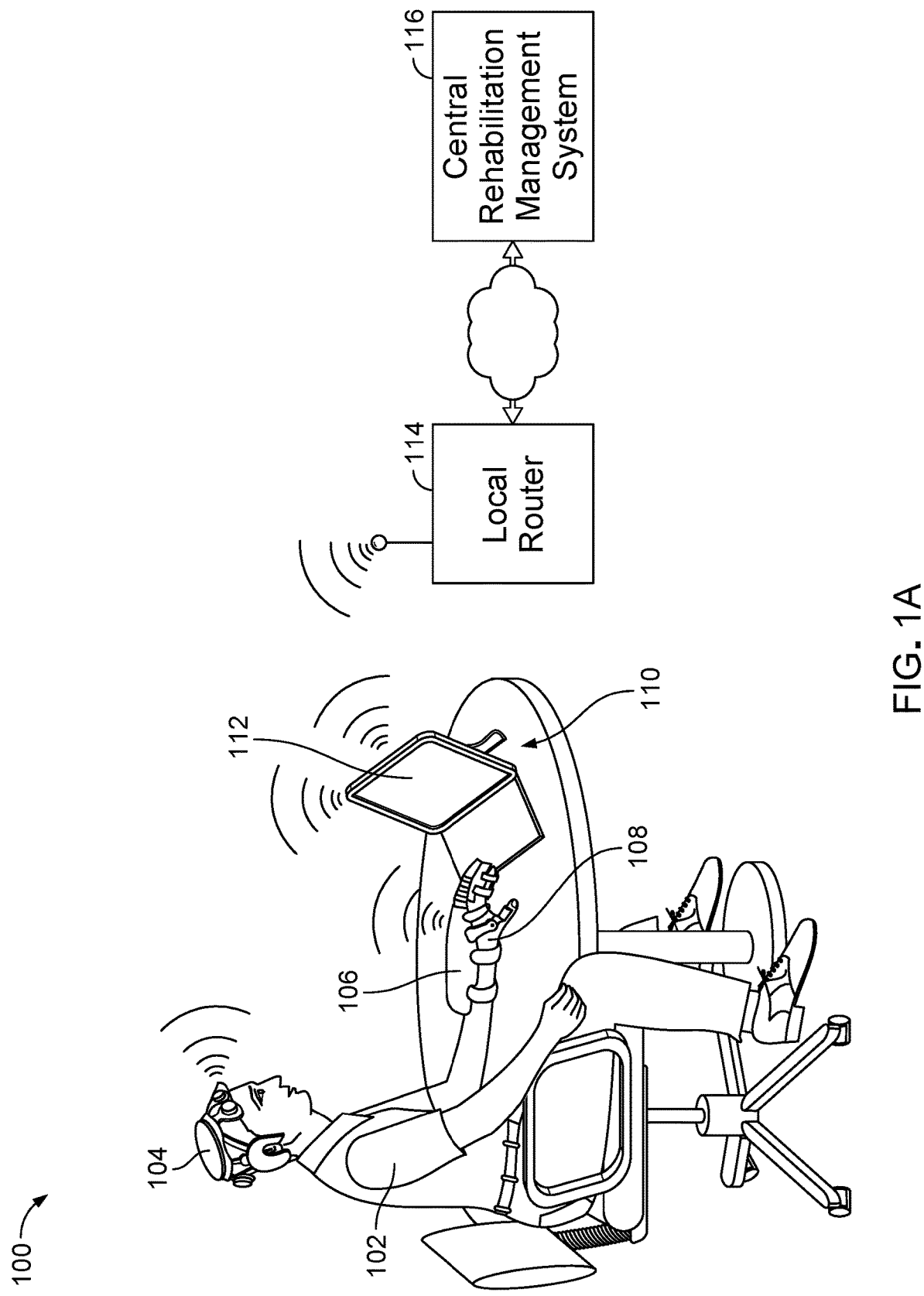
FIG. 1A is a diagram of a rehabilitation system for rehabilitation of an impaired body part, in this example a hand.

One example implementation, shown in FIG. 1A, is a rehabilitation system 100, which is adapted for use by a patient 102 who has for example experienced a brain injury (e.g., stroke, trauma, infection, hemorrhage, neonatal malformation, cerebral palsy, nedegenerative) to rehabilitate the patent's hand having impaired motor control. Generally, the rehabilitation system 100 includes: (i) a brain signal acquisition system 104 which in this example is a headset having several surface electrodes that acquire electroencephalogram (EEG) brain signals from multiple different and distributed surface locations on the patient's skin adjacent the brain, thereby enabling a brain computer interface ("BCI") mode of operation with the rehabilitation device 100; (ii) an orthosis device 106 designed and configured to be fully wearable on the forearm and hand 108 (in this example, the left forearm and hand 108) of the patient and is designed and configured to be secured to an impaired body part (in this case, the hand) and to cause movement or assist in causing movement of the impaired hand; (iii) a local computing system 110 with one or more associated application programs and a user display device 112 to provide instruction, guidance, prompts, and information for set-up, performing rehabilitation sessions, and monitoring progress; (iv) a local network router device 114 to provide network connectivity by local devices and information to remote or external systems; and (v) a network accessible central rehabilitation management computing system 116, which may be used in the set-up and on-going operation and monitoring of the local aspects of the rehabilitation system 100 and may be located remote from where the patient performs rehabilitation activities, for example, at a healthcare facility (e.g., hospital, clinic, etc.) or facilities of some other type such as a rehabilitation services provider.

Figure 1B:
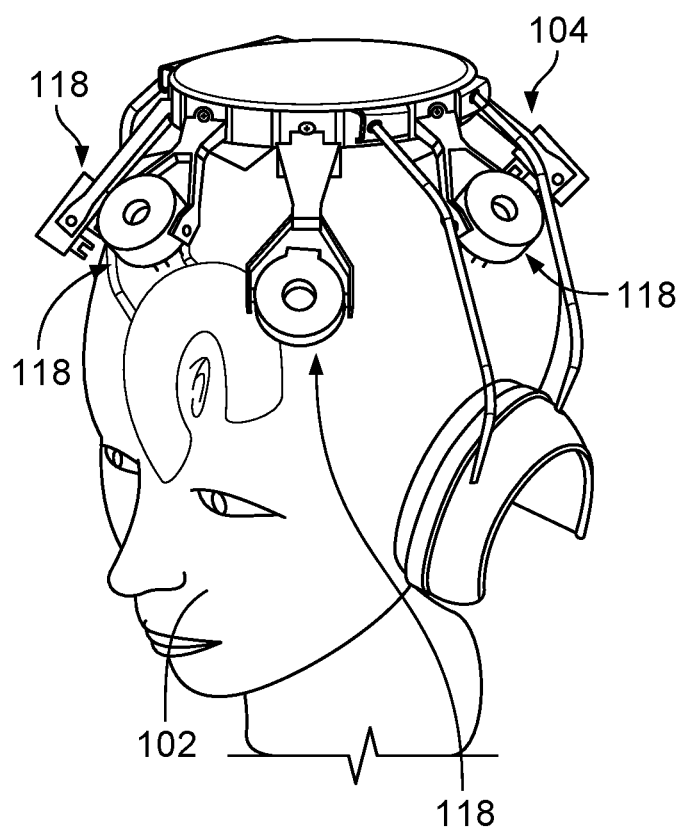
FIG. 1B is a diagram of a brain signal acquisition system used in the system of FIGS. 1A and 1n the form of an electroencephalogram (EEG) headset, shown as worn on a head of the subject.
Figure 1C:
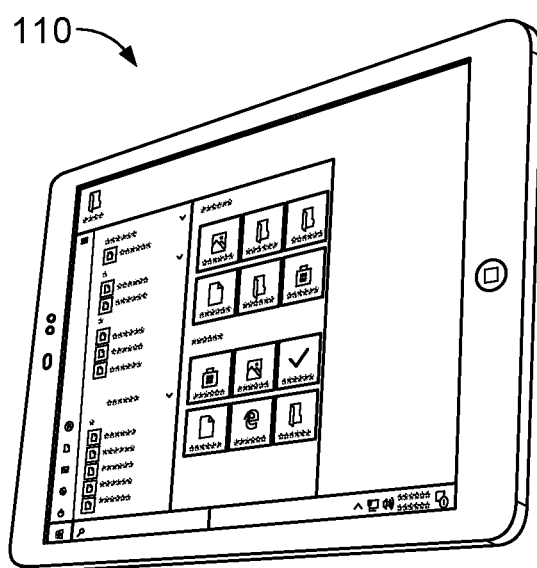
FIG. 1C is a diagram of a local and mobile computing system in the form of a tablet computer used in the system of FIG. 1A.

The brain signal acquisition system 104, shown in FIGS. 1A and 1n more detail in FIG. 1B, may be, as in this example, a commercially available dry electrode EEG headset, model DSI 7, marketed and sold by Wearable Sensing LLC of San Diego, Calif. The brain signal acquisition system 104 acquires brain signals, performs low-level signal processing, and transmits the EEG brain signals (for example, wirelessly) for receipt by either the orthosis device 108 directly, or via the local computing system 112, for further processing by a computer system embedded within the orthosis device 108. Alternatively, acquired EEG brain signals may be transmitted to and further processed by the local computing system 112, and thereafter the local computing system 112 may send control signals to the orthosis device 118 to effect action thereby.

The EEG brain signals may be acquired by the acquisition system 104, as in this example, using a plurality of arranged surface electrodes 118 that are part of the acquisition system 104. Each of the surface electrodes 118 is located at an end of a corresponding arm that extends from a housing of the acquisition system 104 to a distal position such that, when the acquisition system 104 is worn by the patient, the electrodes 118 may be positioned to rest upon the patient's skin adjacent the brain. Although the brain signal acquisition system in the FIGS. 1A and 1B example is a dry EEG electrode system, alternatively a wet EEG electrode system may be utilized, in which case the electrodes 118 may be moistened, through application of a liquid or gel to the electrodes 118, before being applied to the patient's skin, which may increase conductivity with the patient's skin and allow for brain signals to be detected and recorded in some cases with greater accuracy.

The brain signal acquisition system 104, although shown in FIG. 1A only from one side of the patient 102, may include electrodes 118 designed to be positioned on both sides of the patient's head to acquire brain signals from both sides of the brain. That said, in some applications where a patient has suffered a unilateral stroke event wherein one hemisphere of the brain is negatively impacted or damaged but the opposite hemisphere remains effective and/or healthy, it may be that useful brain signal activity is only generated by the unaffected hemisphere of the patient's brain, which may be on the same side of the body as, or ipsilateral to, an adversely affected limb whose motor control has been adversely affected by a stroke event. In such a case, ipsilateral brain signals associated with the patient's motor control intentions for movement of a body part on the same side of the body as the acquired brain signals may be distinct from (in terms of frequency, location, and magnitude of the brain signals) contralateral brain signals associated with the patent's motor control intentions for movement of a body part on the opposite side of the body as the acquired brain signals, as described in U.S. Pat. No. 9,730,816 to Leuthardt et al. ('816 patent), incorporated by reference herein. In some cases, it may be only possible, or in some cases adequate, to acquire "ipsilateral" brain signals from an unaffected hemisphere of the patient's brain located on the same side of the body as the impaired body part. In such a case, the brain signal acquisition system 104 may be designed and adapted to acquire brain signals from only one side of the patient's brain. In other cases, contralateral brain signals (on the opposite side of body as an affected body part) may also be sufficiently present and detectable and therefore may be acquired and utilized in a rehabilitation process, thereby making use of concepts of brain plasticity or rewiring of the brain to make new connections to achieve motor control improvements after a stroke event.

Although an EEG-based brain signal acquisition system 104 with skin surface electrodes is shown in the FIG. 1A example, other brain signal acquisition systems may alternatively be used in connection with the BCI devices, systems and methods described herein. For example, acquisition systems with implantable electrodes may be used. For example, electrocorticography (ECOG) electrodes may be used and implanted under the skull of the patient and positioned so that the electrodes rest upon the brain surface but without penetrating into the brain tissue. Another example electrode system that may alternatively be used is a "point-style" electrode system that is also implanted beneath the skull of the patient, although this type of electrode system has electrode tips that penetrate into the brain tissue. Typically, such "point-style" implanted electrode systems include many prongs designed so that each of the prongs penetrates into the brain tissue at a different location.

Implantable electrodes may be desirable over surface EEG electrodes in that the acquired brain signals may contain greater information content regarding the intentions of the patient. For example, with implantable electrodes, it may be possible to discriminate intentions regarding movement of each and every one of the patient's fingers, whereas that may not be possible, or at least may be more difficult, using brain signals acquired using surface EEG electrodes. That is, because the skull may operate to block or dampen part of the brain signals, particularly at higher frequencies. That said, it will be recognized that implantable electrodes have the potential drawback of requiring a medical procedure to implant the electrodes. Additionally, advances in the processing and analysis of brain signals captured via EEG electrodes including those described herein are making EEG bases systems more useful in BCI-based rehabilitation.

As discussed previously, the wearable orthosis device 106 of FIG. 1A (also shown in more detail in FIG. 1D), may receive transmitted signals (for example, wirelessly) containing information about the brain signals acquired by the acquisition system 104. The orthosis device 106 may then process those received signals to determine patient intentions using embedded processing equipment, and in accordance with certain detected patient intentions cause or assist the movement of the patient's hand and/or fingers by robotic or motor-driven action of the orthosis device 106. As has been described previously, the brain signal information may be received by the orthosis device 106 for processing directly from a brain signal acquisition system 104, or alternatively may be received via the local computing system 110 (which in the latter example may receive the brain signal information from the brain signal acquisition system 104, store the brain signal information locally within local computing system 112 for a record of the same, and retransmit the brain signal information wirelessly and in real-time to the orthosis device 106 for further processing to instigate control functions by the orthosis).

Figure 1D:
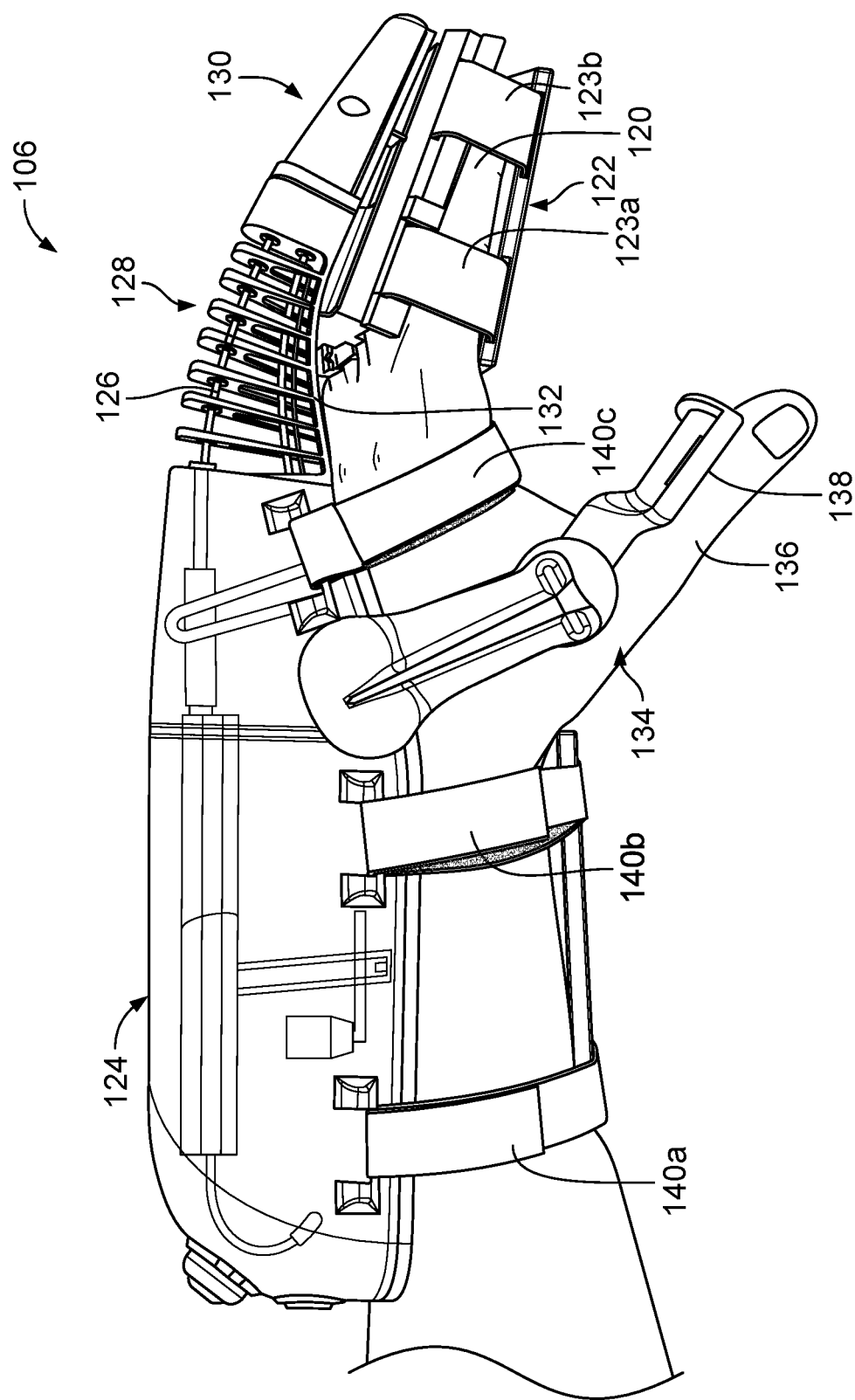
FIG. 1D is a diagram of a wearable orthosis device used in the system of FIG. 1A, shown being worn on a left forearm and hand of the subject.

The wearable orthosis device 106, specifically in the example of FIGS. 1A and 1D, is designed and adapted to assist in the movement of the patient's fingers, specifically the index finger 120 (labeled in FIG. 1D) and the adjacent middle finger (not shown in FIGS. 1A and 1D), both of which are securely attached to the orthosis device 106 by a finger stay component 122. In particular, the specific movement accomplished by the orthosis device 106 of FIGS. 1A and 1D is the extension (opening) and flexion (closing) of the finger stay component 122 which causes the extension (opening) and flexion (closing) of the attached index finger 120 and adjacent middle finger.

The wearable orthosis device 106 also includes a thumb piece 134 that, at a proximal end, is attached to a side of the main housing structure 124 on the side where the subject's thumb would be located, depending on whether the device 106 is being worn on the right arm and hand or the left. In the case FIGS. 1A and 1D, the device 106 is being worn on the left forearm and hand, and the thumb piece 134 accordingly extends from the side of the main housing structure 124 on which the subject's left thumb is located. The thumb piece 134 in the example of FIGS. 1A and 1D extends to a thumb contact portion 138 which in use is put in contact with an inner surface of the thumb 136, in order to maintain the thumb 136 in a generally extended position as shown in FIG. 1D. In this embodiment, the thumb piece 134 is adjustable manually to a position such as that shown in FIG. 1D, and once manually adjusted to that position, remains in that position, or in other words, is not in this embodiment actuated by an actuator such as a motor or the like but instead remains in the same position during use of the orthosis device 106 in a rehabilitation session.

The extension and flexion of the finger stay device 122, and hence the extension and flexion of the index and middle fingers secured thereto, is initiated by a linear motor device (not shown in FIG. 1D, but which will be shown and described later in this specification) that is located inside a main housing structure 124 of the orthosis device 106. The main housing structure 124, as shown in FIG. 1D, is designed and configured to be worn on top of, and against, an upper surface (that is, the dorsal side) of the patient's forearm and hand. The main housing structure 124 is designed such that it extends parallel with the forearm from a proximal end that is located, when worn, generally at a mid-point of the forearm (midway between the wrist and the elbow) to a distal end that is located, when worn, generally just slightly proximal of the patient's knuckles, as best shown in FIG. 1D. The linear motor device inside the main housing structure 124 longitudinally advances and retracts a pushing-and-pulling wire 126 that extends distally from the distal end of the main housing structure 124 and, as will be described below, extends longitudinally through a flexible intermediate structure 128 and connects to a connection point on a force sensing module ("FSM") assembly 130.

The flexible intermediate component 128 having a flexible baffle structure is attached to the distal end of the main housing component 124. As shown in FIG. 1D, the flexible intermediate component 128 is configured such that, when worn properly, it extends from a proximal end that is located generally slightly proximal of, and above, the knuckles to a distal end that is distal of the knuckles and generally above the joints of the index and middle fingers, as best shown in FIG. 1D. The pushing-and-pulling wire 126, which extends distally from the main housing structure 124, extends through the entire length of the flexible intermediate structure 128 and beyond its distal end. In particular, the pushing-and-pulling wire 126 extends longitudinally through a series of aligned openings formed in individual baffle elements that make up the flexible intermediate structure 128. In the example of FIGS. 1A and 1D, there are seven such baffle elements in the flexible intermediate structure 128 through which the pushing-and-pulling wire 126 extends. The pushing-and-pulling wire 126 extends longitudinally from the distal end of the flexible intermediate component 128 to connect to the connection point on the FSM assembly 130.

The connecting and force sensing module ("FSM") assembly 130 is attached to a distal end of the flexible intermediate component 128 and is configured such that it is generally longitudinally extending. The FSM assembly is also referred to as a "connecting" and FSM assembly because it connects (in a slidable manner, as will be described below) the flexible intermediate structure 128 with the finger stay component 122 that is secured to the fingers. As shown in FIG. 1D, the connecting/FSM assembly 130 is configured such that, when worn, it extends longitudinally above the hand (or on the dorsal side of the hand) from a proximal end that is located generally above the joints of the index and middle fingers to a distal end that is located generally beyond, but only slightly beyond, the distal end of the fingers. The finger stay component 122 is attached to an underside of the connecting/force sensing module 130 in a longitudinally slidable manner so that flexion and extension movement of the connecting/FSM assembly 130 translates to flexion and extension movement of the finger stay component 122 (and hence the fingers secured therein), yet the finger stay component 122 is free to slide longitudinally with respect to the connecting/FSM assembly 130. Such a connection mechanism avoids undesirable rubbing of the fingers by the orthosis device.

The connecting/force sensing module 130 also serves a force sensing purpose and to do so comprises force sensors (not shown in FIG. 1D) that are capable of measuring forces caused by patient-induced finger flexion and extension vis-à-vis motor activated movements of the orthosis device 106. The force sensing function of the connecting/force sensing module 130 is useful for various purposes, including, for example, to ascertain the degree of flexion and extension ability the patient has without assistance from the orthosis device 106, to determine the degree of motor-activated assistance is needed or desired to cause flexion and extension of the fingers during a rehabilitative exercise, and other purposes one of skill in the art will readily appreciate.

The pushing-and-pulling wire 126—which as described previously is attached on its proximal end to a linear motor inside the main housing structure 124—is attached at its distal end to the connecting/FSM assembly 130. As such, when the linear motor pulls the wire proximally, the attached assembly 130 is pulled proximally, which causes the flexible intermediate structure 128 to flex so its distal end is directed more upwardly so as to cause or assist in extension movement of the secured index and adjacent middle fingers. The upward flexing of the flexible intermediate structure 128 so that its distal end is directed more upwardly (and also its return) is enabled by the baffle structure of the flexible intermediate structure 128. In particular, a generally flat bottom structure 132 is provided on the flexible intermediate structure 128, wherein the bottom structure 132 is configured to attach to a bottom or hand-side of each of the individual baffle members, whereas an opposite or top-side of each of the individual baffle members are not so constrained and thus are free to be compressed closer together or expanded further apart by operation of the pushing-and-pulling wire 126 enlarging and/or reducing the top-side distance between the distal end of the main housing structure 124 and the proximal end of the connecting/FSM module 130.

Accordingly, the linear motor pulling the pushing-and-pulling wire 126 proximally causes the upper or outer portion of baffle structure to become longitudinally compressed while the lower or underside of the baffle structure remains a constant longitudinal compression state. Therefore, the pulling of the wire 126 proximally causes the flexible intermediate component 128 to flex so that its distal end is oriented more upwardly, thereby causing or assisting the index and middle fingers to be extending or in other words opened. Conversely, the linear motor pushing the pushing-and-pulling wire 126 distally causes the upper or outer portion of baffle structure to become longitudinally uncompressed or expanded while the lower or underside portion of the baffle structure remains in the same state of longitudinal compression, and as such, the pushing of the wire 126 distally causes the flexible intermediate component 128 to flex back to its distal end becomes oriented more downwardly, thereby causing or assisting the index and middle fingers in becoming flexed or in other words in becoming closed.

The main housing component 124 accommodates three straps 140 to removably secure the main housing component 124 and thus the other attached components of the device 106 to the forearm and top of the hand as shown in FIGS. 1A and 1D. The three straps 140 may be, as in this example, hook-and-loop or Velcro® type straps. Each of the straps 140 connects on a bottom of one lateral side of the main housing component 124 and extends around the arm to a bottom of the opposite lateral side of the main housing component 124. In this example, a first strap 140*a* is positioned vis-à-vis the main housing component 124 so that the strap 140*a* may be wrapped around the subject's forearm generally at a midpoint between the subject's elbow and wrist; a second strap 140*b* is positioned vis-à-vis the main housing component 124 so that the strap 140*b* may be wrapped around the subject's forearm at a position just proximal of the subject's wrist; and a third strap 140*c* is positioned vis-à-vis the main housing component 124 so that the strap 140*c* may be wrapped around the subject's hand and between the thumb 136 and index finger 120.

The finger stay component 122 in the example of FIGS. 1A and 1D has an upper surface that slidably connects with an underside surface of the connecting/FSM assembly 130, so that, as described previously, flexion and extension movement of the connecting/FSM assembly 130 translates to flexion and extension movement of the finger stay component 122 (and hence the fingers secured therein), yet the finger stay component 122 is free to slide longitudinally with respect to the connecting/FSM assembly 130. The finger stay component 122 is provided, as shown, with an upper plate that rests above the two secured fingers and a lower generally horizontal plate that rests below the two fingers. Two adjustable straps 123*a*, 123*b* are provided with the two plates to secure the plates in place with the index and middle fingers secured as a unit between the two plates. Further detail of the finger stay component 122 is provided in FIGS. 7A-7B, which will be described below.

Figure 2A:
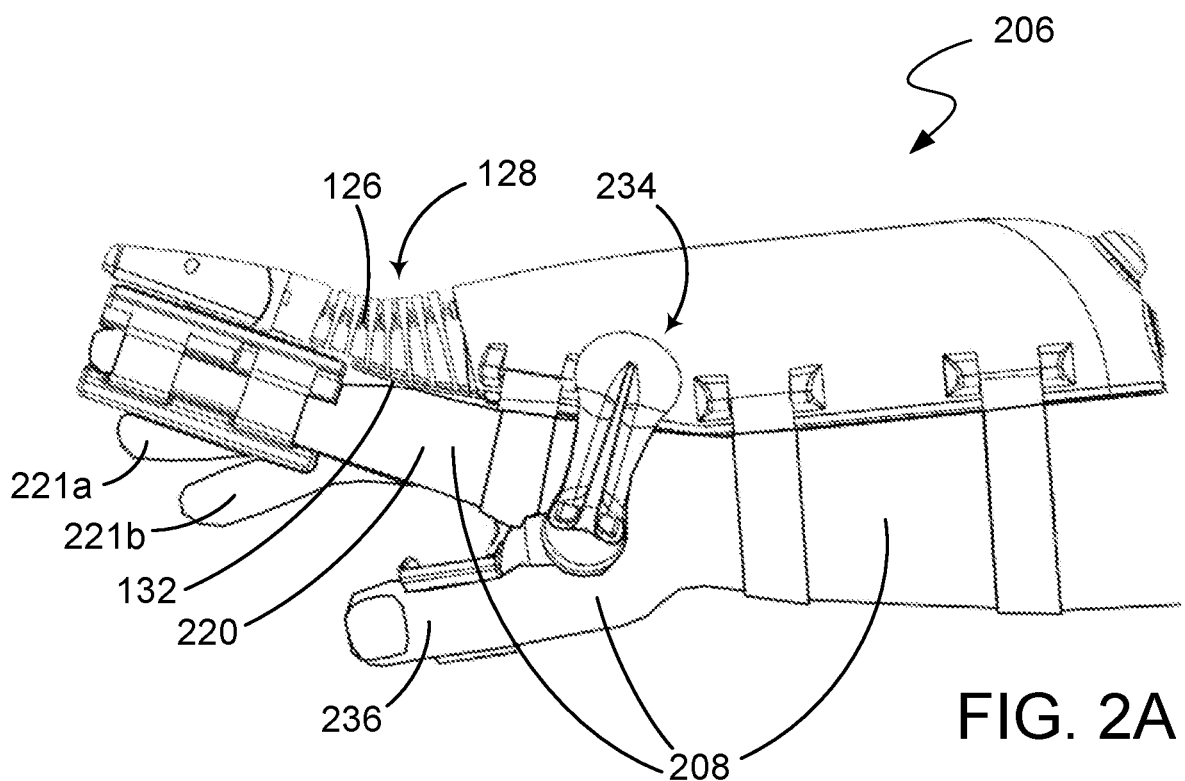
FIG. 2A is a diagram of an orthosis device similar to the device of FIG. 1D except being adapted to be worn on the subject's right forearm and hand instead of the left, which orthosis device is shown in an extended position in which an index finger and middle finger of the subject's right hand attached to the orthosis device are in an extended position.
Figure 2B:
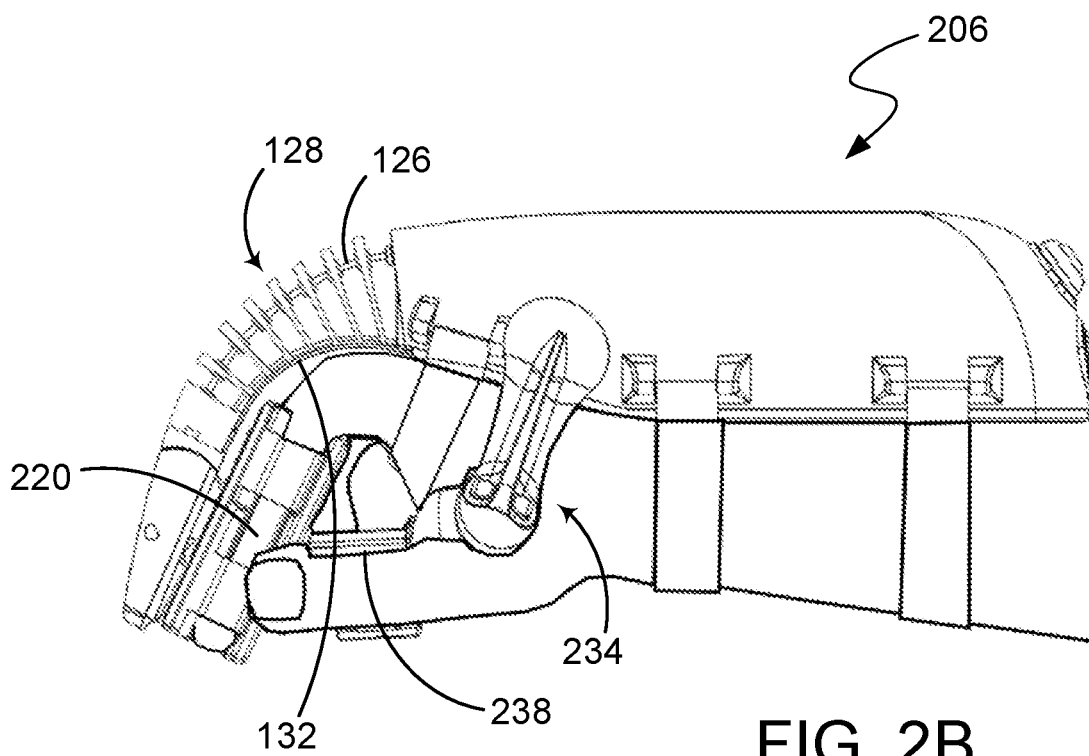
FIG. 2B is a diagram of the orthosis device similar to the device of FIG. 1D except being adapted to be worn on the subject's right forearm and hand instead of the left, which orthosis device is shown in a flexed position in which an index finger and middle finger of the subject's right hand attached to the orthosis device are in a flexed position.

Referring now to FIGS. 2A and 2B, there is shown an orthosis device 206 designed to be worn on the right arm and hand instead of the left as in the orthosis device 106 of FIGS. 1A and 1D. The orthosis device 206 of FIG. 2 is otherwise identical to the left-sided device 106 of FIG. 1. The orthosis device 206 is shown in an extended or open position in FIG. 2A and in a flexed or closed position in FIG. 2B.

As will be appreciated with reference to FIGS. 2A-2B, the flexible intermediate component 128 is configured to maintain a gap between its structure and the patient's knuckles, throughout the complete range of finger flexion and extension movement. In addition, the design of the flexible intermediate component 128 along with the manner in which the orthosis device 106 connects to the fingers (namely, with a finger stay component 122 having an upper surface that connects in a manner that is slidable longitudinally to the underside of the connecting/FSM assembly 130 positioned generally above the fingers). This feature provides, among other things, for the comfortable flexion and extension of the fingers, for example, by avoiding or minimizing any telescoping and/or rubbing of the finger stay component 122 and its straps 123a, 123b against the secured index and middle fingers. Otherwise, flexion and extension movement may be more difficult and/or uncomfortable.

In various implementations, an orthosis device in accordance with design principles of the present disclosure may cause or assist with various other motor activities in the hand and arm beyond movement of fingers as with FIGS. 1A and 1D. For example, an orthosis device within the scope of the present disclosure may be designed so that it causes or assists in the movement of the patient's wrist, thumb, elbow and/or shoulder, in addition to or alternative to movement of fingers. In other implementations, an orthosis device within the scope of the present disclosure may facilitate movement of other extremities, such as the foot, ankle, knee or hip.

The rehabilitation system 100 of FIG. 1A includes a BCI component to process brain signals to ascertain intentions of the patient and initiate predetermined or calculated motor or other mechanical responses of an orthosis device in response thereto. In some implementations, the wearable orthosis device 106 may include embedded processing equipment (not shown in FIGS. 1A and 1D) that include a BCI component and thus perform the BCI functions. In other implementations, the BCI component and processing functionality may be provided separate from the orthosis device, for example, by an application program residing upon and being executed by a local computing system such as the local computing system 110 (e.g., table computer) of FIG. 1A or alternatively residing upon and being executed by a remotely located and networked computer system such as the central rehabilitation management computing system 116 of FIG. 1A.

The system 100 shown in FIG. 1A also enables remote monitoring of the patient's rehabilitation efforts and progress. For example, the tablet computer 110 and/or orthosis device 106 may periodically send reports via a local router 114 and network to the central rehabilitation management system 116. The reports may indicate, for example, compliance information, namely, whether or not the patient has carried out required or suggested rehabilitation sessions. In addition, the reports provided to the central system 116 may be reviewed by a health care provider or other rehabilitation specialist to see what if any progress is being made with the rehabilitation effort, and provide instructions for future therapy sessions, feedback, and perhaps encouragement to the patient where appropriate. In some implementations, information included in reports from multiple patients may be anonymized and aggregated to identify factors and trends which may generally lead to improved rehabilitation results for patients. By analyzing overall device usage statistics (e.g., time of use, number of repetitions, etc.) and patient characteristics (e.g., type of impairment, age, etc.), for example, the central rehabilitation management system 116 may identify groups of patients who may generally benefit from particular types of therapy. For example, the system 116 may determine that a patient (e.g., a stroke patient of a certain age) may benefit from a particular type of therapy session (e.g., a session including a certain number of repetitions at a certain time of the day), based on the progress of similar patients (e.g., other stroke patients of a similar age) having conducted similar therapy sessions. Health care provider feedback and therapy session instructions may be provided to the patient, for example, on the display device 112 of the tablet computer 110 at the beginning of the patient's next rehabilitation session.

Figure 3A:
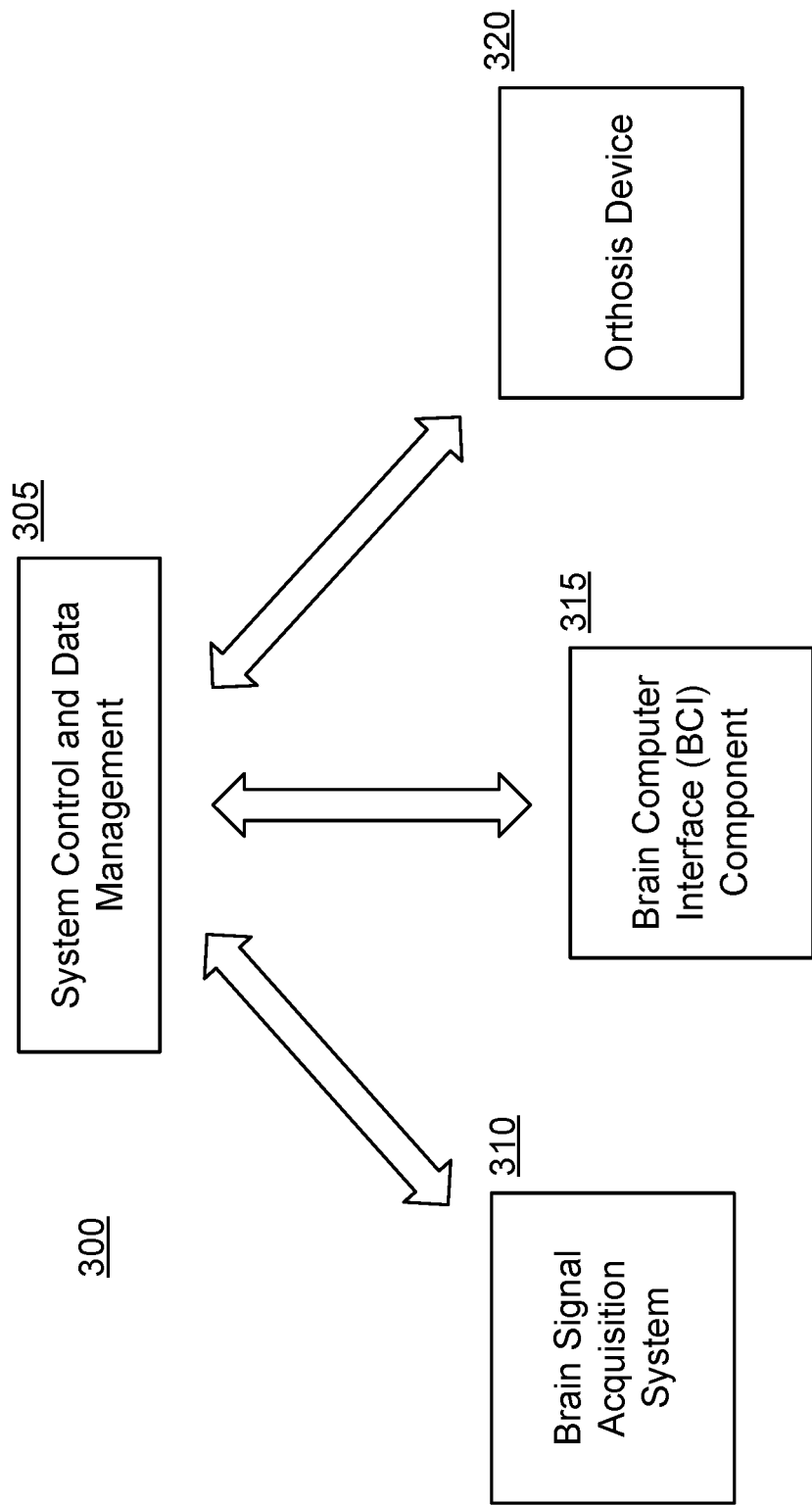
FIG. 3A is a general block diagram illustrating a relationship among parts of the rehabilitation system of FIG. 1A.

Referring now to FIG. 3A, there is shown a generalized block diagram of a rehabilitation system 300. This block diagram of FIG. 3A illustrates not only the example rehabilitation system 100 of FIGS. 1A-1D and 2A-2B, but also other embodiments of rehabilitation systems, for example, systems for the control of other body movements (e.g., arm, shoulder, elbow, wrist, hand, leg, knee, ankle, foot, etc.), and systems that use different types of brain signal acquisition systems other than the EEG brain signals as shown in the FIG. 1A implementation (e.g., systems that alternatively use implantable electrodes).

As shown in FIG. 3A, the rehabilitation system 300 includes: (i) a system control and data management component or components 305; (ii) a brain signal acquisition system 310; (iii) a brain computer interface (BCI) component 315; and (iv) an orthosis device 320. The orthosis device 320 may be a body-worn and thus a portable, body part movement control and/or movement assistance system. The system control and data management system 305 may include not only local control and data management of the system 300, namely, at a site co-located with a subject performing rehabilitation (and perhaps integrated with the BCI component 315 and/or the orthosis device 320 or integrated in a local computing device such as a local computing system 110 in the form of a tablet computer as in the FIG. 1A example), but also may include a remote, network accessible central rehabilitation management computing system such as system 112 of the FIG. 1A example. A central rehabilitation management computing system may be used, for example, in set-up and on-going operation of the system, and may be located at a location that is remote of the patient, for example, at a healthcare facility or the facilities of some other type of services provider.

Generally, the brain signal acquisition system 310 acquires brain signals, performs low-level signal processing, and transmits the brain signals, for receipt by the BCI component 315 under control of the system control and data management system 305. The brain signals may be acquired by the acquisition system 310 using a number of arranged electrodes that are part of the acquisition system. As discussed previously, these electrodes may be EEG surface electrodes or implantable electrodes (for example, ECOG electrodes or "point-style" electrodes). The acquired neural signals, for example, may also include magneto encephalography (MEG) signals, mu rhythm signals, beta rhythm signals, low gamma rhythm signals, high gamma rhythm signals, action potential firing, and the like. The brain signal acquisition system 310 may also include processing circuitry to perform the low-level processing and formatting of brain signal information for use by the BCI component 315, as well as a connection interface to enable that transmission.

The connection for transmission between the brain signal acquisition system 310 and the BCI component may be wireless or hard-wired and may be direct or indirect through intermediate components, and thus a connection interface in the brain signal computing system 310 and the components with which the system 310 communicates would be adapted accordingly to enable the wireless or hard-wired transmissions. For example, a connection interface may include USB interface devices, Bluetooth® communication devices, Wifi communication device or some other wireless or hard-wired transmission protocol interface mechanisms and circuitry.

In some implementations, body worn equipment of the system 300 may include both the movable and actuatable equipment to cause body parts to be moved or assist in their movement as well as the BCI component 315. The BCI component 315 in this example may generally include BCI processing capability that is adapted to be worn on a user (e.g., on the user's forearm as in the FIG. 1A example or some other body part in other implementations). The body movement assistance component in such an implementation may be operably connected to the BCI component 315, and also may be adapted to be worn by the user (e.g., on a user's hand as in the FIG. 1A example or some other body part to be moved in other implementations).

The BCI component 315 includes processing and control circuitry to operate BCI functions in training modes, operational modes (e.g., rehabilitation sessions), calibration modes, and communications modes. As such, the BCI component 315 includes one or more processing units such as a central processor unit (CPU) component, volatile memory such as random access memory (RAM), and non-volatile memory such as read-only memory (ROM) and/or various forms of programmable read-only memory (PROM) for the storage of software or firmware programs and operating parameters that may be periodically updated. The BCI component 315 may also include one or more of the following additional hardware components: (i) one or more batteries to enable the BCI component to be portable (the batteries may provide power to the various components of a wearable device, and may be recharged via an adapter or charging device (not shown here)), (ii) visual output display equipment including visual displays and related display drivers and circuitry, (iii) user input devices such as on/off and other buttons or touch-screen displays to enable manual user input, (iv) audio output equipment to provide audio commands, information and prompts to the user, (v) audio input equipment such as a microphone to receive audio input from the user, and (vi) connection interfaces to enable communication between the BCI component 315 and the brain signal acquisition system 310 for example to receive wirelessly or hard-wired transmitted neural signals, and also between the BCI component 315 and the system control and data management system 305.

The system 300 may include various components for providing information to and receiving input from a user. Visual output display equipment, for example, may be a regular or touch screen display for providing visual prompts (e.g., graphics, instructions, etc.) or other sorts of information to the user and/or for receiving user input. The input devices, for example, may include one or more buttons for controlling (e.g., pausing, powering on/off, sending data, receiving data, changing modes, etc.) the wearable device. For example, input devices such as buttons may serve as soft keys alongside display equipment and/or may be situated away from the display equipment. Audio output equipment (e.g., speakers), for example, may be used for providing auditory prompts (e.g., live or recorded spoken instructions, tones indicating success or error conditions, etc.). Audio input equipment (e.g., microphone), for example, may be used for receiving spoken input from the user (e.g., voice controls) and/or may serve with the audio output equipment for conducting a live communication session with a remote technician.

In terms of software and/or firmware programs, the system control and data management system 305 and BCI component 315 may include various programs that are stored in non-volatile memory that include executable program instructions that are executed by a CPU to carry out the various processing functions. This may include one or more of the following program modules: (i) a neural signal interpreter for interpreting neural signals received from the brain signal acquisition system 310, and specifically determine whether those received signals are indicative of a user intention to perform certain predefined body movements which will be caused or assisted by the orthosis device 320; (ii) a device control module for providing control signals to the orthosis device to actuate movement; (iii) a training mode module for carrying out training processes; (iv) an operational mode module for carrying out the operation of the system 300 in normal operation, for example, in a rehabilitation session, (v) a calibration mode module for carrying out the operations calibration processes, and (vi) a communications module for carrying out communications processes between the brain signal acquisition system 310, the BCI component 315, and the orthosis device 320, and a central network-accessible rehabilitation management system.

The non-volatile memory may also include information storage areas for operational parameter settings or other input information used during the operation of the BCI component 315. The settings and other input information may be input by a user or may be transmitted to the BCI component 315 from the system control and data management system 305, for example, from a remote, network-accessible system. The information storage areas may include one or more of the following: (i) device parameter setting storage for storing various operational parameter settings that may be, for example, selected by a user or selected and provided by a central rehabilitation management system, (ii) user intention information storage for storing one or more sets of previously ascertained brain signals, each set being indicative of a user intention to perform a different body movement, and specifically movements that are assisted by a movement (this intention information being for use by a neural signal interpreter program, for example), (iii) calibration data storage for collected calibration data including brain signal information that is collected during a calibration session, and which may be retrieved and sent by the BCI component 315 to a remote, network-accessible central system for evaluation, (iv) body motion range parameter settings (which may be used by equipment that controls movement of the orthosis device 320) comprising parameter settings that dictate a range of motion by the orthosis device 320) for example, to what extent will a finger be flexed and extended), and (v) usage information storage wherein information regarding the usage of the wearable BCI/assist device by the user may be stored, for example, how many times the device has been used, for how long, when, and what the results of each usage session were (which usage information may be retrieved and sent by local equipment to a remote, network-accessible central system).

The orthosis device 320 may operate under the control of the BCI component and may include various components to cause or assist in body movement (e.g., an external robotic assist device, a prosthetic device, a functional electrical stimulation (FES) device, etc.). To do so, the orthosis device 320 may include one or more sensors, tactile devices, motors, electrical stimulators, and movable components that may be coupled to a body part. Sensors, for example, may be used to detect an amount of force applied to a body part in order to assist in the movement of the body part, to detect the position of the moveable components, and/or to detect forces that are being created by a patient or subject in causing intended movements. Such force detectors may provide information as to whether the patient is effectively moving the body part on the patient's own, and if not, how much assistance was needed in order to effectuate the body movement, and is the patient's motor control such that the patient is resisting the movement without intending that. Position detectors may be used, for example, to inform the system 300 that the fingers are now fully flexed, fully extended, or at some intermediate position. Information collected by sensors may be provided to a device control module, a training mode module, a calibration mode module, and operational mode module.

Tactile feedback devices, for example, can provide tactile feedback (e.g., vibrotactile feedback) to a user in association with a prompt and/or in association with an identified user intention. In some implementations, to prompt the user to move a body part (e.g., a hand), a tactile device may operate (e.g., vibrate), alone or in combination with other sorts of prompt mechanisms (e.g., visual and/or acoustic). Similarly, to indicate to the user that an intention to move a body part has been identified, in some implementations a tactile device may operate (e.g., vibrate), alone or in combination with other feedback mechanisms (e.g., visual and/or acoustic).

Motors, for example, may include rotary, servo, and/or linear motors for driving gears, pistons, and the like. A device control module executed by a processing unit, for example, may provide signals for controlling the motors. Movable components may be coupled to and moved by the motors, for example, and may include one or more mechanisms for guiding or assisting the movement of a corresponding body part.

Electrical stimulators, for example, may use electrical currents to activate the muscles or nerves of a device user's affected body part. For example, upon identifying the user's intention to move a body part (e.g., a hand), electrical stimulators may deliver electrical current to the body part, thus facilitating movement. In some implementations, electrical stimulation of body parts may be provided alone or in combination with mechanical mechanisms for guiding or assisting the body parts.

A remote, network-accessible central rehabilitation management system, such as system 116 in FIG. 1A for example, may include one or more computing devices configured to receive information from the brain signal acquisition system 310, BCI component 315, the orthosis device 320, and/or local components of the system control and data management system 305, to execute one or more applications for processing, analyzing, and tracking rehabilitation and other data, and to provide operation and configuration data to the system 300. For example, a remote, network-accessible central system may execute computer application code associated with a device usage analyzer and a rehabilitation management module. A device usage analyzer, for example, can be used by a technician for analyzing information received from a remote device and for determining operation instructions and parameters to be used by the remote device. A rehabilitation management module, for example, may be used by a technician or healthcare specialist for tracking a device user's progress over time and for configuring local components of the system 300.

Figure 3B:
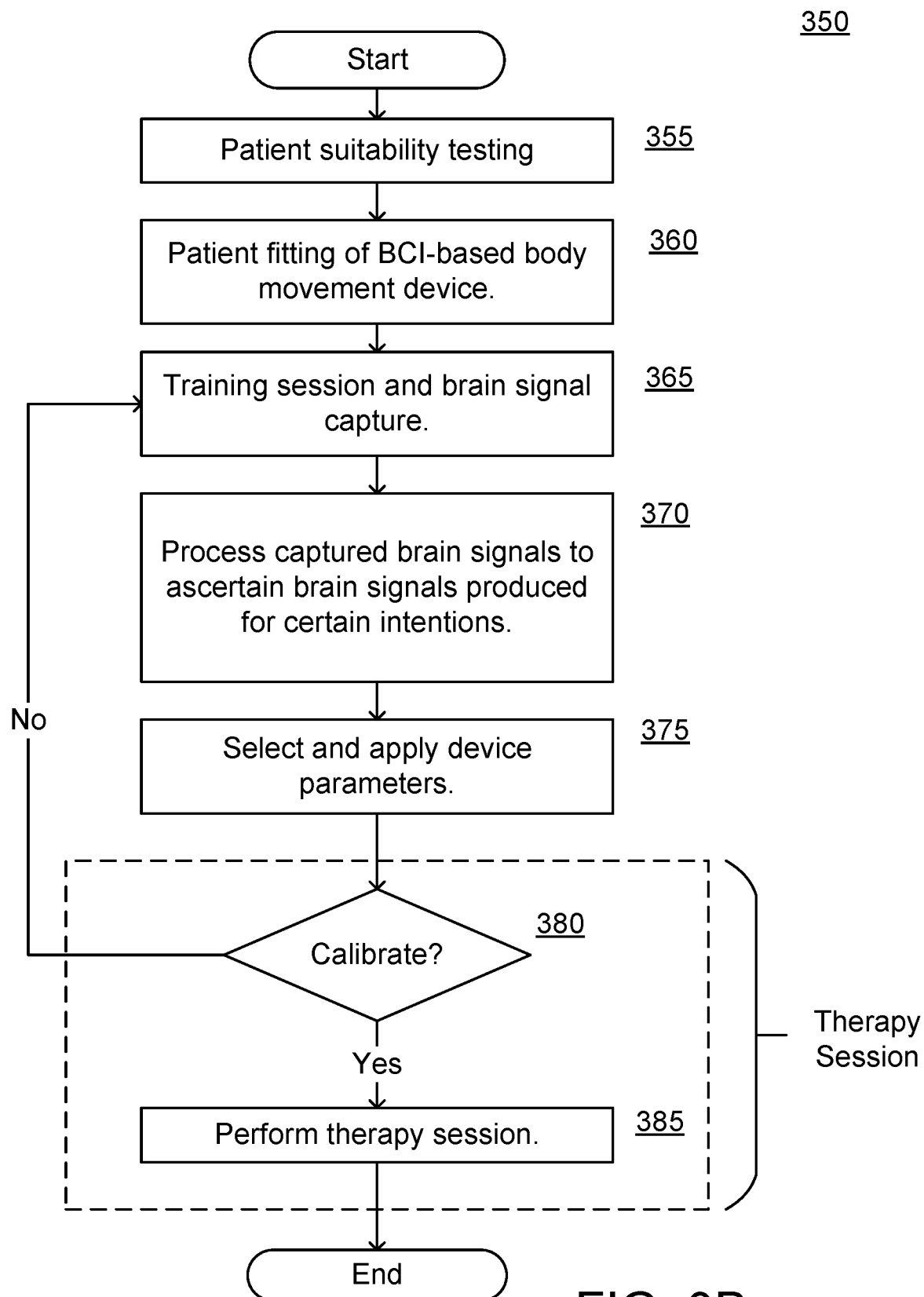
FIG. 3B is a flow diagram of a process for using the rehabilitation system of FIG. 1A.

The components of FIG. 3B may each include a connection interface for receiving data from and providing data to other devices through wired and/or wireless connections. For example, connection interfaces may include USB drivers, Bluetooth drivers, WiFi drivers, and/or mobile data connection drivers, such as 3G drivers, 4G LTE drivers, and 4G WiMAX drivers. A connection interface of the BCI component 315, for example, may be configured to receive neural signal data directly from a corresponding connection interface of the brain signal acquisition system 310. Connection interfaces may be configured to send and receive data between the local parts of the system 300 and a remote, network-accessible central system through a network.

The system 300 may additionally include a local user computing device, such as a laptop computer, a desktop computer, a smartphone, a tablet computing device (in the case of FIG. 1A), a personal digital assistant (PDA), and/or a media computing device. The user computing device may include the BCI component 315 in some implementations, or alternatively may communicate with the BCI component not included thereon. The local user computing device may obtain rehabilitation data (e.g., log of rehabilitation sessions, summary of repetitions performed, duration of use, and progress along a rehabilitation schedule) from the use of the system 300 in a rehabilitation session for example. The user computing device may also present rehabilitation data through a user interface that may be easier to use and interact with than a user interface provided through the display of wearable components. Additionally, user computing device may communicate with a central management computing system through a network to view rehabilitation data stored remotely. For example, the user computing device may include one or more applications (e.g., web browser) that may authenticate the user associated with the user computing device (e.g., login) and that may provide access to rehabilitation data that has been provided by local equipment to the central rehabilitation management computer system.

Referring to FIG. 3B, we turn now to a general process 350 of how a rehabilitation system such as the rehabilitation system 100 shown in FIG. 1A may be used. For purposes of illustration and by way of example only, the following introductory description of use relates to a unilateral stroke patient undergoing rehabilitation of a motor impaired or paralyzed hand. That said, the devices and methods described in this specification are not limited to that stroke rehabilitation application.

The first thing that may occur for a stroke patient with impaired hand motor control is that the patient may undergo testing (355) to determine whether or not the patient is a suitable candidate for therapy by a BCI-based system. The timing along a rehabilitation/recovery timeline of when such a stroke patient may undergo the testing can vary. For instance, a stroke patient may undergo the testing (355) after acute or sub-acute rehabilitation, or after outpatient rehabilitation. One purpose of this suitability testing is to determine whether or not finger movement intentions can be ascertained from brain signals generated by the patient and acquired by the brain signal acquisition system 104. As an example, this suitability testing may be performed using the brain signal acquisition system 104 (appropriately selected and sized for the patient, and positioned on the patient's head appropriately) and the central rehabilitation management system 116 (which may be capable of receiving wireless transmissions directly from the brain signal acquisition system 104). In other words, suitability testing may be done without the need for the wearable orthosis device 106 and associated tablet computer 110, which may be appropriate given that the patient has not yet been deemed suitable for therapy using such a device 106 and computer 110. The suitability testing may be done, for example, at a rehabilitation clinic where the central rehabilitation management system 116 is located, and under the supervision of a qualified BCI and/or rehabilitation therapy expert. Alternatively, suitability testing may be conducted with the patient located remote from the central rehabilitation system 116 and clinic, with the remotely captured brain signals being transferred via network to the central rehabilitation management system 116 for processing and analysis.

In some implementations, before performing the suitability testing described in the previous paragraph using the brain signal acquisition system 104, a patient may participate in a first round of suitability testing using a research grade EEG headset and BCI device (e.g., BCI2000) as part of the patient suitability testing (355). Such research grade equipment may be used to determine whether a patient is exhibiting any ipsilateral or motor derived signals for BCI use. The research grade equipment may be more sensitive to brain signals than the brain signal acquisition system 104, and thus may be used as part of an initial screening process before screening is performed by the brain signal acquisition system 104 and the wearable orthosis device 106 and associated tablet computer 110. The screening using research grade equipment can involve similar procedures as those described with regard to the brain signal acquisition system 104 and the wearable orthosis device 106. Alternatively, research grade equipment may also use anatomic or functional magnetic resonance imaging or magnetoencephalography to further augment suitability of a patient for a BCI system.

If a patient passes one or more screening tests using the research grade equipment, which may not be portable and which may be located in a clinic/research facility, the patient may proceed to screening using the brain signal acquisition system 104 and wearable orthosis device 106 and associated tablet computer 110. The screening process using the brain signal acquisition system 106 and the wearable orthosis device 106 and associated tablet computer 110 can involve displaying real-time (near real-time) results on a display, comparing the results with those from the research grade screening for consistency with regard to various detected control features for the patient (e.g., brain signal that has been determined to indicate and correspond to user intent to move a body part along the same side of the user's body as the side of the brain where the signal was detected—an ipsilateral brain signal), and using the various detected control features to perform cued control (e.g., device directed actions by the patient) to accomplish one or more tasks (e.g., moving a graphical bar displayed on the tablet computer 110 past a threshold level). If the patient successfully performs one or more of the tasks, the patient may be identified as a candidate for the rehabilitation using the brain signal acquisition system 104 and the orthosis device 106 and associated tablet computer 110. Additionally, the brain signal acquisition system 104 may detect specific physiologic features (e.g., a specific frequency band, amplitude modulation, or phase or time series related phenomenon) that may predict the patient's response to a rehabilitation regime.

Assuming the patient is a suitable candidate for the rehabilitation, the patient may then be fitted (360) with an appropriately sized wearable orthosis device 106. It may be that the rehabilitation clinic will have several sizes on hand for the wearable orthosis device 106. Alternatively, the orthosis device 106 may be manufactured on site and sized specifically for the patient, for example, using three-dimensional (3D) printing or other on-site customized manufacturing techniques. For example, three-dimensional scans of a patient can be performed, and a customized model of the orthosis device 106 can be manufactured for the patient, based on the scanned measurements.

Next, the patient may undergo initial training exercises (365), which may be done, for example, also at the rehabilitation facility, and under the supervision of a qualified BCI and/or rehabilitation expert. The purpose of initial training exercises is to ascertain what specific brain signals that the brain signal acquisition system senses when the patient is planning and executing certain intended movements (the sensed brain signals may include, for example, the electrode or electrodes at which changes from a baseline signal level are detected, thus indicating some brain activity, and at what magnitude and signal frequency that brain activity was sensed.

To do these initial training exercises, the patient may be prompted to try to accomplish various finger movements, and when the patient is preparing to perform, and in the process of attempting to perform, those tasks, the brain signals produced during that time may be acquired and eventually stored in memory of the orthosis device 106 and/or the tablet computer 110. The finger movement prompts may be provided by the tablet computer 110, for example, using visual displays provided on the table computer's display device 112 and/or using other sensory prompts (e.g., audio signal prompts, vibrotactile prompts, etc.) produced by the orthosis device 106 or the tablet computer 110. As those prompts are being provided to the patient, the brain signal acquisition system 104 continuously captures brain signal samples sensed at each of the multiple electrodes (magnitude at various frequency levels).

The initial training exercises may include several distinct calibration exercises during which specific brain signals are tested and various levels of feedback are provided to the patient. For instance, in a first calibration exercise a patient can be cued/prompted to alternate between resting and generating ipsilateral brain signals (e.g., think of moving right hand). This first calibration exercise can be configured to assess whether the patient is able to generate sufficient physiological change with regard to the previously identified control feature(s). The ipsilateral movement performed by the user can be compared against periods of rest to make such an assessment. During this first calibration exercise, feedback may not be provided to the patient. In a second calibration exercise, a patient may be prompted/cued to generate ipsilateral signals (e.g., think of moving right hand) to control an object that is presented on a display 112 of the tablet computer 110, such a bar that moves based on the strength of ipsilateral signals that are generated by the patient. In a third calibration exercise, a patient may be prompted/cued to generate ipsilateral signals that will control movement (e.g., opening and closing) of the wearable orthosis device 106. The cues can be presented on the display 112 of the tablet computer 110 and feedback can be provided in the form of movement of the orthosis device 106, as well as through sensory feedback (e.g., playing sound, engaging a vibrotactile device, delivering electrical stimulation) and/or other visual feedback (e.g., presenting information on the display 110). The sampling rate of the brain signal acquisition system 104 may be, for example, 256 Hz and/or 512 Hz.

Signals containing representations of captured brain signals and other relevant information may be transmitted wirelessly by the acquisition system 104 for receipt by either the wearable orthosis device 106 directly or to the orthosis device 106 by way of the tablet computer 110. The brain signal data received by the acquisition system 104 may be in any of a variety of appropriate forms, such as amplitude, power modulation, phase alteration, change in event related potential, and/or change in the raw time series of the signal.

The brain signal information received by the wearable orthosis device 106 and/or in the tablet computer 110 may have its timing of acquisition noted in some manner (for example, by a time-stamp), and stored in memory of the wearable orthosis device 106 and/or in the tablet computer 110. This allows, for example, the timing of the acquired brain signals vis-a-vis the timing of various prompts to the patient to be correlated. After a series of training prompts are completed (and brain signal and timing information is stored in memory as described), the acquired data may be transferred from the orthosis device 106 or the tablet computer 110 to the central rehabilitation management system 116 for evaluation and processing.

Generally, the central rehabilitation management system 116 may perform computer processing (370) on the data to ascertain the particular signature of brain signals (e.g., which specific electrodes and magnitudes and frequencies of signals) the patient produced when the patient was planning and attempting to execute the various finger movements that the patient was prompted to perform. The central system 116 may then determine (370), from the ascertained brain signals, appropriate parameter settings and/or control features to be used by the orthosis device 106 and associated tablet computer 110, which can include electrodes specification, frequency band, and/or changes in power or amplitude of the signal. The central computer 116 may perform this analysis and feature selection, at least in part, using input from a technician.

The central system 116 may then transfer those parameter settings to the tablet computer and/or to the wearable orthosis device 106, so that the parameter settings are used during the patient's rehabilitation exercises. In some implementations, the information transmitted to the orthosis device 106 and/or its associated tablet computer 110 may include instructions such as a series of suggested rehabilitation sessions (e.g., an optimal type and manner) for the patient, and other configurable settings such as time limits between calibration sessions.

The patient is now able to perform rehabilitation exercises using the brain signal acquisition system 104, wearable orthosis device 106, and the tablet computer 110. Owing to the portable nature of the wearable orthosis 106 and tablet computer 110, the patient may perform the rehabilitation exercises outside of a rehabilitation clinic. For example, the patient may perform the exercise in the patient's home. Such home delivered rehabilitation is believed to assist in rehabilitation efficacy. For example, the portability and wearable aspects of the system 110 can increase the number of opportunities to use the system 100, which can increase the number of repetitions that a patient performs using the system 100. Such an increase in the number of repetitions is believed to be positively correlated to improved functional outcomes for patients. Additionally, the portability and wearable aspects of the system 100 permit for the system 100 to be used in and integrated into a patient's daily life, which can allow for a patient to perform rehabilitation tasks that are context dependent (e.g., folding laundry, opening doors, picking-up and organizing belongings) rather than rote (e.g., repeatedly opening and closing hand without specific purpose). Such context-dependent rehabilitation tasks are also believed to positively impact functional outcomes for patients. Taken in combination, the ability to perform physical tasks using the system 100 more frequently and within the context of a patient's daily life is likely to enhance the brain plasticity and rehabilitation benefits beyond classic in-patient settings with predefined periods of therapy.

To set up a rehabilitation session (385, or alternatively 380 and 385) of a type shown generally in FIG. 3B, the patient may first put on the brain signal acquisition system 104 (e.g., EEG headset), and position and secure the electrodes 118 (see FIG. 1B) in place against the skin adjacent the brain. Ideally, the electrode positions will be positioned in rehabilitation as they were in the training exercise, but in some cases that may not be possible. In addition, the subject may have undergone a change in brain signals since the prior therapy session (385) and/or training session (under the process of 365, 370 and 375 of FIG. 3B). For these reasons, a calibration process (380) may be utilized, as will be discussed in more detail below. The patient will then put the wearable orthosis device 106 on his or her forearm and hand as described previously, namely, by securing the main housing structure 124 to the forearm and hand and position the thumb and secure the index and middle fingers as shown in FIG. 1D. The patient may then activate (turn on) the brain signal acquisition system 104, the wearable orthosis 106, and the tablet computer 110 to start the rehabilitation session.

The rehabilitation session (385) may be performed in a variety of ways. In one scenario, the patient may perform, in a BCI mode of operation for example, any finger movement desired of the types addressed in the training session. For example, the patient may first desire to perform ten repetitions of flexing and extending the index/middle finger pair. In this example, the patient first attempts a finger pair flexing movement, and in doing so produces certain brain signals corresponding to the planning and execution of that finger pair movement. The brain signal acquisition system 104, during an entire portion of a rehabilitation session (385) when operating in a BCI mode, acquires periodic samples of brain signals and wirelessly transmits those samples to the tablet computer 110 and/or the wearable orthosis 106 for evaluation (at, e.g., 256 or 512 samples per second). Each sample may include a set of information including parameters (e.g., magnitude, frequency) of the signal sensed at each of the multiple electrodes. A BCI component (provided in either the wearable orthosis device 106 or in the tablet computer 110) processes those brain signal samples to determine the patient's intentions. If and when the BCI component detects that the patient has produced brain signals indicating that the patient intends to flex the index and middle finger pair, the BCI component will produce a control signal that activates the orthosis device 106 to assist or cause movement of the patient's index and middle finger pair.

During the rehabilitation session (385), the patient may be given continuous feedback via the tablet computer 110 and/or the wearable orthosis device 106. Feedback may take several forms and improves in the overall efficacy of the rehabilitation session. In general, feedback provided to a patient in a BCI mode of operation may be in the form of visual, acoustic, tactile (e.g., vibrotactile) and/or electrical stimuli that supplement a control response. One example of feedback in a BCI mode of operation is to provide an indication to the patient that a particular intention has been detected. One example way that this may be done is for the tablet computer 110 to produce a visual display (on display device 112) showing, for example, that a BCI component has detected a particular intention, for example, that a flexion movement of the index/middle finger pair be performed. The patient may easily be able to see, on a conveniently positioned display device for example, that this particular intention was detected by the system 100. Another example way that feedback may be presented in a BCI mode of operation is for the orthosis device 106 and/or the tablet computer 110 to generate sound e.g., using a speaker included in the tablet computer 110 or implemented in the orthosis device 106). For example, tones may be produced or there may be recorded spoken feedback, such as a recorded voice saying, "opening hand." Another example way that feedback may be presented in a BCI mode of operation is using tactile feedback and/or electrical stimuli using the wearable orthosis device 106. For example, upon identifying a user's intention to open his/her hand, the wearable orthosis device 106 may provide tactile (e.g., vibrotactile) feedback to the user and/or to provide electrical current to the user's hand. In some implementations, multiple forms of feedback in a BCI mode of operation may be provided to a user simultaneously. Simultaneous presentation of visual, acoustic, tactile, and/or electrical feedback may simultaneously excite multiple areas of a patient's brain, for example, and may encourage neuroplasticity.

The rehabilitation session (385) may in some implementations include prompts/cues that instruct the patient to perform particular actions using the system 100. In general, prompts/cues may include one or more visual, acoustic, and/or tactile elements. For example, the display device 112 can display cues for the patient to move his/her right hand (e.g., open right hand, close right hand), to move his/her left hand, and/or to rest. The tablet computer 110 can generate the prompts to be displayed on the display 112 (and/or output to the user through one or more other output mechanisms, such as a speaker and/or tactile device that is part of the wearable orthosis 106) based on a variety of factors, such as a predetermined therapy schedule generated by the central rehabilitation management system 116, current progress by the user (e.g., number of repetitions performed, progress along a therapy schedule), and/or information obtained by sensors of the wearable orthosis device 106 (e.g., levels of force detected by pressure sensors in the wearable orthosis device 106 indicating degrees to which a patient is driving movement of the wearable orthosis device 106 and/or emergence or regression of brain signals or features detected by the brain signal acquisition system 104).

In some implementations, the system 100 may be configured to also operate in a free assist mode during which a patient is able to use the wearable orthosis device 106 to perform tasks within the context of the patient's daily life. During a free assist mode, the wearable orthosis device 106 may be configured to operate in a non-cued BCI mode of operation wherein brain signals detected by the brain signal acquisition system 104 are continuously interpreted to determine what actions, if any, the user intended for the wearable orthosis device 106 to perform, such as opening and/or closing a hand onto which the wearable orthosis device 106 is mounted. The system 100 can provide a user interface, such as on a conveniently positioned display, which can provide feedback to the patient regarding the type of action that a BCI component has determined that the user intended through brain signals detected by the brain signal acquisition system 104. The wearable orthosis device 106 may be configured to perform actions (e.g., closing fingers, opening fingers) that the wearable orthosis device 106 determines to have been intended by the patient so as to enable the patient to interact with his/her environment more fully using the body part (e.g., hand) on which the wearable orthosis device 106 is mounted. For example, during a free assist mode a patient can generate brain signals to cause the wearable orthosis device 106 to close and open the patient's left hand when needed in order to open and close doors, to pick up objects around the patient's house, to fold laundry, and other daily tasks. As explained above, such contextual use of the wearable orthosis device 106 in the patient's daily life can enhance the rehabilitation for the patient.

With this type of feedback, if for example the patient is intending a particular movement and the BCI-based rehabilitation system 100 is not responding by assisting the patient in performing that movement, the patient will know immediately that the problem lies with the system 100 not detecting the patient's intention, and not some other problem. One cause of the intention not being detected may be that the electrodes 118 (FIG. 1B) of the headset 104 may not be in their proper positions, and adjustments to the positioning may solve the problem. Another cause of the intention not being detected may be that the patient's brain signals may have evolved over time during the rehabilitation process, via a process known as brain plasticity wherein neural pathways become reorganized. This in many cases may be a positive development for the patient, in that additional or different brain activity is occurring to compensate for the brain areas that were damaged by the stroke. For example, specific features may correlate with these plastic changes, such as an alteration in amplitude of a specific frequency band or a change in phase interaction between two cortical sites. As such, it may be appropriate for a calibration process (for example, 380 in FIG. 3B) to be performed to update the system 100 regarding the brain signals that the patient produces for a particular finger movement intention.

To perform a calibration process (380), the patient may perform a new training process similar to the process performed during set-up, or an abbreviated version of that training process. This calibration process may be guided by the wearable orthosis device 106 and associated tablet computer 110, for example, using appropriate displays on display device 112. For example, the system 100 may guide the patient through a number of finger exercises, and during that time obtain and store brain signal information in memory residing for example in the wearable orthosis device 106 and/or in the tablet computer 110. At the end of the calibration process, the patient may initiate a process wherein the data obtained during the calibration process is transmitted from the tablet computer 110 and or the orthosis device 106, over a network, to the central rehabilitation management system 116. The central system 116 may evaluate that data as described previously in connection with the initial training process, and once that is complete, transmit updates including updated operational parameters to the tablet computer 110 and/or the wearable orthosis device 106 for use in the next rehabilitation session. As such, this calibration process may be performed remotely of any rehabilitation clinic where the central system 116 is located or operated.

Another example of feedback that the system 100 may provide to the patient relates to the status of a particular rehabilitation session, and even more generally, to the status of attaining certain goals of the overall rehabilitation effort. In general, information may be provided in association with measured characteristics and phenomenon from the wearable orthosis device 106 and the brain signal acquisition system 104. Feedback provided to the patient, for example, can include information associated with repetitions during one or more rehabilitation sessions, and time of day and duration of use, which may be derived from the wearable orthosis device 106. Further, information associated with changes that may occur in the patient's brain physiology can be measured, documented, and presented (e.g., in the form of a graphic representation showing increased or decreased presence of signals associated with the performance of a task or in signals not associated with the task but associated with a rehabilitation outcome). For example, for a specific rehabilitation session, the system 100 may record the number of repetitions that the patient has done of a particular finger movement and display that for the patient on the display device 112. The system 100 may also determine and display suggested exercises to the patient. In addition, the system 100 may also sense and display a measure of force that had to be applied to the fingers to aid in the intended movement. If, for example, less and less force is being required to assist in the intended movement, this may indicate to the patient that progress is being achieved by the rehabilitation effort. The system 100 may also display, for example at the end of a rehabilitation session, a summary report of all of the exercises that were performed during the rehabilitation session, and in addition a general assessment of the patient's progress toward certain goals with the rehabilitation effort.

Figure 3C:
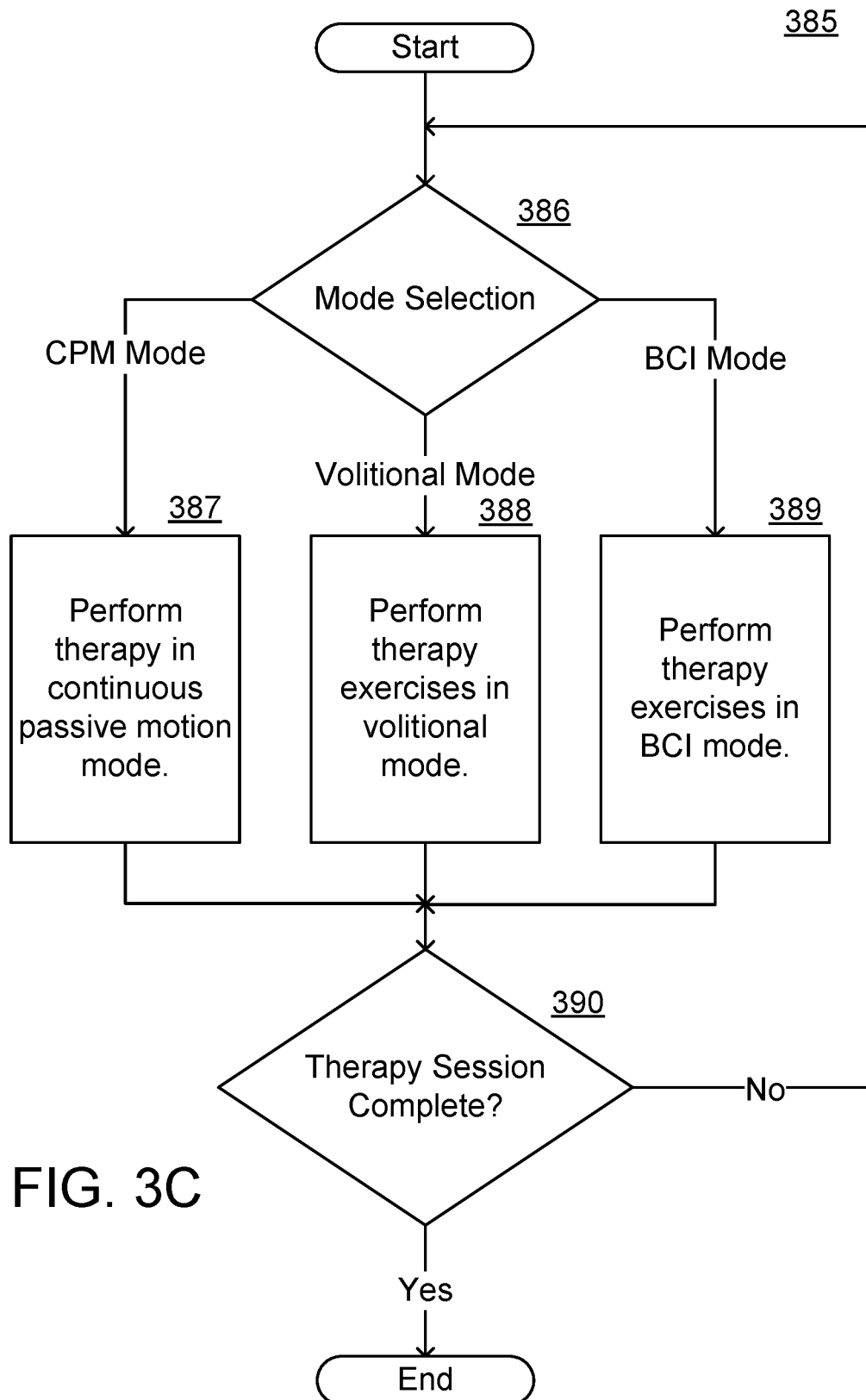
FIG. 3C is a flow diagram of a process for performing a therapy session, for example, within the process of FIG. 3B.

Referring now to FIG. 3C, there is a provide an example implementation of a therapy session (385, FIG. 3B) wherein multiple modes of operation are provided. In this example, the three modes of operation are (1) a continuous passive motion ("CPM") therapy mode of operation; (2) a volitional mode of operation; and (3) a BCI mode of operation.

The therapy session (385) shown in FIG. 3C commences at 386 wherein a mode of operation is selected. The mode of operation may be selected automatically as programmed in the rehabilitation system, for example, wherein the rehabilitation system may be programmed to cycle through various modes of operation in a therapy session. Alternatively or additionally, the mode of operation may be selected by the user, for example, by the patient or clinician using a computer user interface to make an input that selects the mode of operation to be performed.

If at (386) the CPM mode of operation is selected, the process proceeds to 387 wherein therapy is performed under a CPM mode. In a CPM mode, the orthosis device 106, for example, may operate to perform, with no volitional movement required on the part of the patient, multiple repetitions of an exercise (e.g., a hand exercise in the FIG. 1A example) in multiple sets, which serves to "work" the body part as part of a rehabilitation regimen.

If at (386) the volitional mode of operation is selected, the process proceeds to 388 wherein therapy is performed under what may be referred to as a volitional mode of operation. In a volitional mode of operation, for example, the patient may be cued by a visual instruction for example to move the impaired body part. The system may monitor the subject's response, for example, to monitor if the cued action has commenced and is continuing to completion, and if the system detects that the subject is unable to commence or complete the exercise, then the orthosis device 106 may take over and assist the subject in accomplishing the exercise. By way of example, if the system detects that the subject has not commenced the exercise within three (3) seconds of a cue to perform the exercise, then the system may be triggered to cause the orthosis device 106 to assist in performing the exercise. In addition, if the patient does start the exercise but is not able to perform the exercise to a desired degree (for example, in a hand extension exercise, the subject is unable to extend his or her fingers in a programmed amount), the system after allowing the subject sufficient time to reach the desired goal on his or her own may then cause the orthosis device 106 to assist in performing the exercise to the desired degree.

If at (386) the BCI mode of operation is selected, the process proceeds to 389 wherein therapy is performed under a BCI mode of operation. In this case the system may operate as described previously in a BCI mode of operation wherein intentions of the subject are determined and the orthosis device 106 operates accordingly.

After a therapy session has been completed in one of the modes of operation, at 390 it is determined whether the therapy session is complete or not. If complete, the therapy session ends. If not complete, the therapy session process may then proceed back to a selection of a next mode of operation at 386, wherein the process may continue under the same or a different mode of operation.

FIGS. 4-8 show more detail of the orthosis device (right hand version) 206 shown in FIGS. 2A-2B. In particular, FIGS. 4A-46 are diagrams of the entire orthosis device 206, with FIG. 4A being a perspective view, FIG. 4B being a side view, FIG. 4C being a distal end-on view, FIG. 4D being a top-side view, FIG. 4E (and FIG. 4G) being exploded views showing individual components and assemblies of the orthosis device 206, and FIG. 4F being a perspective view of an upper shell 445 of the orthosis device's main housing structure 124. FIGS. 5A-5F are diagrams of the orthosis device 106, 206 without a thumb stay assembly 134, 234, with FIG. 5A being a being a side view, FIG. 5B being a distal end-on view, FIG. 5C being a top-side view, FIG. 5D (and FIG. 5F) being exploded views showing individual components and assemblies, and FIG. 5E being a perspective view of the flexible intermediate structure 128. FIGS. 6A-6H are diagrams of the connecting and FSM assembly 130, with FIG. 6A being a perspective view, FIG. 6B being an exploded view thereof showing its individual parts, FIG. 6C being perspective view of the assembly 130 without its upper shell 460 and with its components shown as transparent for clarity, FIG. 6D being another perspective view of the assembly 130 without its upper shell 460, and FIGS. 6E-6H being diagrams to illustrate the operation of the assembly 130 and similar such assemblies. FIGS. 7A-7B are diagrams of the finger stay component 122, with FIG. 7AA being a perspective view thereof, and FIG. 6B being an exploded view thereof showing its individual parts. FIG. 8 is a diagram of a portion of the right thumb stay assembly 234, showing only its exposed portion when connected to the rest of an orthosis device.

Generally, the orthosis device 206 may be made of durable, lightweight materials (e.g., plastic for rigid parts and rubber or similar materials for flexible parts), and may be constructed using techniques such as factory-based machining or injection molding, factory-based or on-site 3D printing techniques, and/or other suitable manufacturing techniques.

Figure 4A:
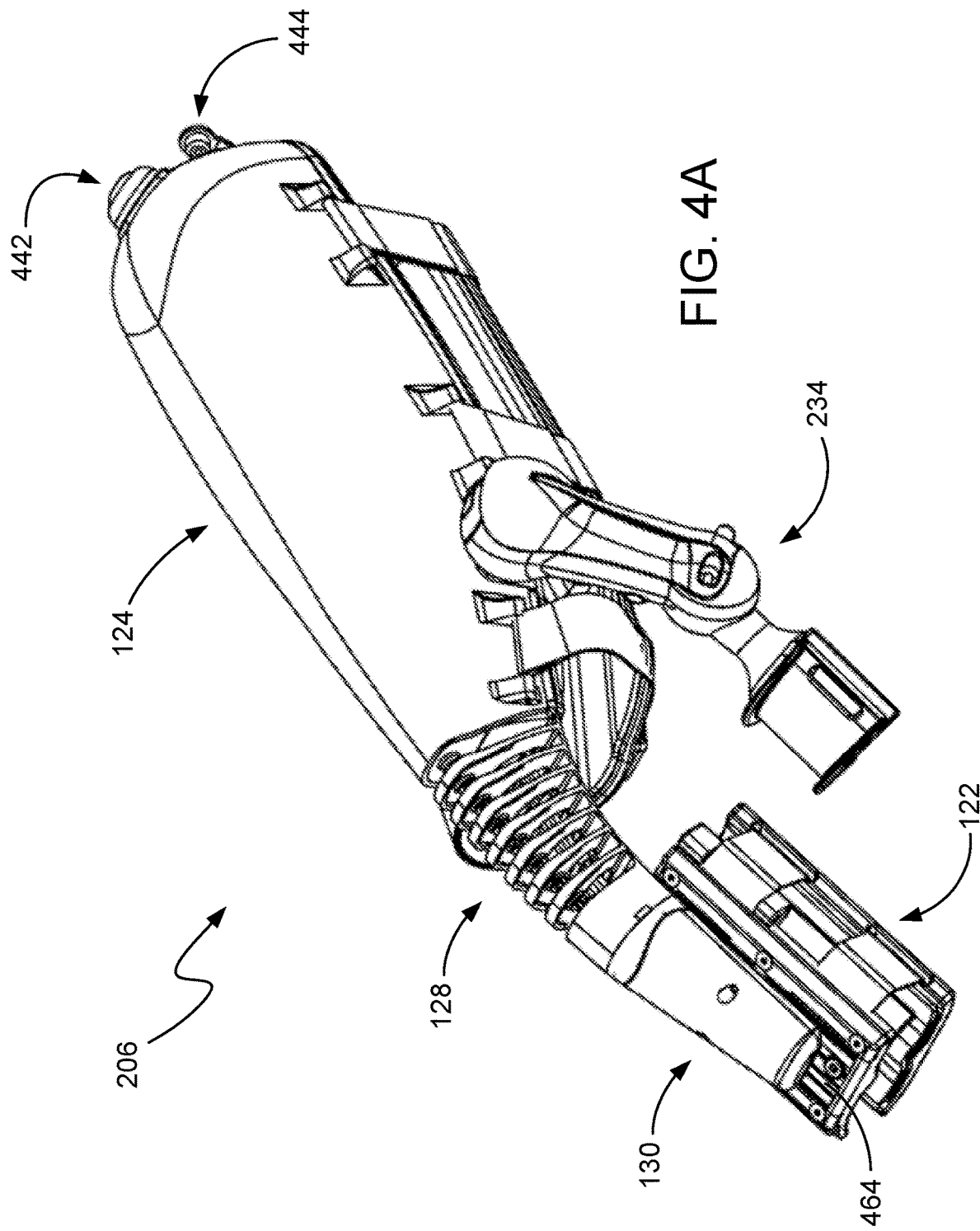
FIGS. 4A-4G are diagrams illustrating detail of an embodiment of an orthosis device which may be used in the rehabilitation system of FIG. 1A.

Turning first to FIG. 4A, the orthosis device 206 is illustrated, and includes the main housing structure 124, flexible intermediate structure 128, connecting/FSM assembly 130, finger stay assembly 122, and right thumb stay assembly 234 configured and designed as described previously in connection with FIGS. 1A, 1D and 2A-2B. Also shown in FIG. 4A is its push button power switch 442 provided at a proximal/top end location on the main housing structure 124, which switch 442 operates to activate power in the orthosis device 206 to operate its electronics and electric motor components. In addition, a battery charging port 444 is also provided at a proximal end location of the main housing structure 124, near to and just below the power switch 442 in this example implementation.

Figure 4B:
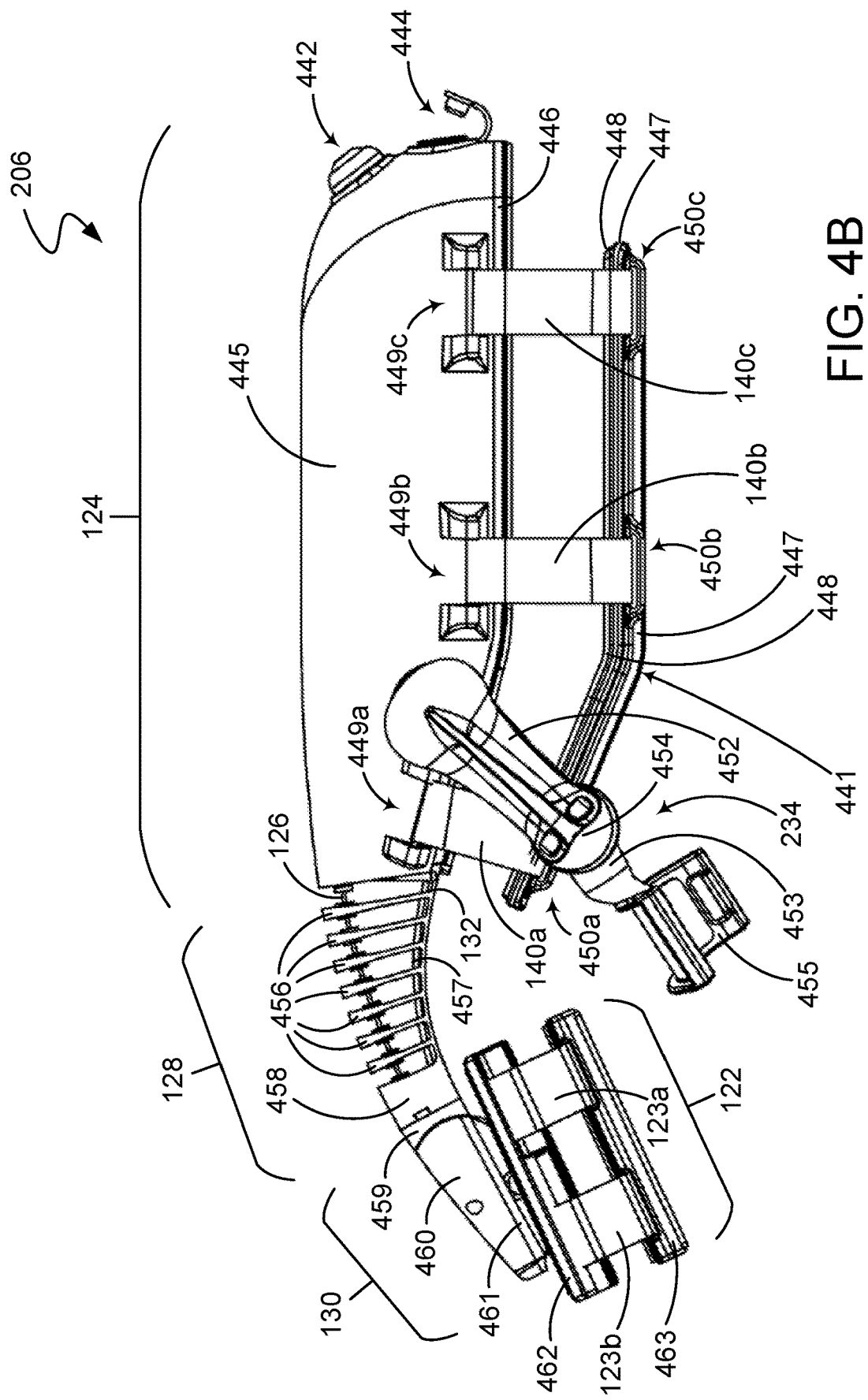
Figure 4C:
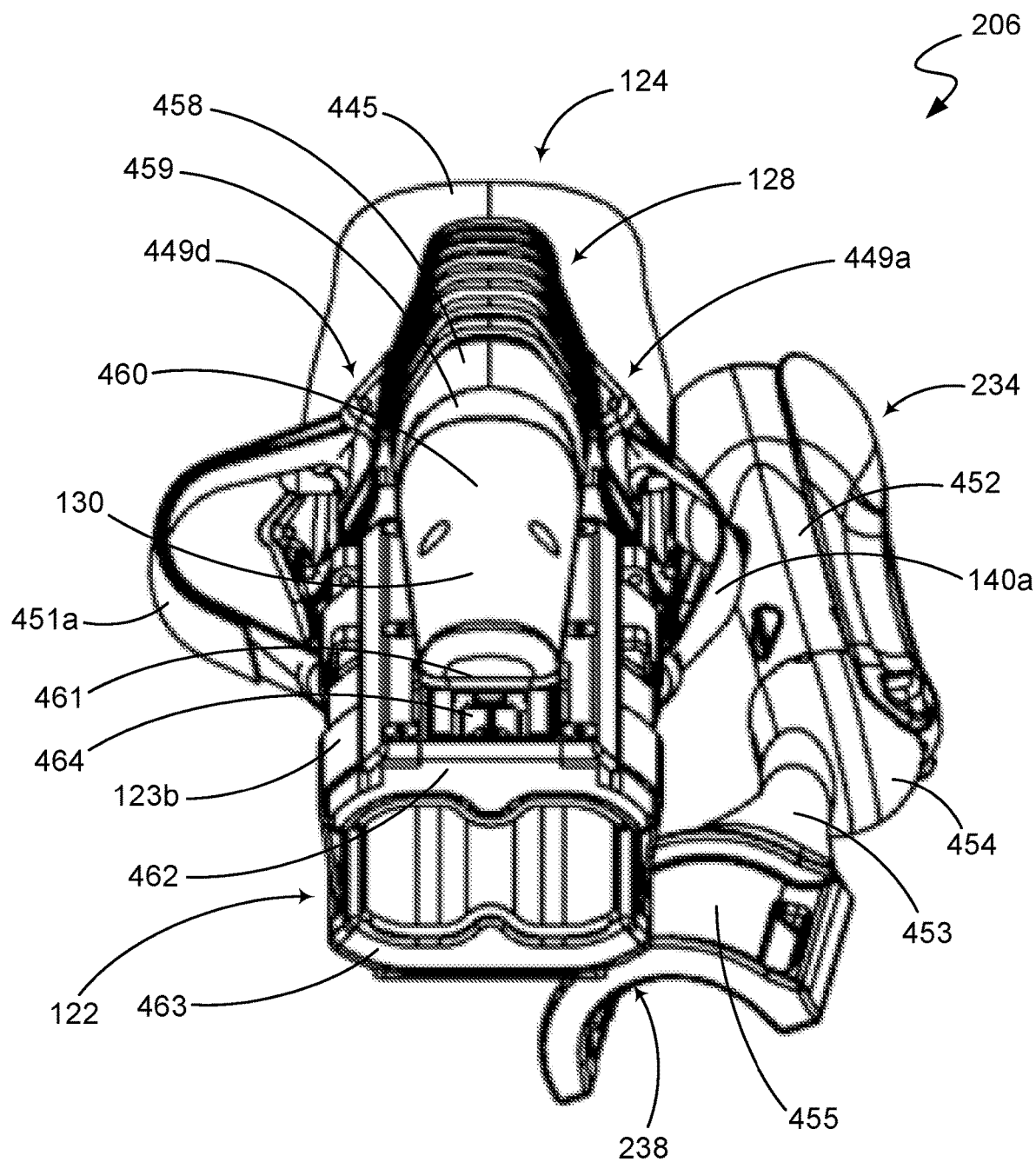
Figure 4D:
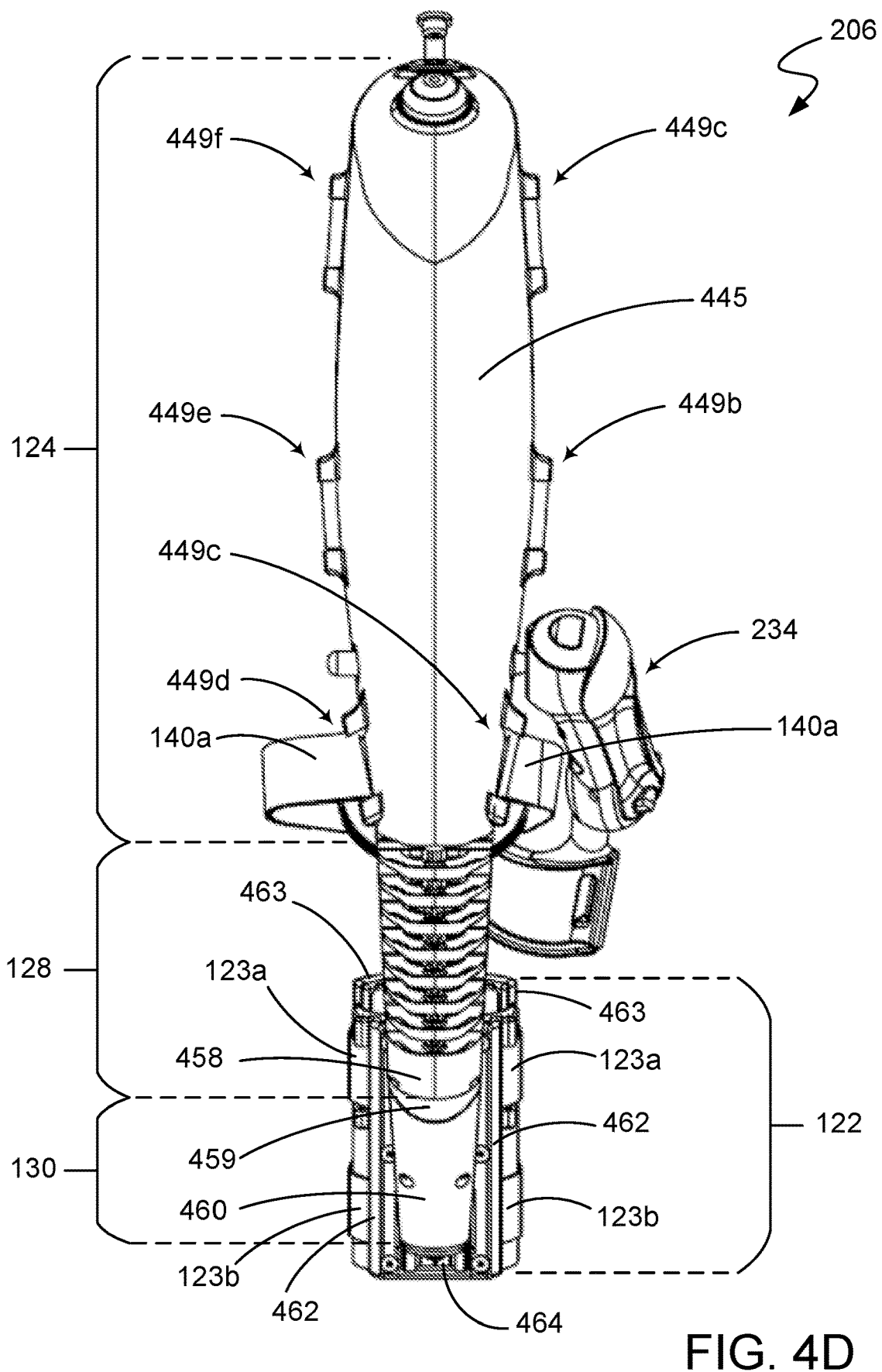
Figure 4E:
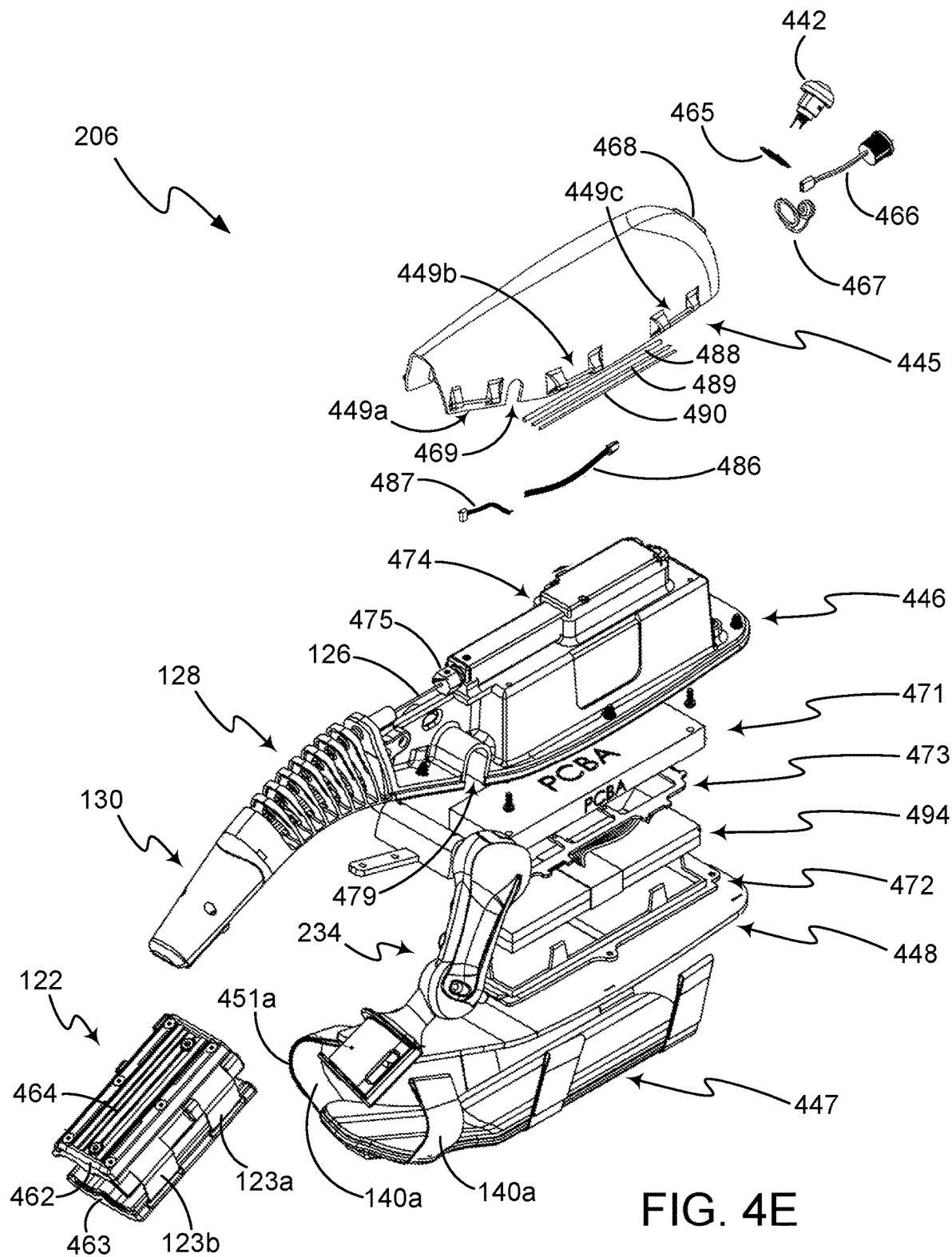

As shown in FIG. 4B and the exploded view of FIG. 4E, the main housing structure 124 includes an upper shell 445 and a lower shell 446 that form a chamber therein for a linear actuator 474 (shown in FIG. 4E). The upper shell 445 and lower shell 446 may be provided with snap fit functionality around their respective outer peripheries so the two components 445, 446 may be affixed or assembled together. As a unit, the upper shell and lower 446 are designed and configured to be worn on the upper or dorsal side of a subject's forearm, as shown in FIGS. 2A-2B.

The main housing structure 124 also includes a forearm support 447 and an inner foam layer 448 applied thereto (see FIGS. 4A, 4E and 4G), which is designed and configured to be worn on a lower or ventral side of a subject's forearm. The forearm support 447 and associated foam layer 448 in this example have a width that is generally the width of a subject's arm and a length generally the same or slightly shorter than the length of the upper and lower shells 445, 446, so that the forearm support 447 and associated foam layer 448 extend from a proximal end that is located when worn about midway between the elbow and wrist to a distal end that is located when worn in the palm of the subject's hand. The forearm support 447 may have a slight bend provided at a location 441 (see FIG. 4B) located generally at the ventral side of the subject's wrist when worn, and as such, the forearm support 447 and associated foam layer 448 serves to hold the wrist in a slightly extended orientation.

Adjustable straps 140—specifically three straps 140a, 140b, 140c in this example—are provided to connect the upper and lower shells 445, 446 with the forearm support 447 and associated foam layer 448 and to secure the subject's forearm and a portion of the subject's hand therebetween. The straps 140a, 140b, 140c, are connected to the upper shell 445 at one side of the orthosis device 206, extend downwardly therefrom to and into openings to three respective lateral strap channels 450a, 450b, 450c provided in the forearm support 447 on the same side of the orthosis device 206, extend laterally through the forearm support 447 to the opposite side of the orthosis device 206 and out of the lateral strap channels 450a, 450b, 450c of the forearm support 447, and finally extend upwardly on the opposite of the orthosis device 206 to the opposite side of the upper shell 445 where the straps are connected to the upper shell 445.

Figure 4F:
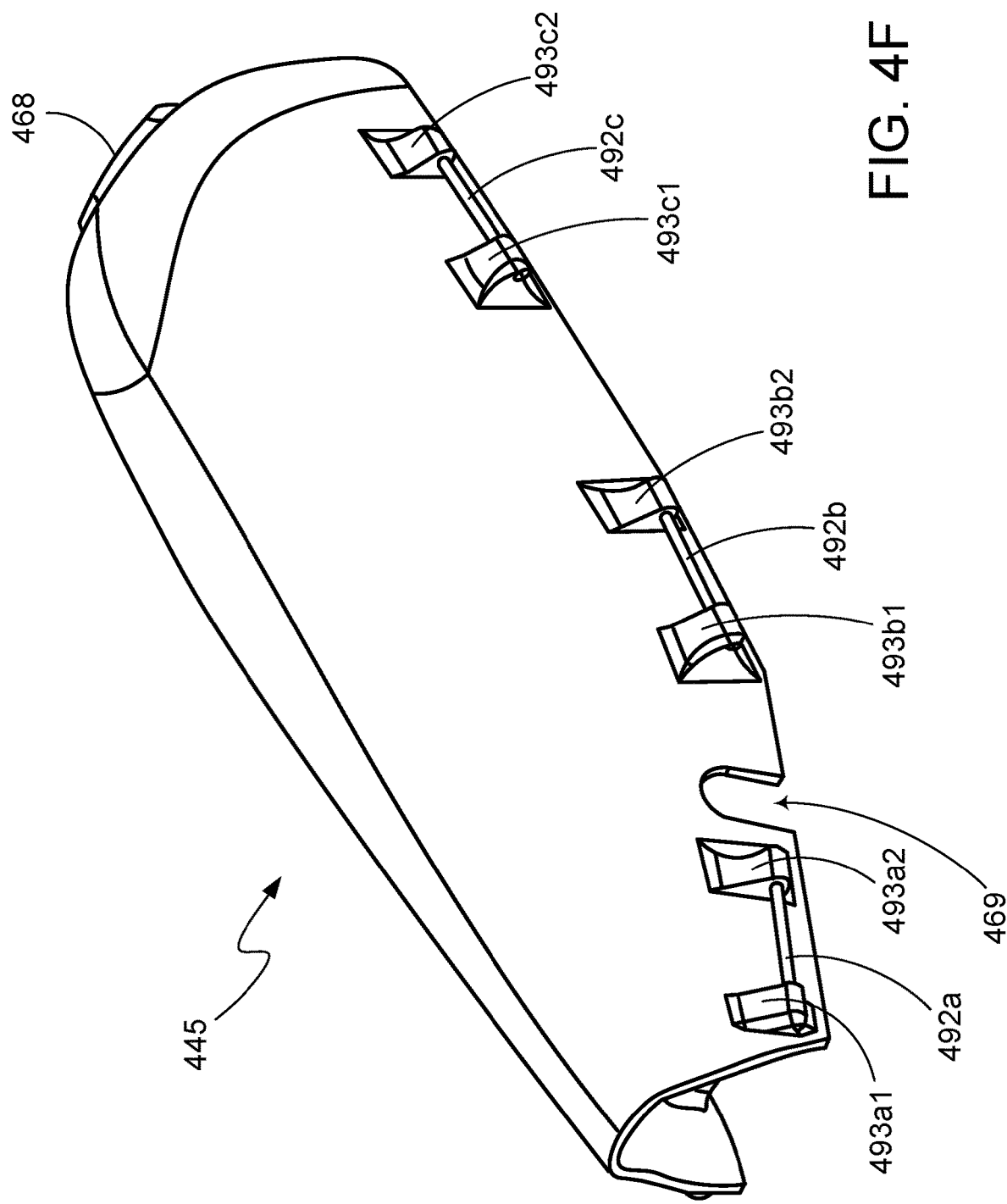

The straps 450a, 450b, 450c are in this example connected to the upper shell 445 with the aid of six strap holders 449a-449f provided on the outside sides of the upper shell 445 (see FIGS. 4B-4E). Three of the strap holders 449a-449c are provided on one side of the upper shell 445, and three of the strap holders 449d-449f are provided on the opposite side of the upper shell 445, as best seen in FIG. 4D. The strap holders may as in this example comprise dowels 492a-f and dowel holders 493a1-a2-493f1-f3, as best seen in FIG. 4F (which shows only the dowels 492a, 492b, 492c and dowel holders 493a1-a2, 493b1-b2, 493c1-c2 on one side of the upper shell 445). In the present example, one end of the straps 140a, 140b, 140c may extend through and around the three respective dowels 492a, 492b, 492c and be permanently affixed to a portion of the strap (so the straps one that side of the orthosis device 206 are not adjustable, whereas the opposite ends of the straps 140a, 140b, 140c may be extended through and around the three respective dowels 492d, 492e, 492f and be removably affixed to a portion of the strap on that side (so the straps on that side of the orthosis device 206 are adjustable). The straps 140a, 140b, 140c may be hook-and-loop type such that there are adjustable overlapping portions (e.g., overlapping portion 451a for strap 140a as shown in FIGS. 4C and 4E) on one side of the straps.

Figure 4G:
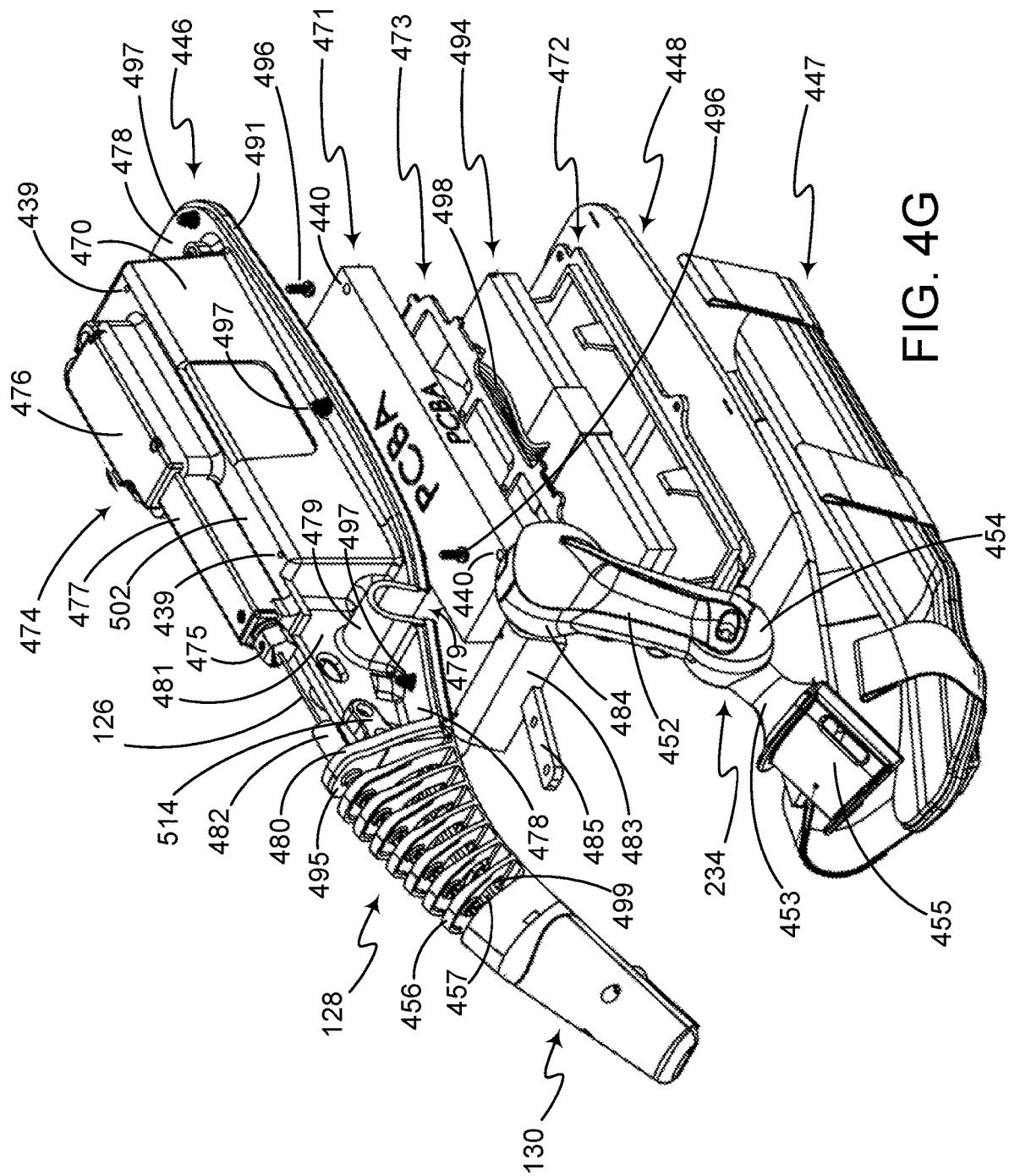

The thumb stay assembly 234, as shown in FIG. 4B, includes a proximal segment 452 whose proximal end is rotatably connected at one side of the upper shell 445, an intermediate joint 454 movably connected to a distal end of the proximal segment 452, a distal segment 453 whose proximal end is movably connected to the intermediate joint 454, and a thumb interface component 455 rotatably connected to a distal end of the distal segment 453. The proximal segment 452 of the thumb stay assembly 234, as shown in FIG. 4G, is rotatably connected at its proximal end by a rotatable joint 484 to an elongated connector portion 483 that connects the thumb stay assembly 234 to the main housing assembly's lower shell 445. Specifically, the thumb stay assembly's connector portion 483 fits into a recess formed by a laterally extending notch structure 479 that is formed in a bottom portion of the lower shell 446, as best seen in FIG. 4G (and accommodated by corresponding notches 469 provided in the lower sides of the upper shell 445, as best seen in FIGS. 4E-4F), and has a fastener tab 485 including screw holes therein extending from the connector portion 483 to affix the connector portion 483 to the lower shell 446 so the connector portion 483 is secured within and to the notch structure 479 of the lower shell 446. Owing to the rotatable joint 484, the proximal segment 452 is rotatable vis-à-vis the connector portion 484 which is affixed to the lower shell 446. The intermediate joint 454 is configured with so the distal segment 453 is able to be adjusted vis-à-vis the proximal segment 452 with two degrees of freedom. In addition, the thumb interface component 455 is configured to be rotatable vis-à-vis the distal segment 453. As such, the thumb stay assembly 234 is sufficiently adjustable to accommodate different anatomies and set the subject's thumb in a desired position, typically in an extended position, during a rehabilitation session. In addition, the design of the recess or notch structure 479 and connecting connector portion 483 of the thumb stay assembly is designed so that, for different uses, a right thumb stay assembly 234 may be used with the orthosis device or alternatively a left thumb stay assembly 134 may be used (and also a corresponding notch like notch 441 is provided in the opposite lower side of the upper shell 445 to accommodate a left thumb stay assembly like assembly 134 in FIGS. 1A and 1D being on the other side). The remaining components of the orthosis device 106/206 aside from the thumb stay assemblies 134/234 are the same in both right- and left-hand applications.

As described previously and as shown in FIG. 4B, the orthosis device 206 has a flexible intermediate member 128 with a baffle structure comprising a plurality of baffle members 456, in this example seven such members 456, each oriented generally perpendicular to a longitudinal axis of the subject's upper limb. The pushing-and-pulling wire 126 extends longitudinally through the baffle members 456 so as to compress and extend one side (that is, an upper side) of the baffle members 456 to flex and extend an upper side of the flexible intermediate member 128 and thus cause a distal end of the flexible intermediate structure 128 to be oriented more upwardly or downwardly depending upon whether the upper portion of the baffle structure is being compressed (for an upward orientation, as illustrated in FIG.

2A) or extended (for a downward orientation, as illustrated in FIG. 2B). The pushing-and-pulling wire 126 is connected on a proximal end to the linear actuator 474 (see FIG. 4E) that operates to push and pull the wire to achieve flexion and extension of the flexible intermediate member 128 and hence flexion and extension of the secured finger(s). The pushing-and-pulling wire 126 is connected on a distal end to a finger interface assembly. The finger interface assembly in this example includes two components, namely, the connecting/FSM assembly 130 that is connected at the distal end of the flexible intermediate structure 128, and the finger stay component 122 that has a longitudinally slidable connection at the underside of the connecting/FSM assembly 130 and is secured to at least one of the subject's fingers.

As described previously, the baffle structure of the flexible intermediate structure 128 also has a generally flat bottom structure 132 that is configured to attach to a bottom or hand-side of each of the individual baffle members 456, whereas an opposite or top-side of each of the individual baffle members are not so constrained and thus are free to be compressed closer together or expanded further apart by operation of the pushing-and-pulling wire 126 enlarging and/or reducing the top-side distance between the distal end of the main housing structure 124 and the proximal end of the connecting/FSM module 130. Also as shown in FIG. 4B, a force sensing resistor connector cable assembly 457 extends through each of the baffle members 456, as well as through an opening formed in end plate 495 and through opening 518 formed in distal end wall 480 (see FIGS. 4G and 5F) to connect force sensing resistors provided in the connecting/FSM assembly 130 (as described below) with electronics provided in the main housing structure 124, namely, the PCBA 471 (see FIG. 4G). The flexible intermediate structure 128 also includes a distal connecting portion 458 as shown in FIG. 4B, which is fixedly connected to a proximal end of the connecting/FSM assembly 130.

Referring still to FIG. 4B, the connecting/FSM assembly 130 includes a central support 459 that is fixedly attached to a distal end of the distal connecting portion 458 of the flexible intermediate structure 128, and two fixedly connected shells (an upper shell 460 and a lower shell 461) that is pivotally connected to the central support 459 as will be discussed later in connection with FIGS. 6B-6H. The connecting/FSM assembly 130 has a bottom surface configured to be engaged with the finger stay component 122 in a longitudinally slidable configuration, as shown in FIGS. 6B-6H and 7B, which will be described below. The finger stay component 122 is provided, as shown in FIG. 4B, with an upper elongated plate-shaped finger engagement assembly 462 that in use rests above the two secured fingers and a lower elongated plate-shaped finger engagement assembly 463 that in use rests below the two secured fingers. As described previously, two adjustable straps 123*a*, 123*b* are provided with the two finger engagement assemblies 462, 463 to secure the assemblies 123*a*, 123*b* in place with the index and middle fingers, which in use are secured as a unit between the two assemblies 462, 463. Further detail of the finger stay component 122 is provided in FIGS. 7A-7B, which will be described below.

FIG. 4C provides an end-on view of the orthosis device 206 from a distal vantage point, thus showing further detail particularly of the connecting/FSM assembly 130 and the finger stay component 122 from the distal perspective. FIG. 4C also shows a portion of a low-profile sleeve 464 that is provided on an upper portion of the finger stay component 122 to engage with rail structure (not shown in FIG. 4C) in a longitudinally slidable manner. FIG. 4C also further illustrates the thumb stay assembly 234 and how it extends from the side of the main housing structure 124, and particularly further detail of the curved configuration of the thumb interface component 455 designed to provide a comfortable thumb contact portion 238 on the thumb interface component 455 to hold the thumb in a fixed and extended position during a rehabilitation session, as illustrated in FIGS. 2A-2B.

FIG. 4D provides a top-down view of the orthosis device 206 from a vantage point above the device 206. This view, among other things, illustrates further detail of the positioning of all of the six strap holders 449*a-f*, with three of the strap holders 449*a-c* being on one side of the upper shell 445 of the main housing structure 124 and the other three strap holders 449*d-f* being on the opposite side of the upper shell 445 of the main housing structure 124.

Figure 5A:
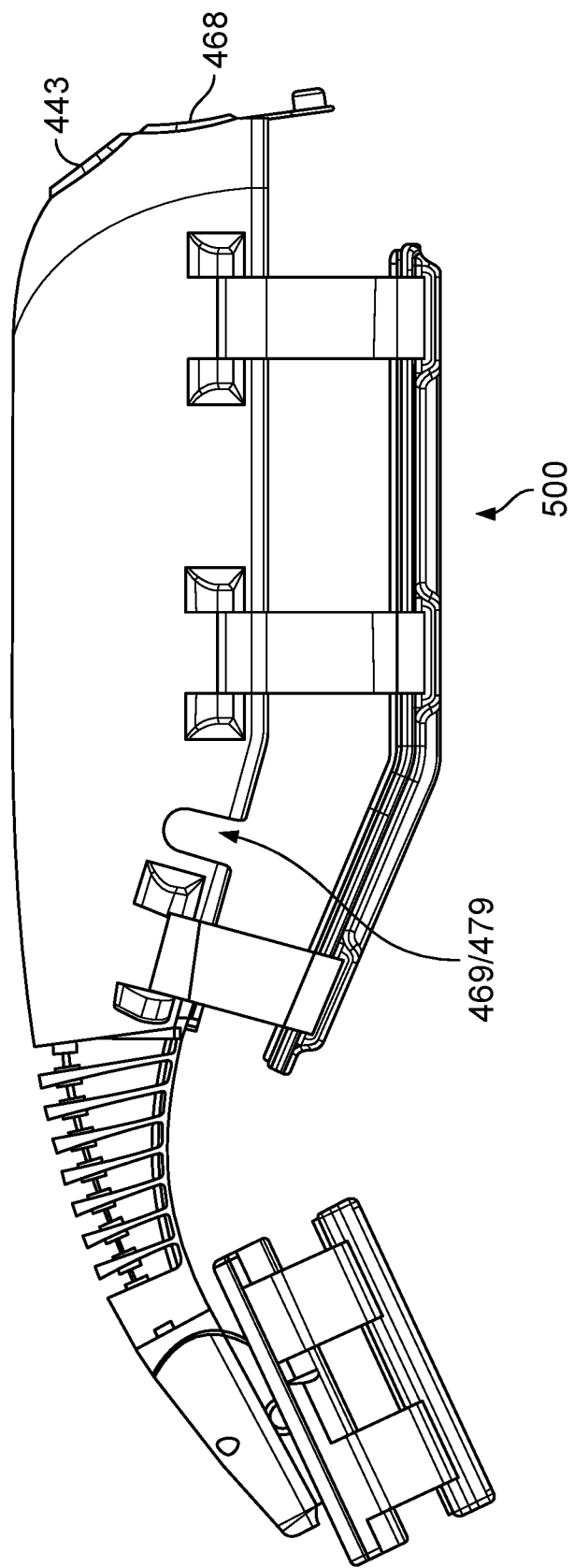
Figure 5B:
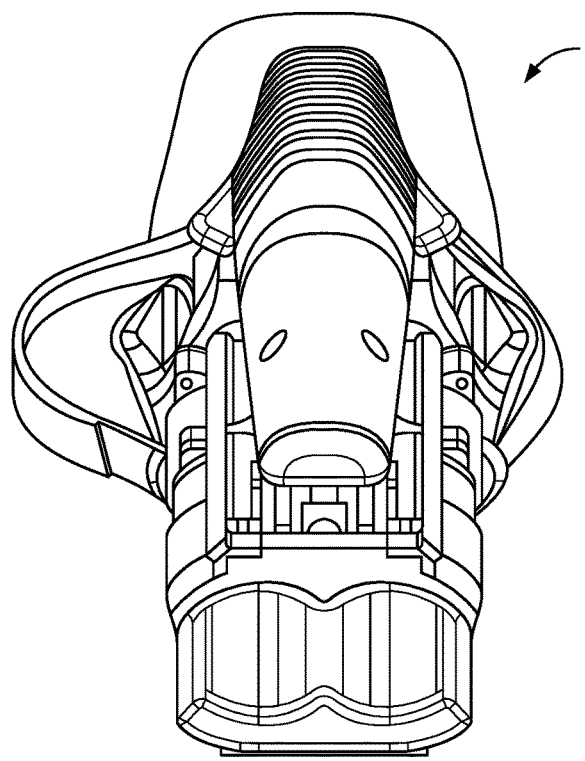
Figure 5C:
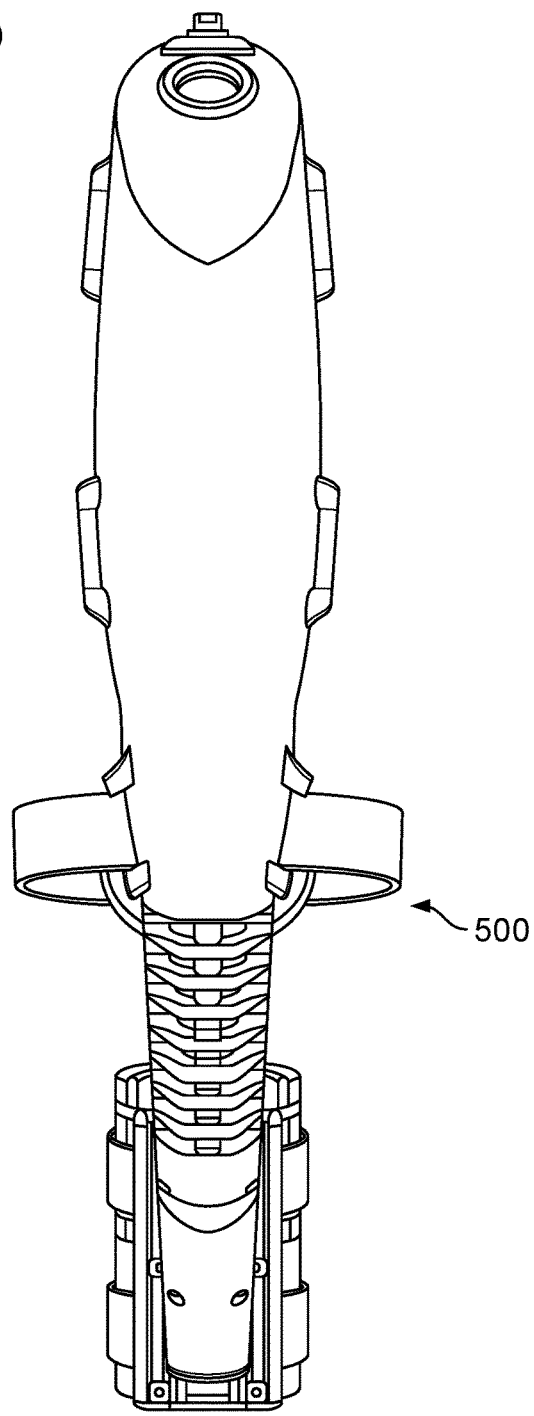

FIG. 4E is an exploded view of the orthosis device 206 showing detail of the device's components, and FIG. 4G is a second exploded view showing further detail of a portion of what's shown in FIG. 4E. Referring to FIG. 4E, a power switch gasket 465 may be provided for the push-button switch 442 to power-up the device 206. The push-button switch 442 and associated gasket 465 are assembled into and in connection with an opening 468 in the upper shell 445 (see also FIG. 4F, showing detail of the upper shell 445). Referring still to FIG. 4E, a connector jack 466 along with a barrel plug gasket 467 for charging port 444 (see FIG. 4B) is provided, and is assembled into and in connection with a second opening 443 in the upper shell 445 that is located on the proximal end of the shell 445 just below the power switch 442, as shown in FIGS. 4B and 5A. FIG. 4E also shows a power cable harness 486 and a force sensing resistor ("FSR") connection cable 487. Polyolefin heat shrink tubing 488, 489, 490 may be provided to protect various cables, as is known in the art.

As is further shown in FIG. 4E, the linear actuator 474 is assembled to be on top of the lower main housing shell 446, and as such, becomes enclosed formed between the lower shell 446 and the upper main housing shell 445 when the upper shell 445 is connected to the lower shell 446. In particular, and referring now to FIG. 4G, the lower main housing shell 446 includes an electronics housing portion 470 having an enclosed chamber that is accessible from an underside of the lower shell 446. Further detail of the lower main housing shell 446 and the linear actuator 474 is provided in FIG. 5F. As shown in FIG. 5F, the electronics housing portion 470 is formed by two generally flat side walls 526*a*, 526*b* and two generally flat end walls 526*c*, 526*d* extending upwardly from a lower plate 478 of the lower main housing shell 446 in a rectangular box-like configuration. A top wall 502 is provided on top of, and connected to, a top edge of the corresponding side and end walls 526*a-d*, thus forming an enclosure for the electronics within the walls 526*a-d* and below the top wall 502.

Referring ahead to FIG. 5F, a cradle 501 is provided on a top surface of the top wall 502. The cradle is provided for mounting the linear actuator 474 therein. Specifically, the cradle is formed by vertically extending walls positioned to corresponding generally to the periphery of a stationary linear motor portion 476 of the linear actuator 464. The linear actuator 474 includes the mentioned linear motor portion 476 that remains stationary within the cradle 501, as well as a linear actuator arm 477 that extends out of a distal side opening in the motor portion 476 of the actuator 474 and is movable linearly in piston-like fashion away from (distal direction) and toward the linear motor portion 474 (proximal direction), under the control of the stationary motor portion 476 of the linear actuator 474. In this example configuration, the motor portion 476 of the linear actuator 474 is provided with a tab-like alignment guide 504 having a vertical hole extending therethrough, which vertical hole in the alignment guide 504 is combined with a mounting alignment post extending upwardly from the top wall 502 of the electronics housing portion 470, in order to position and secure the linear actuator 474 in its proper position atop the electronics housing portion 470 of the lower shell 446.

Figure 5D:
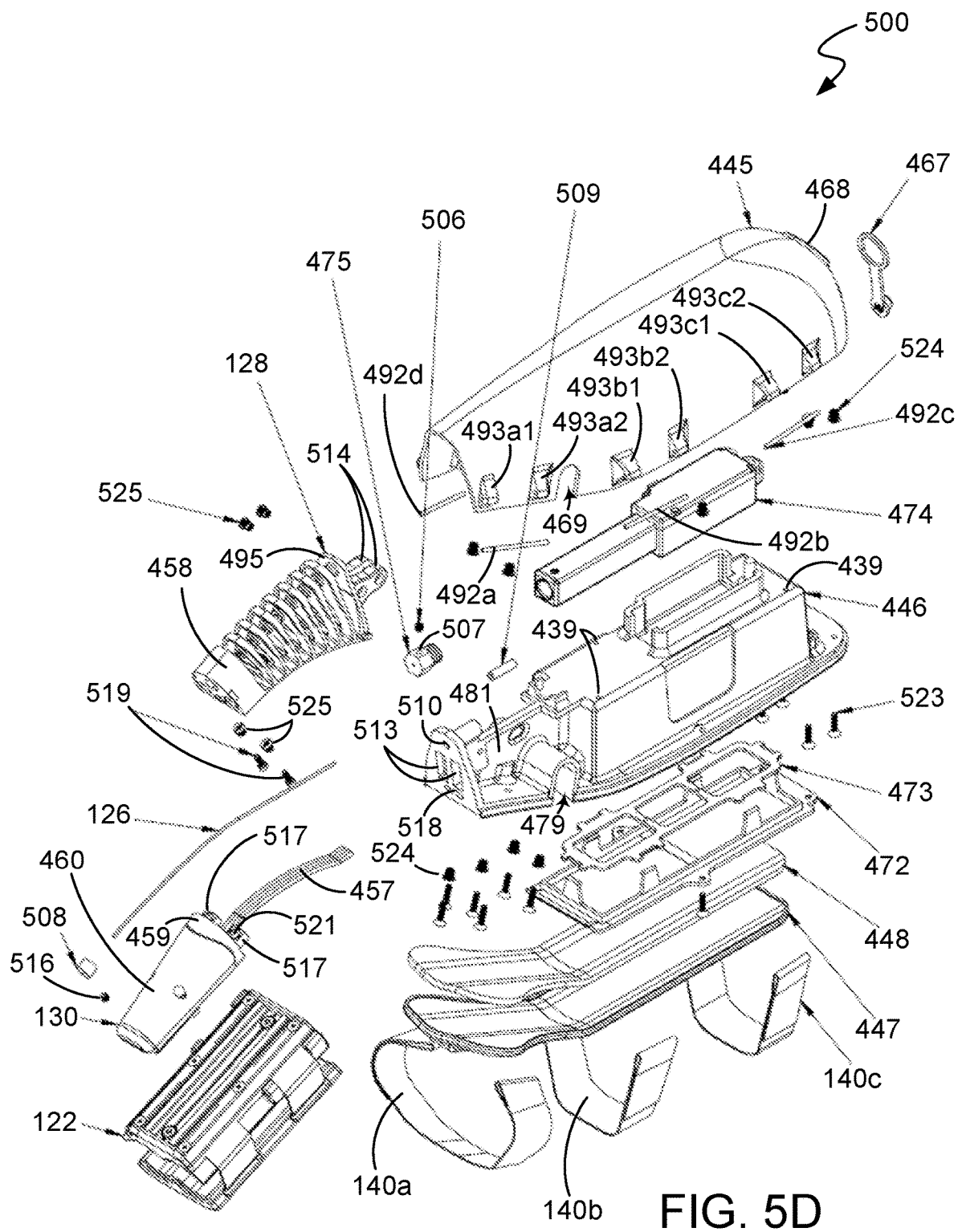

Referring now to FIGS. 4E, 4G and 5D, a connector 475 is provided at a distal end of the linear actuator arm 477 (which connector 475 is screwed into distal, internally threaded opening 505 in arm 477). The purpose of the connector 475 is to connect the arm 477 with the pushing-and-pulling wire 126, which wire 126 as described previously extends through the flexible intermediate structure 128 and is attached to the connecting/FSM assembly 130. As shown in FIG. 5D, the connector 475 may be secured to the pushing-and-pulling wire 126 by inserting the proximal end of the wire 126 into a corresponding distal opening in the connector 475, and using a set screw 506 that is inserted into a side hole 507 in the connector 475 to bear upon and secure the wire 126 into the distal hole of the connector 475. At its distal end, the pushing-and-pulling wire 126 is fixedly connected to a wire collar 508, which in turn is fixedly connected to the central support 459 of the connecting/FSM assembly 130. The connection of the wire 126 to the wire collar 508 may be accomplished with a set screw 516 that is inserted into a side hole in the wire collar 508 to bear upon and secure the wire 126 therein.

Within the chamber of the electronics housing portion 470 is provided a printed circuit board assembly ("PCBA") 471 and battery pack 494 in a sandwiched configuration. Specifically, the PCBA 471 and the battery pack 494 have roughly the same shape configuration (generally a flattened rectangular box, wherein the peripheries correspond generally with the rectangular shape of the chamber provided in the electronics housing portion 470 of the lower shell 446. Such a configuration is important in providing a form factor for the orthosis device 206 that makes the device comfortably and easily wearable on the forearm of the subject in a fully portable manner.

The PCBA 471 may be secured to an inside surface of the top wall 502 by any suitable fastening means such as screws 496 (see FIG. 4G) that are extended through corresponding screw holes 440 in the PCBA 471 and screw holes in the top wall 502 of the electronics housing portion 470. A battery retaining clamp 473, shown in FIGS. 4E and 4G and also FIG. 5D, having a generally rectangular configuration (corresponding generally in size to the size of the chamber of the electronics housing portion 470) is provided within the chamber of the electronics housing portion 470 sandwiched between the PCBA 471 and the battery pack 494, and as such, abuts an underside surface of the PCBA 471 and a top surface of the battery pack 494. The retaining clamp may have openings formed therein as shown, thus enabling electrical connection via wiring harness 498 to be made between the PCBA 471 and the battery pack 494. Finally, a battery cover/holder 472 also having a generally rectangular configuration (corresponding generally in size to the size of the chamber of the electronics housing portion 470) is removably affixed at the bottom of the electronics housing portion 470. The battery cover/holder 472 may be secured to the underside of the lower main housing shell 446 by any suitable fastening means such as screws 523 that may be affixed to corresponding thread inserts 524 (see FIGS. 5G and 5F).

Referring to FIG. 4G and FIG. 5F, a distal end wall 480 is integrally formed with the lower main housing shell 446 and provides a distal connecting structure for fixedly connecting the main housing structure 124 with the flexible intermediate structure 128. The distal end wall 480 is in this case a generally vertically configured wall structure that is provided at a location that is spaced away from (and distal of) the electronics housing portion 470 of the lower shell 446. Also integrally formed with the lower main housing shell 446 is a center vertically and longitudinally extending support wall 481 that extends from a proximal surface of the distal end wall 480 and a distal outside surface of the electronics housing portion 470 (specifically, a distal surface of the end wall 526*c* of the electronics housing portion 470). Referring specifically to FIG. 5F, the distal end wall 480 has a small circular opening formed therethrough at an upper portion of the wall 480, to accommodate the pushing-and-pulling wire 126 (see FIG. 4G) extending therethrough. Additionally, a tubular wire guide 482 may be affixed longitudinally to a proximal side surface of the distal end wall 480 and having its lumen aligned with the wire opening 510 in the distal end wall 480. A low friction tubular wire guide 509 (see FIG. 5D) may be provided within the lumen of the tubular wire guide 482 to reduce or eliminate any friction that may be encountered in pushing and pulling with the pushing-and-pulling wire 126.

Figure 5E:
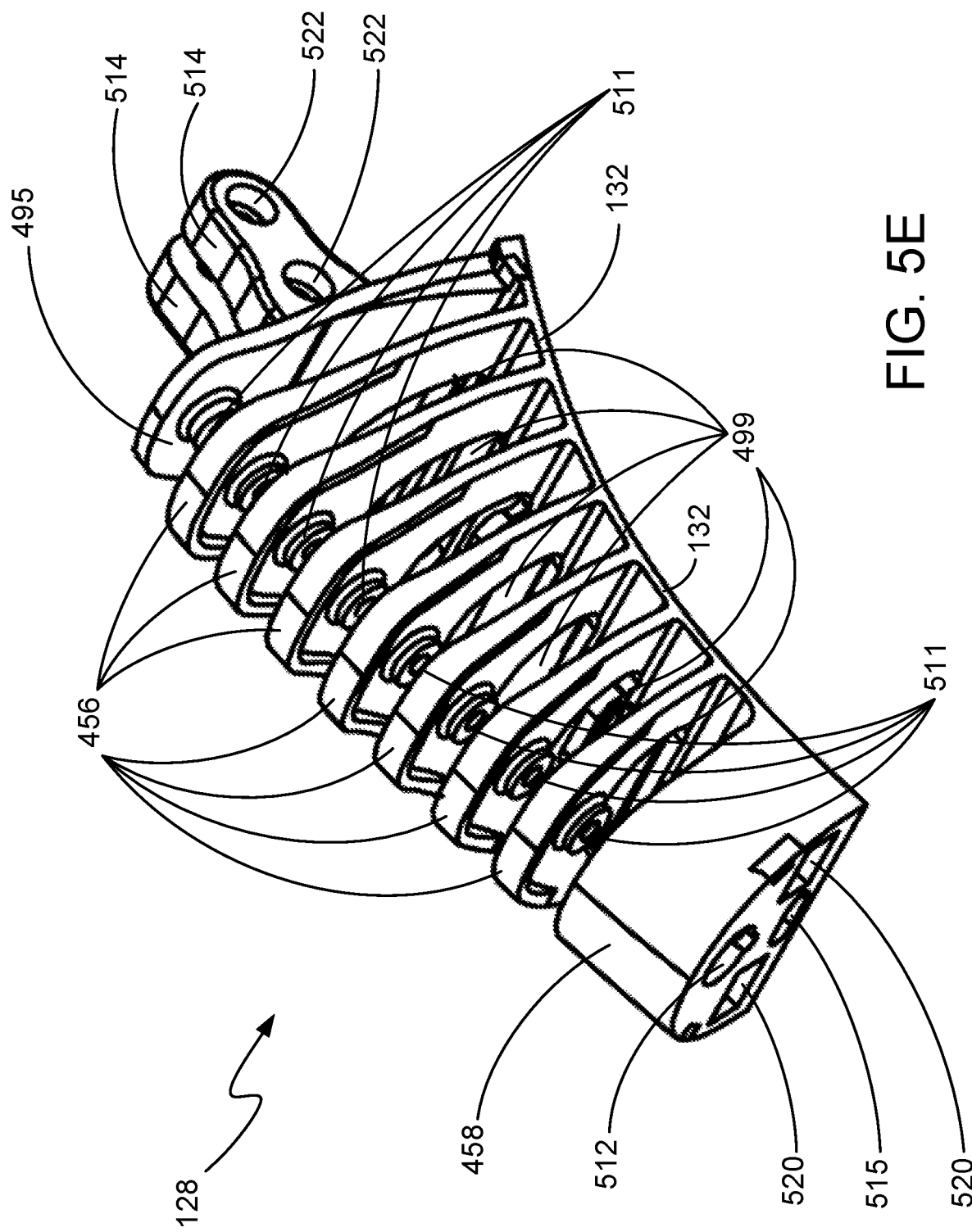

Still referring to FIG. 4G, it is shown that the flexible intermediate structure 128 has a proximal vertical end plate 495 which is sized and configured so that its proximal surface is mated with the distal surface of the distal end wall 480 of the lower main housing shell 446. Referring to FIGS. 5D-5F, it is seen that the proximal surface of the end plate 495 has two prongs 514 extending proximally therefrom which are received in corresponding openings 513 provided in the distal end wall 480 of the lower main housing shell 446 to fixedly secure the end plate 495 to the distal end wall 480 and as such the flexible intermediate structure 128 to the main housing structure 124. The two prongs 514 each have lateral screw holes 522 (see FIG. 5E) formed therein, as does the center support wall 481 at a location corresponding location (not shown), so that screws 519 and threads 525 may be used to secure the end plate 495 to the distal end wall 480.

To provide a comfortable fit for wearing on the dorsal side of the forearm, a forearm padding layer 491 (see FIG. 4G) is provided on an underside surface of the lower main housing shell 446. The padding layer may be sized so that its periphery corresponds generally with the periphery of the lower plate 478 of the lower shell 446, with a gap provided at the location of the notch structure 479. The forearm padding layer 491 may be secured to the underside of the lower plate 478 of the lower main housing shell 446 using a fastening mechanism 497 such as screws and corresponding nuts.

In FIG. 5E, detail of the flexible intermediate structure 128 is shown, with its seven horizontally and spaced apart baffle members 456 with connecting flat and flexible bottom structure 132 integrally formed and connected to each of the baffle members 456, proximal vertical end plate 495 (configured to connect to the distal end of the main housing structure 124), and distal connecting portion 458 (configured to connect to the proximal end of the connecting/FSM assembly 130). In FIG. 5E it is seen that each of the vertical end plate 495, baffle members 456 and distal connecting portion 458 have aligned and longitudinally extending holes or lumens 511, 512 extending therethrough to accommodate the pushing-and-pulling wire 126 that extends longitudinally therethrough. Low friction tubular members may be provided in the holes or lumens 511, 512 as shown. In addition, each of the baffle members 456, proximal end plate 495 and distal connecting portion 458 have a second set of aligned and longitudinally extending holes or lumens 499, 515 extending therethrough to accommodate a force sensing resistor connector cable assembly 457 (the assembly 457 being shown for example in FIGS. 4G and 5D.

As described previously, the central support 459 of the connecting/FSM assembly 130 is fixedly connected at its proximal end to the distal connecting portion 458 of the flexible intermediate structure 128 (see FIGS. 5D-5E). The mechanism for fixedly connecting the central support 459 to the distal connecting portion 458 may be understood with reference to FIG. 5D. In FIGS. 5D and 5E, it is seen that the central support 459 has two proximally extending prongs 517 configured to be inserted into, and mated with, two corresponding openings 520 formed in the distal facing end of the distal connecting portion 458. Each of the two prongs 517 has a vertical opening 521 formed therethrough, into which vertical opening 521 is received a set screw 525. A set screw 525 may be placed into the opening 521 in each of the two prongs 517, and then the prongs 517 may then be inserted into the openings 520 of the distal connecting portion 458. Once the prongs 517 are so inserted into the openings 520, screws 519 may be inserted through screw holes (not shown) formed through the underside of the distal connecting portion 458 and aligned with the openings 520. The screws 519 may thus be threaded into the set screws secured 525 provided within the openings 521 of the prongs 517, thereby securing the prongs 517 into the openings 520 and thus the central support 459 of the connecting/FSM assembly 130 to the distal connecting portion 458.

Turning now to FIGS. 6A-6H, detail of the structure and illustrations of the operation of the connecting/FSM assembly 130 are provided. First referring to FIGS. 6A-6B, it is shown that the assembly 130 includes a housing assembly comprising two fixedly connected shells (the upper shell 460 and the lower shell 461) and the central support 459. The housing assembly of shells 460 and 461 is generally in the form of an elongated nose structure that generally tapers going from its proximal end to its distal end. The upper shell 450 serves as a top cover for the housing assembly. The upper shell 460 may be aligned for connection with the lower shell 461 by mating a connecting structure (e.g., ridge) 623 (not shown in FIG. 6B) provided on a distal inner surface of the upper shell 460 with a corresponding connecting ridge 622 formed on a top distal end surface of the lower shell 461, and then using fasteners such as two screws 624a, 624b and corresponding two thread inserts 631a, 631b (only 631b being shown in FIG. 6B). After positioning the two shells 460, 461 in position with respect to one another, the two screws 624a, 624b may be advanced through screw holes 630a, 630b in the upper shell 460 and further through holes 625a, 625b in the lower shell 461, and threading the screws 624a, 624b with corresponding thread inserts 631a, 631b (only 631b being shown) that are positioned on the underside of the screw holes 625a, 625b of the lower shell 461, thereby fixedly connecting the upper shell 460 with the lower shell 461. (See also FIGS. 6C-6D, in addition to FIG. 6B.)

Figures 6A, 6B:
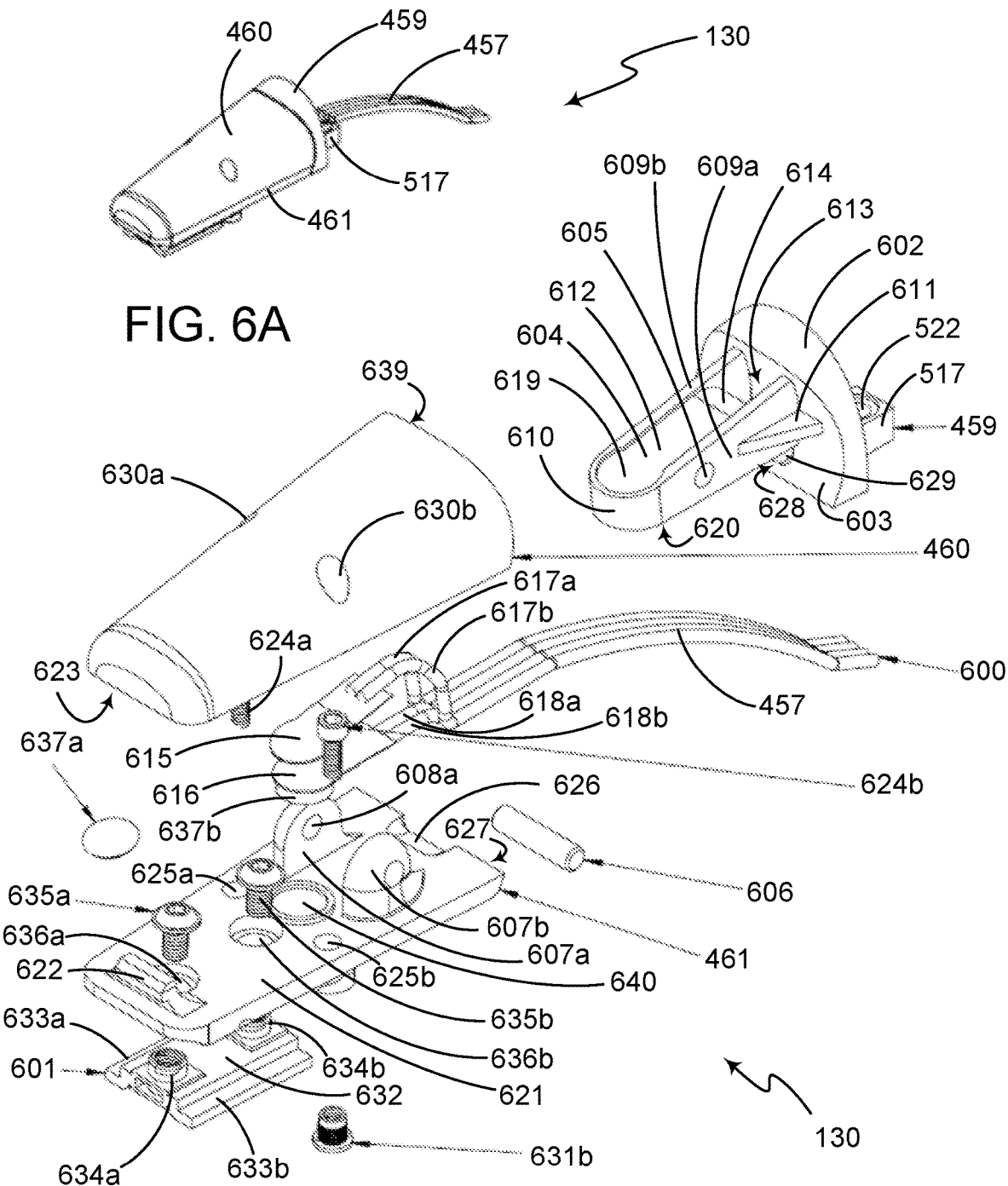
Figure 6C:
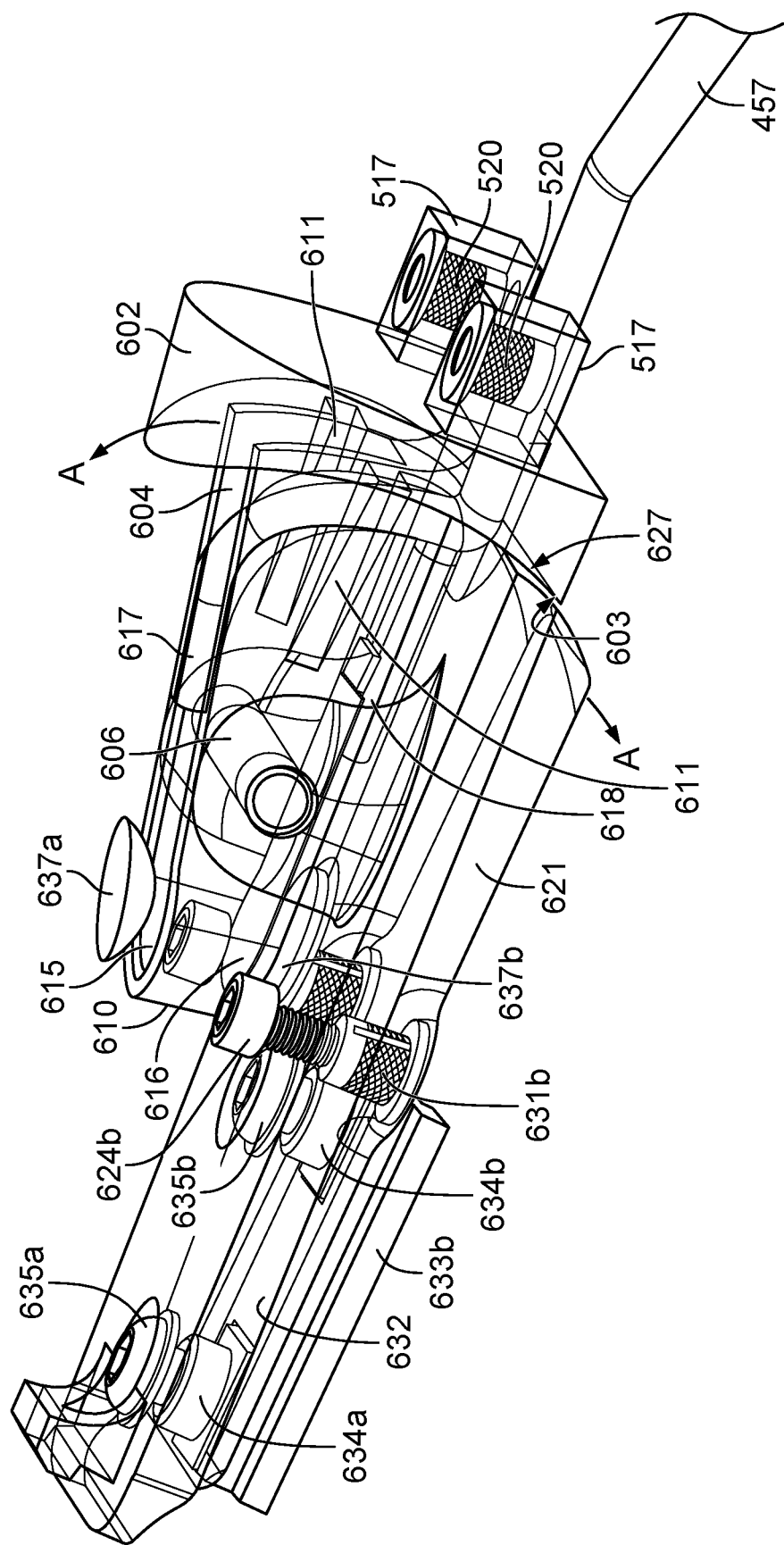
Figure 6D:
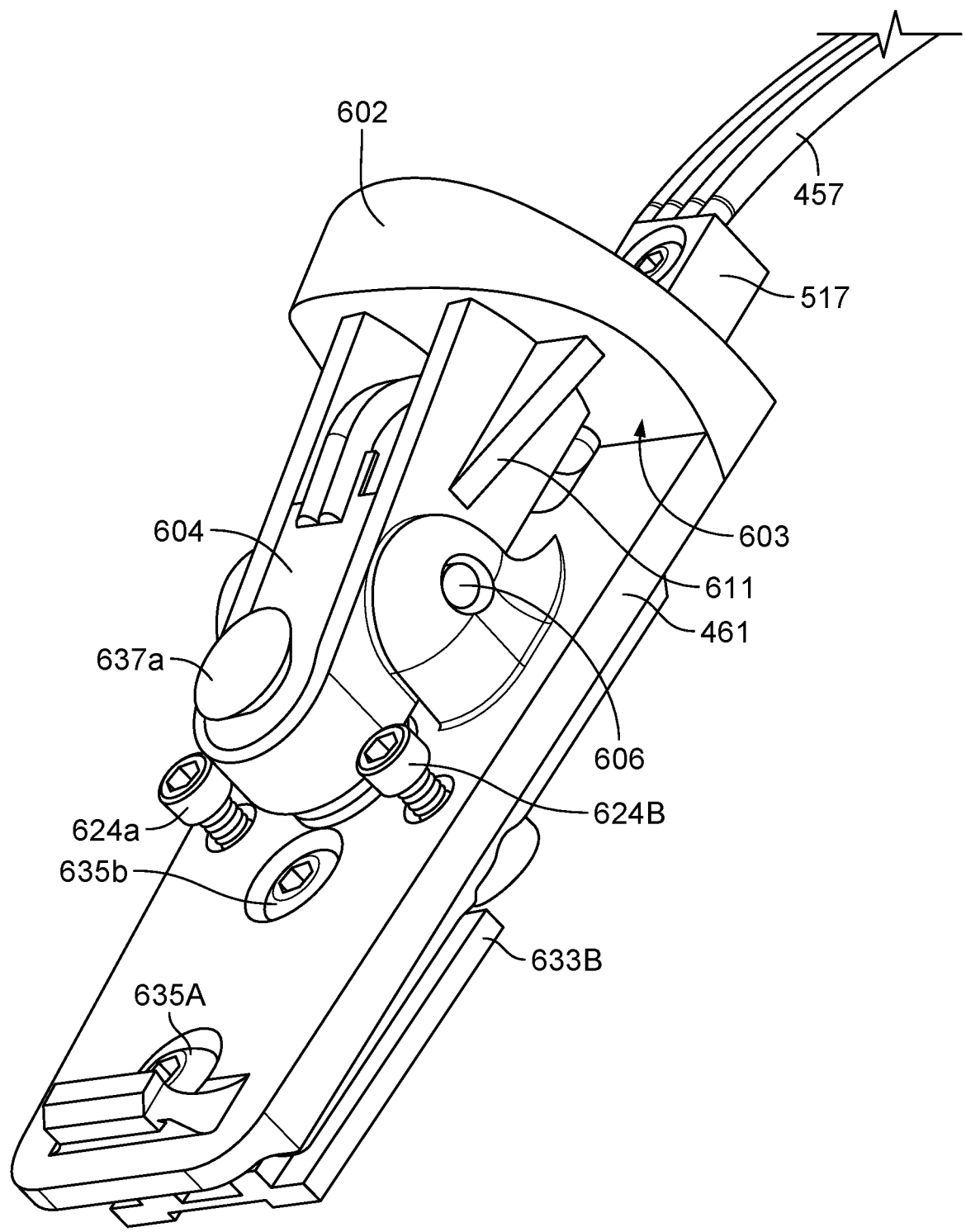

Referring still to FIG. 6B and now also FIGS. 6C-6D, the central support 459 of assembly 130 is shown to comprise a vertically oriented proximal end plate 602 and an elongate extension component 604 extending distally from a distal facing side surface 603 of the end plate 602. The elongate extension component 604 serves as a carrier of two force sensing resistors 615, 616, in a manner that will be described below. The extension component 604 comprises two vertical side walls 609a, 609b that are oriented generally parallel to one another and extend distally from, and generally perpendicular to, the distal facing surface 603 of the proximal end plate 602. The vertical side walls 609a, 609b may be integrally formed with the proximal end plate 602. At a distal end portion of the two distally extending side walls 609a, 609b, the walls 609a, 609b curve inwardly toward one other to form a curving vertical end wall 610 of the extension component 604. The extension component 604 may be reinforced by two side support structures 611, each of which is formed between the distally facing surface 603 of the proximal end plate 602 and a respective one of the side walls 609a, 609b, as shown in FIGS. 6B-6D.

As best shown in FIG. 6B, a horizontally oriented dividing wall 612 extends between and is integrally formed with the two vertical side walls 609. This dividing wall 612 separates the structure of the two force sensing resistors ("FSRs") 615, 616 from one another, or in other words, separates a first FSR 615 that may be assembled to be located above the dividing wall 612 (hereafter called the "top" FSR 615) from a second FSR 616 that may be assembled to be located below the dividing wall 612 (hereafter called the "bottom" FSR 616). The horizontally oriented dividing wall 612 extends proximally from the extension component's distal end wall 610, and extends proximally therefrom until reaching a downwardly curving portion 614 of the dividing wall 612, which downwardly curving portion 614 of dividing wall 612 begins at a location that is about two-thirds to three-quarters of the distance from the vertical end wall 610 to the proximal end plate 602.

As best seen in FIG. 6B, the top FSR 615 may be assembled to rest on top of an FSR support surface 619 of the horizontal dividing wall 612, which support surface 619 may be located at a distal portion of the horizontal dividing wall 612. The top FSR 615 specifically rests on top of this support surface 619 abutting the extension component's distal end wall 610 as well as distal portions of the extension component's side walls 609a, 609b. Two leads 617a, 617b (together referenced as leads 617 in FIG. 6C) serve the top FSR 615 and extend proximally from the top FSR 615, on top of the horizontal dividing wall 612, and eventually extend downwardly through an opening 613 provided between the dividing wall 612 and the end plate 602.

Referring again to FIG. 6B, the bottom FSR 616 may be assembled below the FSR support surface 619, in a lower chamber 620 located under the horizontal dividing wall 612. The bottom FSR 616 may abut the extension component's distal end wall 610 as well as distal portions of the extension component's side walls 609a, 609b. Two leads 618a, 618b (together referenced as leads 618 in FIG. 6C) serve the bottom FSR 616 and extend proximally therefrom, below the horizontal dividing wall 612, and eventually extend to meet the top FSR's leads 617a, 617b (that is, 617 in FIG. 6C) after such leads 617a, 617b have extended downwardly through opening 613, as shown both in FIG. 6B and FIG. 6C. The two sets of leads 617a-b, 618a-b form the connector cable assembly 457, which assembly 457 extends proximally through an opening 629 (see FIG. 6B) formed in the proximal end plate 602 of the central support 459, and from there (referring now to FIGS. 5D-5F) the cable assembly 457 extends proximally through openings 515 and 499 in and through the flexible intermediate structure 128, and further extends through the opening 518 in the lower housing shell's distal end wall 480. From there, the connector cable assembly 457 continues to extend proximally and extends inside the lower main housing shell's electronics housing 470, within which the connector cable assembly 457 is connected to the PCBA 471 (see FIG. 4E), thereby providing signals sensed by FSRs 615, 616 to the PCBA 471 for processing and control of the orthosis device 206.

As previously described, the assembly of the affixed upper and lower shells 460, 461 has a pivotable connection with the central support 459 so the two components—that is, (1) the fixed-together shells 460, 461, and (2) the central support 459—are able to rock forward distally and backward proximally with respect to one another. Referring now to FIGS. 6B-6D, the pivotable connection to provide for such rocking is implemented by the lower shell 461 having a dowel 606 provided thereon, which dowel 606 is supported by two dowel holders 607a, 607b situated on an upper surface of the lower shell 461 at a proximal portion thereof at its lateral sides. As such, the dowel 606 and dowel holders 607a, 607b reside inside a chamber formed by the upper and lower shells 460, 461, when assembled. Next, the central support 459 has two holes 605a, 605b (see FIG. 6B, which shows only one hole 605a) formed through the two vertically oriented side walls 609a, 609b of the central support's extension component 604. The dowel 606 is assembled to extend through the holes 605a, 605b, so that the fixed-together upper and lower shells 460, 461 are able to pivot up and down as a unit—and specifically about the pivot point of the dowel 606—with respect to the central support 459.

Referring to FIGS. 6B-6D, upon assembly of the central support 459 with the upper and lower shells 460, 461, a proximally facing end surface 627 of the lower shell 461 (and specifically of a bottom plate 621 of the lower shell 461) becomes located adjacent a bottom portion 628 of the distally facing side surface 603 of the central support's proximal end plate 602, and the proximally facing end surface 627 is spaced therefrom so that the lower shell 461, including its proximally facing end surface 627, is able to move up and down relative to the end plate 602 of the central support 459 when the central support 459 rocks or pivots with respect to the fixed-together upper and lower shells 460, 461. Additionally as will be best seen and appreciated from FIG. 6B, a proximally facing edge 639 of the upper shell 460 similarly faces the distally facing side surface 603 of the central support's proximal end plate 502, at a location that is generally located around the upper and side perimeter of the distally facing side surface 603, and the proximally facing edge 639 is spaced therefrom so that the upper shell 460, including its proximally facing edge 639, is able to move up and down relative to the end wall 602 when the central support 459 rocks or pivots with respect to the fixed-together upper and lower shells 460, 461.

As best seen in FIG. 6B, a cut-out 626 may be formed in a proximal edge of the lower shell 461, including in the proximally facing end surface 627, to accommodate the leads 617a-b, 618a-b (that is, leads 617, 618 as labeled in FIG. 6C) and connector cable assembly 457 extending through the opening 629 (labeled in FIG. 6B) in the central support's proximal end plate 602, upon assembly of the central support 459 with the upper and lower shells 460, 461.

Regarding the force sensing capability of the connecting/FSM assembly 130, two force sense resistor ("FSR") bumpers, buttons, or plungers 637a, 637b are utilized, as illustrated in FIGS. 6B-6D. A first FSR bumper 637a is fixedly positioned on an underside surface of the upper shell 460 in a location thereon aligned with the top FSR 615, so that the top FSR's upwardly facing surface (that is, its force sensing surface, labeled as 642 in FIGS. 6E, 6G, and 6H) comes in contact with and bears upon the first FSR bumper 637a when a distal end of the central support 459 rocks or pivots upwardly relative to the fixed-together upper and lower shells 460, 461. A second FSR bumper 637b is fixedly positioned onto and within an opening or recess 640 provided on a top surface of the lower shell 461 in a location thereon aligned with the bottom FSR 616, so that the bottom FSR's downwardly facing surface (that is, its force sensing surface, labeled as 641 in FIGS. 6E, 6G, and 6H) comes in contact with and bears upon the second FSR bumper 637b when a distal end of the central support 459 rocks or pivots downwardly relative to the fixed-together upper and lower shells 460, 461.

When the distal end of the central support 459 rocks or pivots downwardly relative to the upper and lower shells 460, 461 (as illustrated in FIG. 6G), the force sensing surface 642 of first FSR 615 may become no longer in contact with the first bumper 637a; and when the distal end of the central support 459 rocks or pivots upwardly relative to the upper and lower shells 460, 461 (as illustrated in FIG. 6H), the force sensing surface 641 of second FSR 616 may become no longer in contact with the second bumper 637b. The rocking or pivoting of the central support 459 may be limited by constraints imposed by the clearances of the two bumpers 637a, 637b from their respective FSRs 615, 616. In some embodiments such as the embodiment depicted in FIG. 6B, such clearances are minimized so that the amount of rocking or pivoting permitted is minimized but the force-sensing functioning of both FSRs is still enabled.

As illustrated by FIG. 6B, a low-profile sleeve bearing carriage 601 may be fixedly attached to an underside surface of lower shell 461, utilizing any appropriate fixation mechanism such as screws 635a, 635b that extend through screw holes 636a, 636b in the lower shell 462 and into corresponding inner threaded screw receivers 634a, 634b in the sleeve bearing carriage 601, wherein screws 635a, 635b are put in threaded engagement with the screw receivers 634a, 634b to fixedly secure the sleeve bearing carriage 601 602 to the underside of the lower shell 461. As shown in FIG. 6B, the sleeve bearing carriage 601 comprises a longitudinally extending central portion 632 having a rectangular plate-like configuration and two longitudinally extending side rails 633a, 633b provided on each lateral side of the central portion 632. As described previously, the side rails 633a, 633b provide for the longitudinally slidable engagement between the sleeve bearing carriage 601 (and hence the connecting/FSR assembly 130 to which the sleeve bearing carriage 601 is fixedly engaged) and the finger stay component 122 (see, e.g., FIG. 4A). This sliding engagement is illustrated in FIG. 6F, by arrow B.

Accordingly, the lower shell 461 of the connecting/FSM assembly 130 is connected to the finger stay component 122 that is attached thereunder in a manner that the angular orientation of the assembly 130 and the finger stay component 122 remain fixed, and yet the finger stay component 122 is permitted to freely move or slide longitudinally with respect to the lower shell 461. As previously described, the upper shell 460 is fixedly attached to the lower shell 461 and thus the upper shell's motion vis-à-vis the finger stay component 122 is the same as the motion of the lower shell 461 vis-à-vis the finger stay component 122. In other words, the upper and lower shells 460, 461 may be moved in space in a way that maintains a fixed angular relationship between the fixed-together upper and lower shells 460, 461 and the finger stay component 122. In other words, if the subject extends his or her fingers upwardly, for example, so that the fingers' distal ends pivot upwardly, then the distal ends of the fixed-together upper and lower shells 460, 461 will similarly pivot upwardly. That said, while such upward pivoting may be occurring (maintaining the fixed angular orientation between the fixed-together shells 460, 461 and the finger stay component 122), the fixed-together upper and lower shells 460, 460 may also move (that is, slide) longitudinally with respect to the finger stay component 122, which as described previously provides a comfortable wear and use of the rehabilitation system and orthosis device for the subject.

In addition, the central support 459 and the lower shell 461 are configured, as described previously, to "rock" relative to one another, owing to the pivotable connection therebetween. As such, the central support 459 is configured to "rock" relative to both the lower shell 461 and the upper shell 460. The direction of "rocking" of the upper and lower shells 460, 461 vis-à-vis the central support 459 is longitudinal with the subject's arm. The central support 459, as previously described, is also fixedly connected at its proximal end to the distal end of the flexible intermediate component 128 (see FIG. 4A), such that the central support 459 moves in a fixed relationship with the flexible intermediate component 128. As such, when the flexible intermediate component 128 is flexed so that its distal end is extended upwardly, the central support 459 is similarly extended upwardly in the manner of the central support 459 being in essence a fixed extension of the distal end of the flexible intermediate component 128.

As discussed, the central support 459 carries the two FSRs, namely, the top FSR 615 and the bottom FSR 616. The top FSR 615 has its sensing surface 642 facing upwardly toward a top bumper, button or plunger structure 637a affixed to a downwardly facing inner surface of the upper shell 460, and the bottom FSR 616 has its sensing surface 641 facing downwardly toward the bottom bumper, button or plunger structure 637b affixed to an upwardly facing inner surface of the lower shell 461. In the illustrated embodiment, the two bumpers 637a, 637b are separate from the two FSRs 615, 616 and are affixed to respective surfaces the upper and lower shells 460, 461. In particular, the top bumper 637a is affixed to the upper shell 460, and specifically, is affixed to an inner surface of the upper shell 460 so that a "dome" part of the top bumper faces downwardly toward the upward facing sensing surface 642 of the top FSR 615. The bottom bumper 637b is affixed to the lower shell 461, and specifically, is affixed within or to a circular recess/opening 640 provided in the lower shell 461, so that a "dome" part of the bottom bumper 637b faces upwardly toward the downward facing sensing surface 641 of the bottom FSR 616.

Turning now to a discussion of how these force sensing capabilities may be utilized in an orthosis device, reference may be made to FIGS. 6G-6H. As a first example illustrated in FIG. 6G, it is to be assumed that the orthosis device is not being actuated but that the patient is opening/extending his or her fingers under his or her own force, as illustrated by arrow C in FIG. 6G. Also, it is to be assumed that the orthosis device is able to be "forced" open (that is, forced into an "extended" position) by the patient's own finger opening force, which in some cases may involve activating a motor associated with orthosis device to be enabled to "follow" the volitional action of the subject. In other words, although it is the patient's own finger operating force that induces such movement in the orthosis device, the linear actuator may be "turned on" to allow the fingers to open with the patient's own force (without assist). In the case illustrated in FIG. 6G, the patient's own finger opening force causes a portion of the lower shell 461 distal of the pivot point/dowel 606, including the bottom bumper 637b affixed thereto, to be moved upwardly relative to portion of the central support that is also distal of the pivot point/dowel 606, such that the dome surface of the bottom bumper 637b contacts and applies a force against the downward facing sensing surface 641 of the bottom FSR 616. As such, the bottom FSR 616 in the scenario illustrated in FIG. 6G captures a measurement from which the patient's finger opening force may be determined.

Even in the scenario depicted in FIG. 6C, the orthosis device may also assist in opening the patient's hand, depending on the amount of force that is sensed to have been applied by the patient's own volitional movement. For example, if the patient has extended his or her fingers as far as possible on their own volition and can go no further such that the force upon sensing surface 641 diminishes or entirely ceases to be present, then the orthosis device may be programmed to take over from there to open the fingers the remainder of the way to achieve a full-range of motion experience.

Referring next to FIG. 6H, a second scenario is illustrated wherein it may be assumed that the patient is closing/flexing his or her fingers under his or her own volition and the orthosis device again is not being actuated but is able to "follow" the subject's volitional action so that the orthosis device may be "forced" into a flexed or closed position by the patient's own finger closing force. In this second scenario, the patient's own finger closing force causes a portion the upper shell 460 that is distal of the pivot point/dowel 606, and thus the top bumper 637a affixed thereto, to be "pulled" downwardly, as illustrated by arrow D in FIG. 6H, such that the domed surface of the top bumper 637a is put in contact with and applies a force against the upwardly facing sensing surface 642 of the top FSR 615. As such, the top FSR 615 enables measurement of a patient's "finger closing force."

Next and still referring to FIG. 6H, another scenario of use is illustrated wherein it may be assumed that the orthosis device is being actuated to open/extend the finger stay component 122 and hence open/extend the patient's fingers secured thereto, but the patient is not able to provide any finger opening/extension force. In this case, the flexible intermediate component 128 may be actuated so that its distal end is oriented more upwardly to move the connecting/FSM assembly's central support 459 upwardly and in a clockwise direction, as illustrated by arrow E in FIG. 6H. Because in this scenario it is assumed that the patient will be providing no help in opening the fingers, a distal portion of the upper and lower shells 460, 461 will "rock" downwardly in a counter-clockwise direction relative to the central support 459 so that the upwardly facing sensing surface 642 of the top FSR 615 comes in contact with and bears against the top bumper 637a affixed to the inner surface of the upper shell 460. In this case, the downwardly facing sensing surface 641 of the bottom FSR 616 will no longer be in contact with the bottom bumper 637b affixed to the lower shell 461. In this scenario, the presence of a force at the top FSR 615 and absence of a force at the bottom FSR 616 may thereby inform the orthosis device that the patient is providing little or no assistance in the finger opening/extension movement that is being actuated by the orthosis device.

Next and now referring back to FIG. 6G, another use scenario may be illustrated wherein it is assumed that the orthosis device is being actuated again, this time to close or flex the finger stay component 122 and hence close or flex the patient's fingers. In this scenario, the patient is not able to provide any finger closing or flexing force, but instead will be moved into a flexed position by operation of the orthosis device. In this case, the flexible intermediate component 128 is actuated so that its distal end becomes oriented more downwardly, as illustrated by arrow F in FIG. 6G, which in turn causes the connecting/FSM assembly's central support 459 to be moved downwardly in a counter-clockwise direction with reference to FIG. 6G. Because in this scenario the patient is providing no help in closing the fingers, the fixed-together upper and lower shells 460, 461—which again are in a fixed angular orientation with respect to the finger stay component 122 and hence to the patient's fingers—will then "rock" in a clockwise direction relative to the central support 459 until the downwardly facing sensing surface 641 of the bottom FSR 616 comes into contact with and bears against the bottom bumper 637*b* affixed to the lower shell 461. In addition, the upwardly facing sensing surface 642 of the top FSR 615 will then be free of contact with the top bumper 637*a* affixed to the upper shell 460. In this scenario, the presence of a force at the bottom FSR 616 and absence of a force at the top FSR 615 may thereby inform the orthosis device that the patient is not providing any assistance in the finger closing/flexing movement that is being actuated by the orthosis device.

To illustrate yet another scenario and continuing to refer to FIG. 6G, it may be assumed in this scenario that the orthosis device is being actuated to open/extend the finger stay component 122 as illustrated by arrow G, but the patient is providing a full finger opening force beyond the opening/extension force being provided by the orthosis device 206, as illustrated by arrow C. In this scenario, despite that the flexible intermediate component 128 is providing a force that would move the central support 459 upwardly and in a clockwise direction with reference to FIG. 6G, the patient is providing an even greater opening/extending force on the finger stay component 122 and thus on the upper and lower shells 460, 461 angularly affixed thereto, and as such, the patient is volitionally causing the upper and lower shells 460, 461 to move at even faster rate than the actuated central support 459 is being actuated by the orthosis device. As such in this scenario, the bottom bumper 637*b* affixed to the lower shell 461 may come in contact with and bear against the bottom FSR's downward facing sensing surface 641, and the top bumper 637*a* affixed to the upper shell 460 may then be free of and thus provide no force against the top FSR's upward facing sensing surface 642. As such, in this scenario the presence of a force sensed at the bottom FSR 616 and absence of a force sensed at the top FSR 615 may inform the orthosis device that the patient is providing all of the necessary finger opening force to achieve the desired finger opening/flexing.

Figure 9:
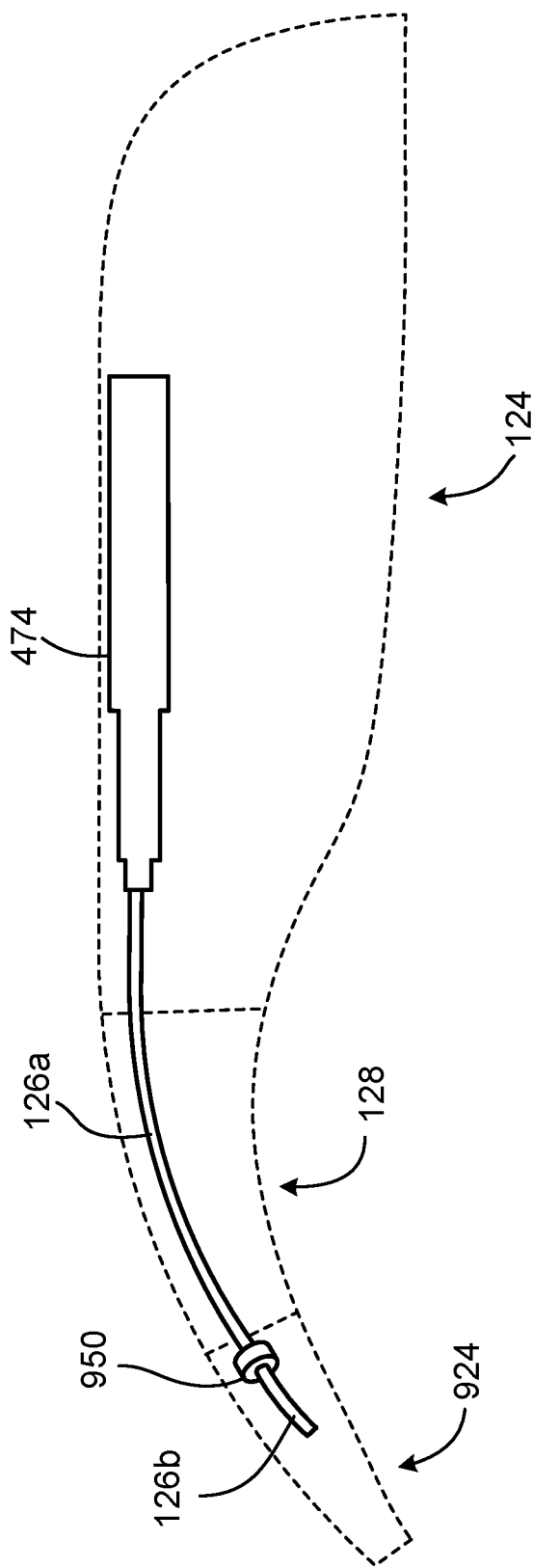
FIG. 9 is a diagram of another embodiment of an orthosis device, shown incomplete to illustrate the use of load cell force sensing.

In other implementations, load cell force sensing may be used in connection with the pushing-and-pulling wire 126, to provide for the above-described force sensing capabilities. In one implementation shown in FIG. 9, a load cell force sensor 950 in the form of a cylindrical drum-shaped structure may be provided in series with the previously described pushing-and-pulling wire 126, for example, with one side of the drum-shaped structure facing proximally and the opposite side of the drum-shaped structure facing distally. In this implementation, the pushing-and-pulling wire 126 may comprise two portions of wire, a proximal portion of wire 126*a* and a distal portion of wire 126*b*. The proximal portion of the pushing-and-pulling wire 126*a* may have its proximal end attached as discussed previously (namely, to a distal end of a linear motor 974 inside the main housing structure 124) and its distal end fixedly attached to a proximally facing side of the load cell drum shaped structure 950. The distal portion of the pushing-and-pulling wire 126*b* may have its proximal end fixedly attached to a distally facing side of the load cell drum-shaped structure 950 and its distal end fixedly attached to a force sensing module assembly 924. In FIG. 9, the positioning of the load cell force sensor 950 is shown to be associated with or contained in the force sensing module assembly 927, although it will be appreciated that the load cell force sensor 950 may be positioned more proximal, for example, within the main assembly 124. A load cell force sensor design may be selected that is capable of sensing both a tension force (exerted on the load cell force sensor, for example, by a pushing-and-pulling wire 126 being extended distally against the load cell force sensor) and a compression force (exerted on the load cell force sensor, for example, by a pushing-and-pulling wire being pulled proximally to effectively "pull" on the load cell force sensor). Accordingly, such an implementation of a force sensing module may provide functionality in connection with, for example, a volitional mode of operation as described previously, as well as other functions including functions helpful in monitoring progress of rehabilitation. The orthosis device described herein can also function in other modes of operation, in addition to the volitional mode.

Figure 7A:
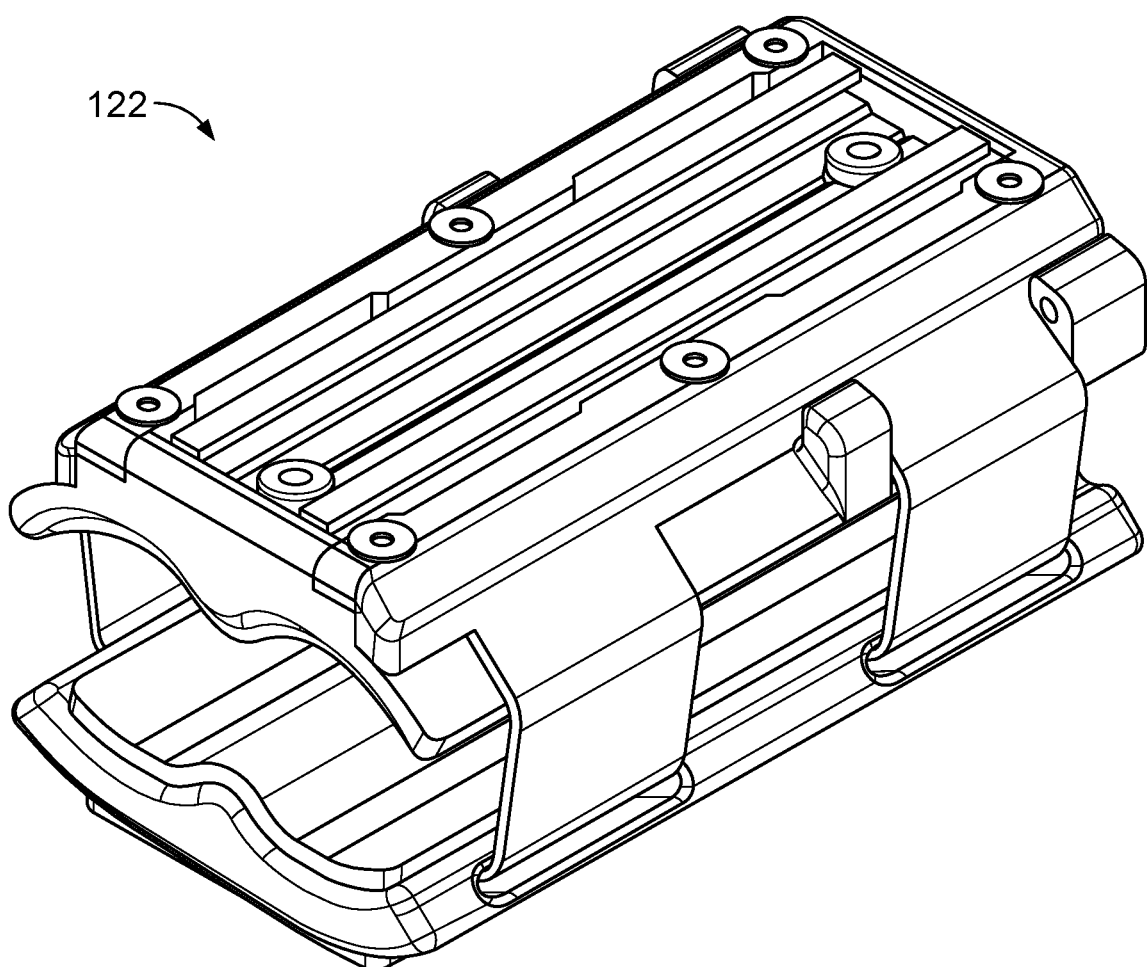
FIGS. 7A-7B are diagrams illustrating further detail of the structure of a finger stay component included in the orthosis device shown in FIGS. 4A-4G and 5A-5F.
Figure 7B:
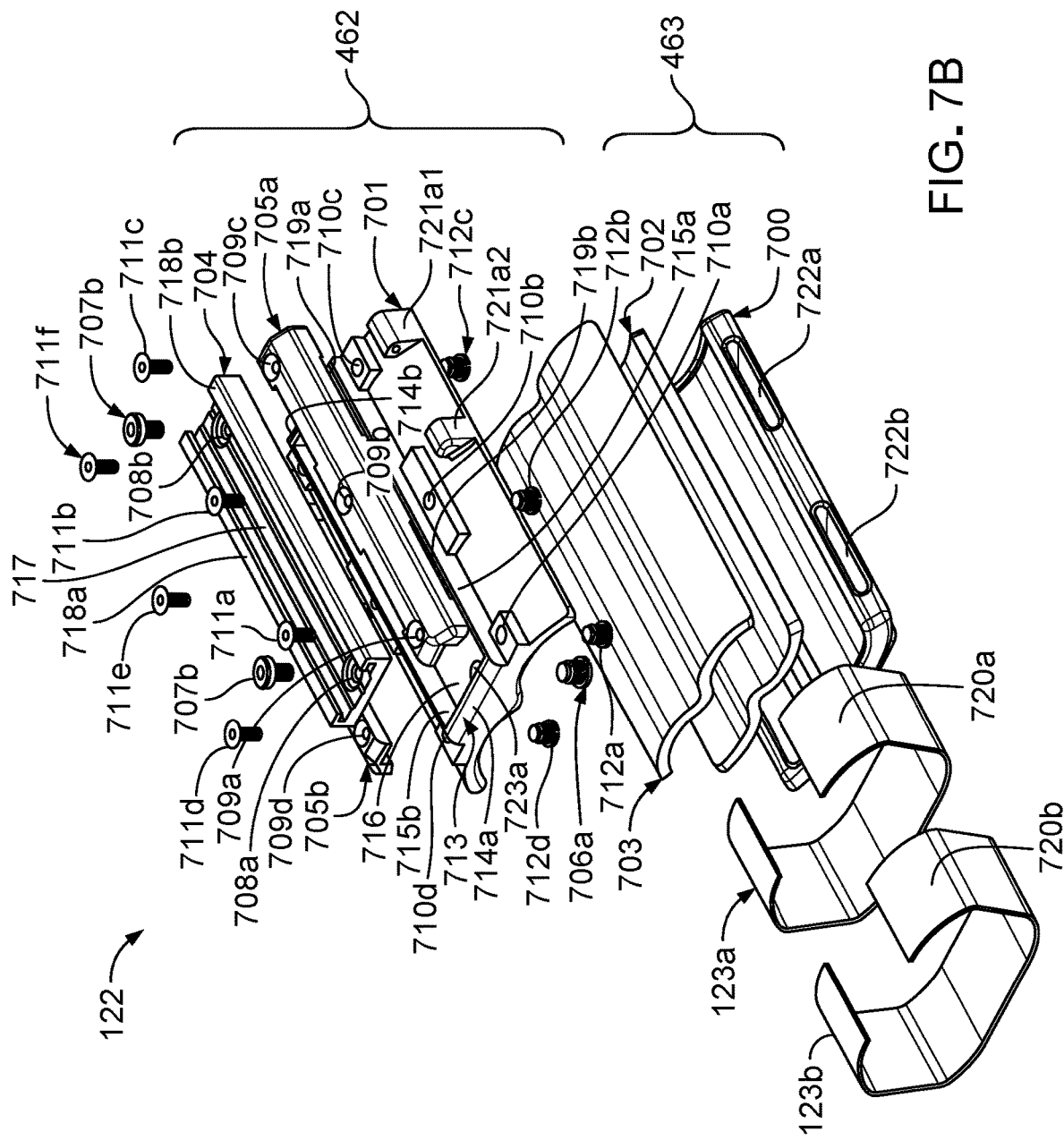

Referring now to FIGS. 7A-7B, there is shown an embodiment of a finger stay component 122 for use in orthosis devices such as devices 106, 206 described previously. The finger stay component 122 is designed to secure two adjacent fingers, for example, an index finger and an adjacent middle finger. The finger stay component 122 is designed to be usable for applications both on the right hand and on the left hand. The finger stay component 122 comprises an upper elongated plate-shaped finger engagement assembly 462 that in use rests above two secured fingers, and a lower elongated plate-shaped finger engagement assembly 463 that in use rests below the two secured fingers. Two adjustable straps 123*a*, 123*b* are provided with the two finger engagement assemblies 462, 463 to secure the assemblies 123*a*, 123*b* in place with the fingers, which in use are secured as a unit between the two assemblies 462, 463.

In the embodiment shown in FIGS. 7A-7B, the lower finger engagement assembly 463 comprises a rigid outer shell 700 (also referred to as a lower shell) and a corresponding lower finger stay pad 702 that fits within the lower rigid shell 700 and rests against a bottom surface the subject's two secured fingers when in use. The lower rigid shell 700 may be sized so that its length (a dimension running parallel with the fingers when worn) is selected so the lower shell 700 extends from a proximal location that would reside in use between the subject's knuckles and first set of joints to a distal location that would reside in use at or slightly beyond the distal tips of the fingers, as illustrated for example in FIGS. 1D and 2A-B, and further may be sized so that its width (a dimension running perpendicular with the fingers when worn) is selected so the lower shell 700 extends approximately the width of two fingers to which the shell 700 would be secured. The lower shell 700 may have a shape that roughly conforms with the two fingers to be secured, and may include as shown a longitudinal ridge running along the center of the shell 700 that would conform to the shape of two fingers, wherein the ridge would be positioned adjacent a location where the two fingers would meet. The lower shell 720 may also include two spaced-apart lumens 722*a*, 723*b* extending laterally therethrough to accommodate the two straps 123*a*, 123*b* which would be threaded therethrough. The lower finger stay pad 702 may have a length, width, and shape that is roughly the same as the lower rigid shell 700, wherein the shape roughly conforms to the fingers to be secured and includes a longitudinal ridge extending along the center of the pad 702. The lower finger stay pad 702 may comprise a foam or foam-like material that is comfortable against a subject's skin when worn.

Referring to FIG. 7B, the upper finger engagement assembly 462 comprises a rigid shell 701 (also referred to as an upper shell) and a corresponding upper finger stay pad 703 that fits within the upper rigid shell 701 and rests against a top surface of the subject's two secured fingers when in use. The upper rigid shell 701 may be sized similar to the lower rigid shell 700, namely, so that its length (a dimension running parallel with the fingers when worn) is selected so the upper shell 701 extends from a proximal location that would reside in use between the subject's knuckles and first set of joints to a distal location that would reside in use at or slightly beyond the distal tips of the fingers, as illustrated for example in FIGS. 1D and 2A-B, and further may be sized so that its width (a dimension running perpendicular with the fingers when worn) is selected so the upper shell 701 extends approximately the width of two fingers to which the shell 701 would be secured. The upper shell 701, again like the lower shell 700, may have a shape that roughly conforms with the two fingers to be secured, and may include as shown a longitudinal ridge running along the center of the shell 701 that would conform to the shape of two fingers, wherein the ridge would be positioned adjacent a location where the two fingers would meet. The upper finger stay pad 703 may have a length, width, and shape that is roughly the same as the upper rigid shell 701, wherein the shape roughly conforms to the fingers to be secured and includes a longitudinal ridge extending along the center of the pad 703. The upper finger stay pad 703 may comprise a foam or foam-like material that is comfortable against a subject's skin when worn.

As shown in FIG. 7B, the upper finger engagement assembly 462 further comprises a low-profile sleeve bearing 704 configured to mate with connecting/FSM assembly's low-profile sleeve bearing carriage 601 (see FIG. 6B), to provide for the previously described longitudinally slidable engagement between the connecting/FSM 130 and the finger stay component 122. The sleeve bearing 704 is configured, in this embodiment, to be connected on the outside of the upper rigid shell 701 (that is, on the opposite side of the shell 701 from the lower pad 702).

As is further shown in FIG. 7B to accommodate the sleeve bearing 704 thereon, the upper rigid shell 701 has a rectangular open chamber structure 713 formed on its outside surface, within which open chamber structure 713 the rectangular-shaped sleeve bearing 704 resides. The open chamber structure 713 comprises four walls 714a, 714b, 715a, 715b, in a rectangular configuration that is sized to correspond with the size of the sleeve bearing 704 so that the sleeve bearing 704 resides within the open chamber structure 713 with its sides adjacent the four side walls 714a, 714b, 715a, 715b. The four walls specifically include distal and proximal side walls 714a, 714b, and two lateral side walls 715a, 715b. An outer surface of upper rigid shell 701 includes a flat surface region 716 located within the four walls 714a, 714b, 715a, 715b, which surface region 716 serves as a bottom surface for the open chamber structure 713 against which a bottom surface of the sleeve bearing 704 rests.

Still referring to FIG. 7B, the sleeve bearing 704 may be dimensioned, as shown, to have a length that is just slightly less than the length of the upper shell 701 upon which it rests and a width that is roughly a third to a half of the width of the upper rigid shell 701. The sleeve bearing 704 may have a lateral cross-section that is the same along its entire longitudinal extent, which cross-section is generally in an upwardly facing "C" configuration, with the sleeve bearing 704 comprising generally flat rectangular bottom plate 707 and two arms 718a, 718b extending first upwardly from each of the lateral sides of the bottom plate 707 and then inwardly toward one another, thereby forming two longitudinally extending recesses within which the corresponding side rails 633a, 633b (see FIG. 6B) of the connecting/FSM assembly's sleeve bearing carriage 702 reside in longitudinally slidable engagement.

As shown in FIG. 7B, the sleeve bearing 704 may be fixedly secured to the upper rigid shell 701, within its open chamber 713, using any suitable fastening mechanism such as the socket head screws 707a, 707b and corresponding thread inserts 706a, 706b (only 706a being shown in FIG. 7B). Specifically, the screws 707a, 707b may be inserted through two screw holes 708a, 708b that extend through the sleeve bearing 704 and located at opposite longitudinal ends of the sleeve bearing 704, and further through two corresponding screw holes 708a, 708b (only 708a being shown in FIG. 7B) that extend through the upper shell 701, and engaged with the inner threads of thread inserts 706a, 706b positioned on the underside of screw holes 708a, 708b.

The upper finger engagement assembly 462 may also include two elastic clamps 705a, 705b as shown in FIG. 7B, which elastic clamps 705a, 705b may serve in part to secure the straps 123a, 123b to the upper finger engagement assembly 462. Specifically, the elastic clamps 705a, 705b may be as shown elongate in general configuration and have a cross-section that is generally "L"-shaped along its entire longitudinal extent. Each of the two elastic clamps 705a, 705b may have a length as shown that is generally about the same as the length of the sleeve bearing 704, and the elastic clamps 705a, 705b may each be designed and configured to be affixed to an outer surface of the upper rigid shell 701 alongside the sleeve bearing 704. In particular, a first elastic clamp 705a may be provided on one lateral side of the sleeve bearing 704, and a second elastic clamp 705b may be provided on the opposite lateral side of the sleeve bearing 704, as shown in FIG. 7B.

The elastic clamps 705a, 705b each includes, as part of one leg of the "L"-shaped cross section, a portion that is configured to abut against an outwardly facing surface of the upper rigid shell 701, along the entire longitudinal extent of the clamps 705a, 705b. This abutting portion of the clamps 705a, 705b includes two spaced-apart recesses 719a, 719b that form two gaps between the clamps 705a, 705b and the outer surface of the rigid shell 701, the purpose of which is to accommodate corresponding ends of the straps 123a, 123b thereunder. As such, corresponding first ends 720a, 720b of the straps 123a, 123b may be provided within and under the recesses 719a, 719b of the first clamp 705a, and corresponding opposite second ends of the straps 123a, 123a may be provided under similar recess in the second clamp 705b (these recesses in second clamp 705b not shown in FIG. 7B, but may be similar in form to the recesses 720a, 720b in first clamp 705a). The recesses 720a, 720b may be sized so that when the clamps 705a, 705b are clamped down upon the outer surface of the rigid shell 701, the clamps 705a, 705b secure both ends of both straps 123a, 123b within the recesses 705a, 705b thereof.

The clamps 705a, 705b may be secured to upper rigid shell 701 using any suitable fastener mechanism such as the six screws 711a-f and corresponding thread inserts 712a-f. Specifically, the screws 711a-f may be hex-drive flat head screws as shown that may be inserted through six screw holes 709a-f that extend through the two elastic clamps 705a, 705b (with three screws 709a-c in one clamp 705a, and three screws 709d-f in the other clamp 705b) and further through six corresponding screw holes 710a-f that extend through the upper shell 701, and engaged with the inner threads of thread inserts 712a-f positioned on the underside of screw holes 710a-f.

One of the straps—specifically proximal strap 123a—may be configured to be adjustable, in which case one end 720a of the strap 123a may not be secured under the clamp 705a, but instead may adjustably secured under and to a strap connecting structure comprising dowel holders 721a1, 721a2 and a corresponding dowel (not shown in FIG. 7B, but similar in configuration to dowels 492a-c provided in the upper main housing shell 445 shown in FIG. 4F. With this configuration, the distal strap 123b may be secured and not adjustable, wherein the proximal strap 123a may be adjustable. As such, when donning the orthosis device, a subject may slide his or her two fingers between the two finger stay pads 702, 703, from a proximal end of the pads 702, 703. The distal strap 123b may be configured so that the distal ends of the two fingers can be slid between the pads 702, 703 with a relatively snug fitting, and then when the fingers are fully extended longitudinally between the two pads 702, 703, the proximal strap 123a may be cinched down into place to ensure patient comfort by connecting the end 720a of the proximal strap 123a into the dowel-type adjustable strap connecting structure. Alternatively, both straps 123a, 123b may be configured to be non-adjustable, in which case for example the end 720a of the proximal strap 123a may be fixed under the corresponding recess 719a of the elastic clamp 705a.

Figure 7C:
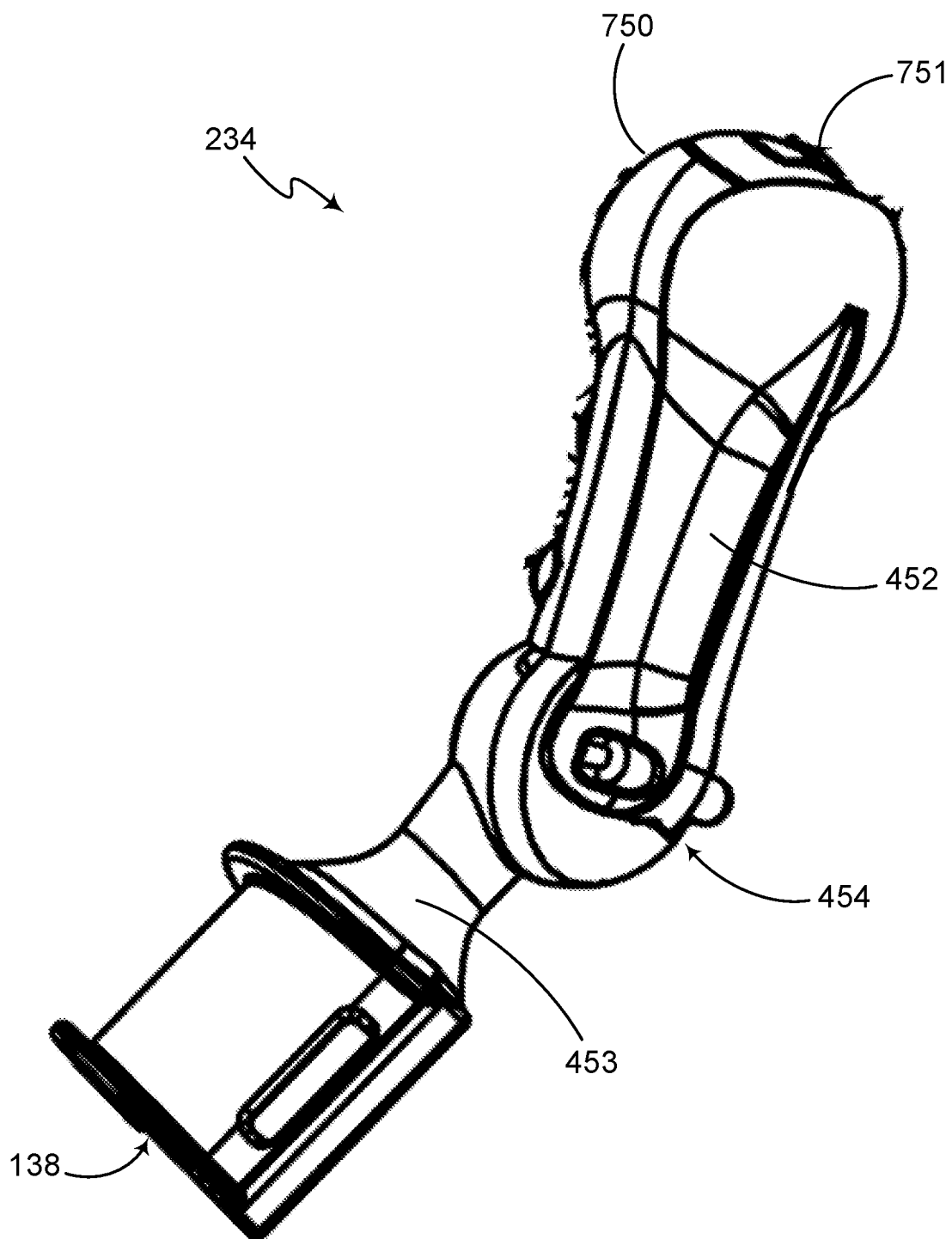
FIG. 7C is a diagram illustrating further detail of an external portion of the structure of a thumb stay component included in the orthosis device shown in FIGS. 4A-4G and 5A-5F.

Turning now to FIG. 7C, further detail of an external portion of the left-hand thumb piece 234 is illustrated. As previously described the thumb piece 234, at a proximal end, is attached to a side of the main housing structure 124 on the side where the subject's thumb would be located. The thumb piece 234 in the example of FIG. 7C extends to a thumb contact portion 138 which in use is put in contact with an inner surface of the thumb, in order to maintain the thumb in a generally extended position, as illustrated for example in FIG. 1D and FIGS. 2A-B. In this embodiment, the thumb piece 234 is adjustable manually to a position such as that shown in FIG. 1D and FIGS. 2A-2B, and once manually adjusted to that position, remains in that position, or in other words, is not in this embodiment actuated by an actuator such as a motor or the like but instead remains in the same position during use of the orthosis device in a rehabilitation session.

The thumb stay assembly 234, as shown in FIG. 7C, includes a proximal segment 452 whose proximal end is rotatably connected at one side of the upper shell 445 (see FIG. 4E), an intermediate joint 454 movably connected to a distal end of the proximal segment 452, a distal segment 453 whose proximal end is movably connected to the intermediate joint 454, and a thumb interface component 455 rotatably connected to a distal end of the distal segment 453. Additional description of these and further aspects of the thumb stay assembly shown in FIG. 7C is provided above in connection with the description of FIGS. 4G-4F. FIG. 7C further illustrates the thumb interface component 455 comprising a shoulder pivot interface, configured to allow the proximal segment 452 to be pivotably adjusted with respect to the thumb stay assembly's connector portion 483 (see FIG. 4G), and an adjustment set/release mechanism where the proximal segment 452 may be rotatably released from the connector portion 483 to adjust the angular relationship therebetween and upon adjusting to the proper angular relationship for the subject, locked into a set position.

In other implementations as one of skill in the art will appreciate, a wearable orthosis device may be provided that enables movement of additional and/or alternative body parts other than fingers of an impaired upper extremity as illustrated and described above. For example, various aspects of the above described systems and components may be configured to provide for rehabilitative movement of other body parts associated with upper and lower extremities. For example, upper extremity movement may be provided in connection with a thumb (for example, extending and flexing, and side-to-side movement of the thumb relative to the hand), a wrist (for example, extending and flexing, as well as side-to-side movement of the hand relative to the forearm), an elbow (for example, extending and flexing the lower arm relative to the upper arm), and a shoulder. In the case of wrist motion for example, a main housing structure 124 may be provided as described above that is configured to be worn on the forearm, and a body part attachment structure including force sensing components may be provided to secure the hand. In addition, in other implementations providing for finger and/or thumb rehabilitative movement, a main housing structure 124 may be provided that is configured to be worn in part or solely on the hand, with finger and/or thumb attachment structures provided.

Figure 8A:
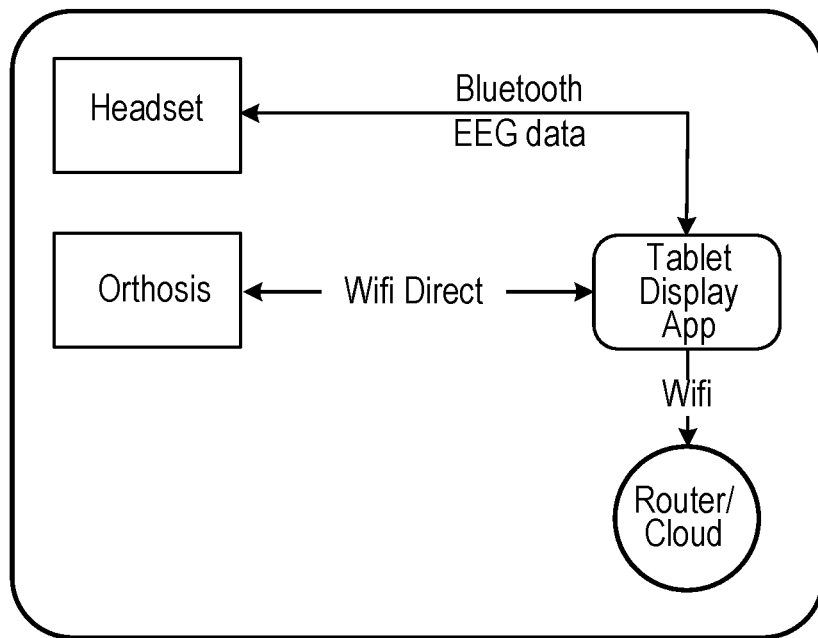
FIGS. 8A-8C are system and flow diagrams illustrating embodiments of the architecture and operation of a rehabilitation system.

Turning now to FIG. 8A, an example system architecture is provided for a rehabilitation system such as the system 100 shown in FIG. 1. Regarding communication among the components of the system 100, an application program provided in this embodiment on the Tablet computing device 110 may communicate with the EEG headset 104 through wireless communications using a protocol such as Bluetooth®, with the orthosis device 106 also through wireless communications using a protocol such as Wifi Direct, and with the router 114 also through wireless communications using a protocol such as WiFi.

The Bluetooth® connection with the EEG headset 104 may be paired only one time through a COM port in the tablet computer 110, and the COM number may be saved in the application program on the tablet computer 110. The tablet computer may also automatically connect to the EEG headset 104 through Bluetooth® wireless whenever a user opens the application program on the tablet computer 110.

The connection between the application program on the tablet computer 110 and the orthosis device 106 may be established based on the orthosis device's serial number, which may be put in the application program only one time. The application program may automatically search this serial number and then connect to the orthosis device whenever a user opens the application program.

Figure 8B:
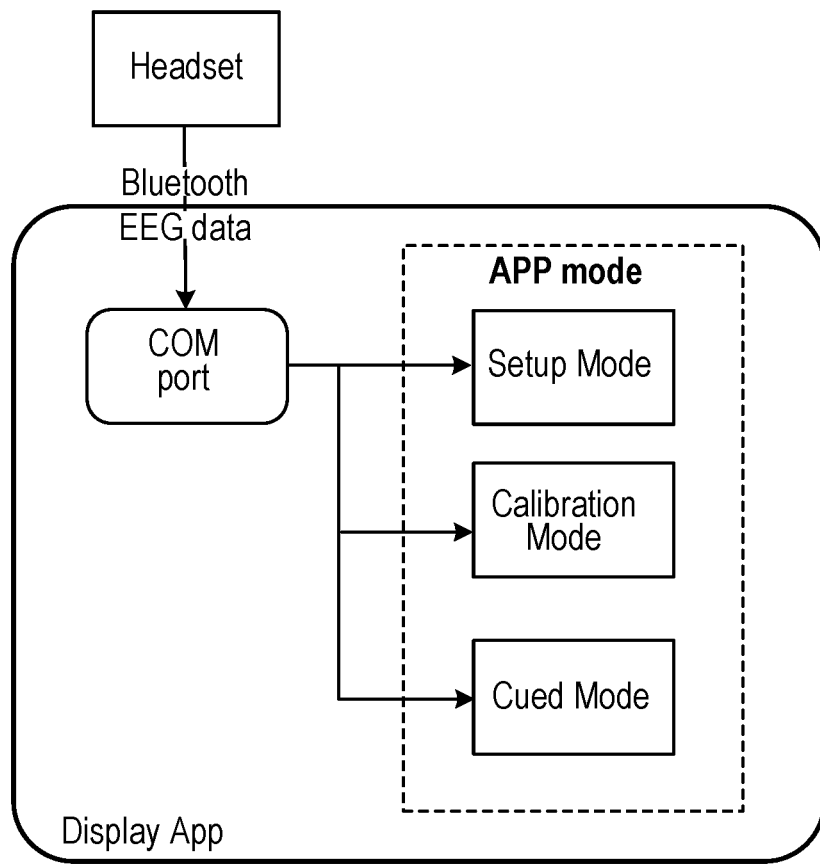

FIG. 8B illustrates that in some implementations of the therapy system 100 there may be three modes of operation in a therapy session, namely, a set-up mode, a calibration mode, and a cued mode. Each mode may handle different tasks.

For the set-up mode, the application program may use a set-up mode code sequence to check an EEG headset's sensors' contact at the beginning of a therapy session and after a user has put the headset on. In the set-up mode, all EEG data received from EEG headset may be sent to the orthosis device which may then determine the contact quality for each sensor as well as the EEG headset as a whole.

For the calibration mode, the application program may store EEG data and send that data to the orthosis device. The orthosis device may then compare data from "rest/relax"

cues against that from "imagining moving fingers" cues. These two sets of data may then be compared and stored to use later in a cued mode, and the results may be sent back to the application program on the tablet computer from the orthosis device for permanent storage.

For the cued mode, the application program may store EEG data and send it to the orthosis device. The orthosis device may then determine the patient's sustained intention to move and may send results back to the application program which may display the results in graphical form on the screen as well as storing the results in permanent storage.

Figure 8C:
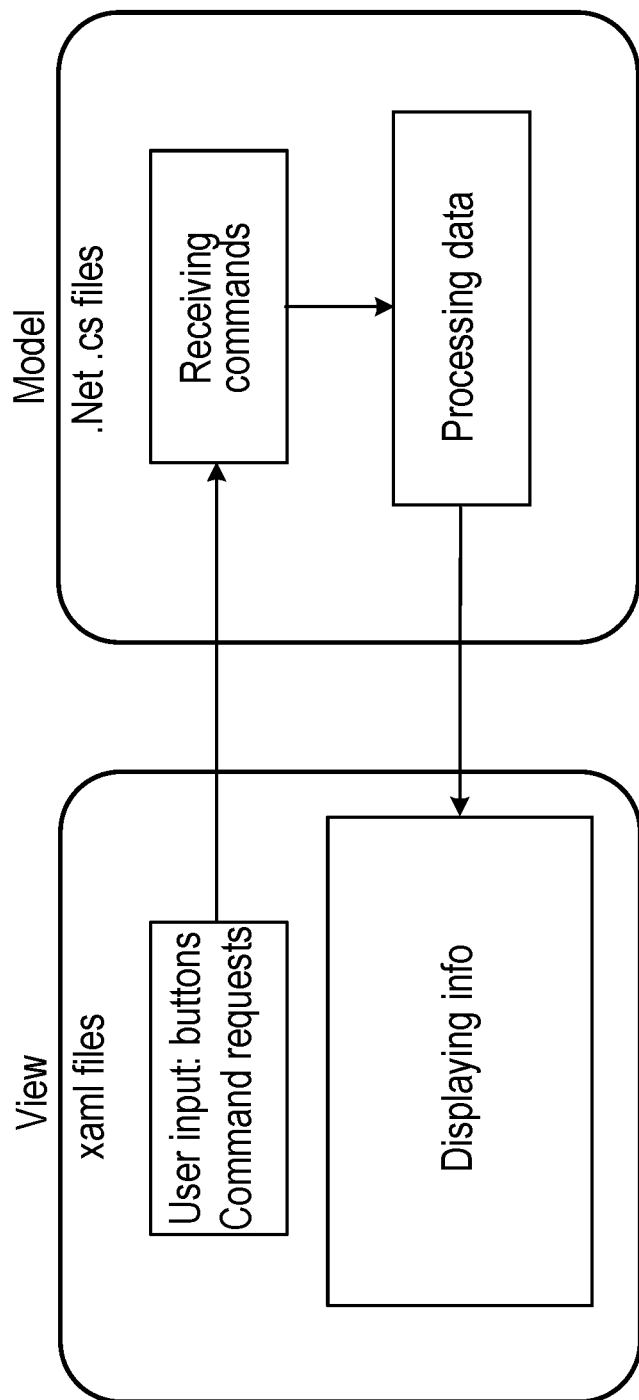

FIG. 8C illustrates that in one implementation the application program may have a structure of "view-model." The "view" may display therapy session info on the screen and get input from the user. The "model" may receive EEG data and results from the orthosis device, as illustrated in FIG. 8C.

In some implementations, screen snapshots that may be displayed during the course of using the rehabilitation system 100 of FIG. 1. The screen snapshots may be displayed, for example, on the display screen 112 of the tablet computing device 110, as an example, and may be generated by an application program being executed by the tablet computer 110.

For example, displays may be provided that show a tablet computer connecting automatically to the EEG headset and the orthosis device, and once a connection to the orthosis device is successful, the application program may display "connected" on the display device. Once a connection to the EEG headset is successful, and the received data is deemed to be good, the application program may cause a display of "EEG: Good" on the display device.

Additional displays on a display device may be provided that relate to a first-time set-up and may in some cases be shown only once per user. First regarding set-up of a EEG headset, there may be a contact check provided between EEG headset sensors and the user's head. The application program may record brain signal data from an EEG signal captured during certain specified cues to the subject and may send the recorded brain signal data to the orthosis device which may compare the data to determine the sensor contact quality and provide the results of a quality assessment.

In addition, screen displays may be provided that relate to initial screening. For example, before starting a therapy session, the application program may cause a screening to occur of the subject's brainwave data. This data may be used to determine the best brainwave frequency for the specific subject.

Also, screen displays may be provided on a display device that relate to patient set-up and may be shown once per user. Specifically, a display may be provided that guide input from a health care professional to input, for example, patient data for therapy sessions. An application program may use a tablet computer and its associated display to communicate this information to the orthosis device, and the orthosis device may save the information in its memory.

In addition, various screen displays may be provided to guide daily therapy using the orthosis device. For example, after first-time set-up and patient set-up have been performed, the application program may then facilitate daily therapy sessions. First there may be a set-up of the EEG headset. As such, at the beginning of each therapy session, the application program may confirm EEG headset sensor contact quality. Next, the application program may facilitate calibration of the system as part of the therapy session as illustrated for example in FIG. 3B (ref. 380). The application program may operate to calibrate the EEG headset to the user's brain signals for the current day in two steps: 1) reading brain signals while the user performs a specified action; and 2) reading brain signals while imagines performing a specified action. Comparison of these two sets of signals may be used in the rest of the therapy session.

Next, screen displays may be provided to facilitate a first daily exercise session to be performed. For example, the application program may execute to first provide a "start" screen and then use cause the collection of two data sets: 1) a recording of the user's brain signals while performing a specified action that is selected for use as a base brain wave; and 2) a recording of the user's brain signals while performing or imagining the performance of a specified signal that corresponds to a defined motor function. The application program may then cause the sending of the incoming brain signal data to the orthosis device, which then may determine from the signal whether the patient intends to perform the particular action that corresponds to the defined motor function, and if yes, the orthosis device may operate to assist the user in performing the defined motor function. The orthosis device may report this data back to the application program, which may graphically display the success of performing the defined motor function and may also store the data. There may be a specified number of daily therapy sessions, for example, five sessions. When finished with one session, the application program may operate to cause a display of results of that session to the user. Also, upon finishing all the therapy sessions for a day, an overall results display may be provided.

Figure 10:
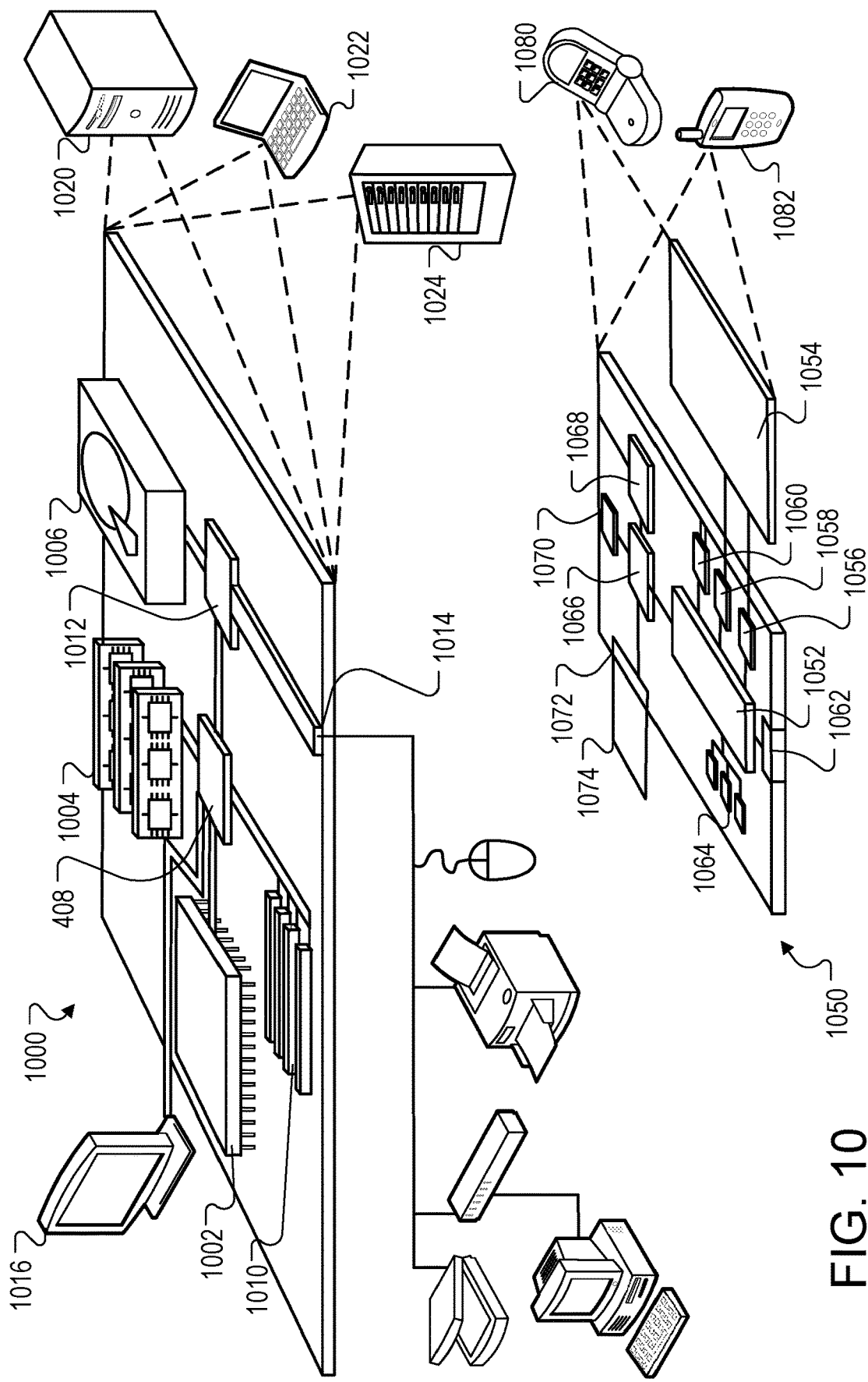
FIG. 10 shows an example computing device and mobile computing device that may be used in the methods and devices described in this specification.

FIG. 10 is a block diagram of computing devices 1000, 1050 that may be used to implement the systems and methods described in this document, as either a client or as a server or plurality of servers. Computing device 1000 is intended to represent various forms of digital computers, such as laptops, desktops, workstations, personal digital assistants, servers, blade servers, mainframes, and other appropriate computers. Computing device 1050 is intended to represent various forms of mobile devices, such as personal digital assistants, cellular telephones, smartphones, and other similar computing devices. Additionally, computing device 1000 or 1050 can include Universal Serial Bus (USB) flash drives. The USB flash drives may store operating systems and other applications. The USB flash drives can include input/output components, such as a wireless transmitter or USB connector that may be inserted into a USB port of another computing device. The components shown here, their connections and relationships, and their functions, are meant to be exemplary only, and are not meant to limit implementations described and/or claimed in this document.

Computing device 1000 includes a processor 1002, memory 1004, a storage device 1006, a high-speed interface 1008 connecting to memory 1004 and high-speed expansion ports 1010, and a low speed interface 1012 connecting to low speed bus 1014 and storage device 1006. Each of the components 1002, 1004, 1006, 1008, 1010, and 1012, are interconnected using various busses, and may be mounted on a common motherboard or in other manners as appropriate. The processor 1002 can process instructions for execution within the computing device 1000, including instructions stored in the memory 1004 or on the storage device 1006 to display graphical information for a GUI on an external input/output device, such as display 1016 coupled to high speed interface 1008. In other implementations, multiple processors and/or multiple buses may be used, as appropriate, along with multiple memories and types of memory. Also, multiple computing devices 1000 may be connected, with each device providing portions of the necessary operations (e.g., as a server bank, a group of blade servers, or a multi-processor system).

The memory 1004 stores information within the computing device 1000. In one implementation, the memory 1004 is a volatile memory unit or units. In another implementation, the memory 1004 is a non-volatile memory unit or units. The memory 1004 may also be another form of computer-readable medium, such as a magnetic or optical disk.

The storage device 1006 is capable of providing mass storage for the computing device 1000. In one implementation, the storage device 1006 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 1004, the storage device 1006, or memory on processor 1002.

The high-speed controller 1008 manages bandwidth-intensive operations for the computing device 1000, while the low speed controller 1012 manages lower bandwidth-intensive operations. Such allocation of functions is exemplary only. In one implementation, the high-speed controller 1008 is coupled to memory 1004, display 1016 (e.g., through a graphics processor or accelerator), and to high-speed expansion ports 1010, which may accept various expansion cards (not shown). In the implementation, low-speed controller 1012 is coupled to storage device 1006 and low-speed expansion port 1014. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 1000 may be implemented in a number of different forms, as shown in the figure. For example, it may be implemented as a standard server 1020, or multiple times in a group of such servers. It may also be implemented as part of a rack server system 1024. In addition, it may be implemented in a personal computer such as a laptop computer 1022. Alternatively, components from computing device 1000 may be combined with other components in a mobile device (not shown), such as device 1050. Each of such devices may contain one or more of computing device 1000, 1050, and an entire system may be made up of multiple computing devices 1000, 1050 communicating with each other.

Computing device 1050 includes a processor 1052, memory 1064, an input/output device such as a display 1054, a communication interface 1066, and a transceiver 1068, among other components. The device 1050 may also be provided with a storage device, such as a microdrive or other device, to provide additional storage. Each of the components 1050, 1052, 1064, 1054, 1066, and 1068, are interconnected using various buses, and several of the components may be mounted on a common motherboard or in other manners as appropriate.

The processor 1052 can execute instructions within the computing device 1050, including instructions stored in the memory 1064. The processor may be implemented as a chipset of chips that include separate and multiple analog and digital processors. Additionally, the processor may be implemented using any of a number of architectures. For example, the processor 1052 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 1050, such as control of user interfaces, applications run by device 1050, and wireless communication by device 1050.

Processor 1052 may communicate with a user through control interface 1058 and display interface 1056 coupled to a display 1054. The display 1054 may be, for example, a TFT (Thin-Film-Transistor Liquid Crystal Display) display or an OLED (Organic Light Emitting Diode) display, or other appropriate display technology. The display interface 1056 may comprise appropriate circuitry for driving the display 1054 to present graphical and other information to a user. The control interface 1058 may receive commands from a user and convert them for submission to the processor 1052. In addition, an external interface 1062 may be provide in communication with processor 1052, so as to enable near area communication of device 1050 with other devices. External interface 1062 may provide, for example, for wired communication in some implementations, or for wireless communication in other implementations, and multiple interfaces may also be used.

The memory 1064 stores information within the computing device 1050. The memory 1064 can be implemented as one or more of a computer-readable medium or media, a volatile memory unit or units, or a non-volatile memory unit or units. Expansion memory 1074 may also be provided and connected to device 1050 through expansion interface 1072, which may include, for example, a SIMM (Single In Line Memory Module) card interface. Such expansion memory 1074 may provide extra storage space for device 1050, or may also store applications or other information for device 1050. Specifically, expansion memory 1074 may include instructions to carry out or supplement the processes described above, and may include secure information also. Thus, for example, expansion memory 1074 may be provide as a security module for device 1050, and may be programmed with instructions that permit secure use of device 1050. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1064, expansion memory 1074, or memory on processor 1052 that may be received, for example, over transceiver 1068 or external interface 1062.

Device 1050 may communicate wirelessly through communication interface 1066, which may include digital signal processing circuitry where necessary. Communication interface 1066 may provide for communications under various modes or protocols, such as GSM voice calls, SMS, EMS, or MIMS messaging, CDMA, TDMA, PDC, WCDMA, CDMA2000, or GPRS, among others. Such communication may occur, for example, through radio-frequency transceiver 1068. In addition, short-range communication may occur, such as using a Bluetooth, WiFi, or other such transceiver (not shown). In addition, GPS (Global Positioning System) receiver module 1070 may provide additional navigation- and location-related wireless data to device 1050, which may be used as appropriate by applications running on device 1050.

Device 1050 may also communicate audibly using audio codec 1060, which may receive spoken information from a user and convert it to usable digital information. Audio codec 1060 may likewise generate audible sound for a user, such as through a speaker, e.g., in a handset of device 1050. Such sound may include sound from voice telephone calls, may include recorded sound (e.g., voice messages, music files, etc.) and may also include sound generated by applications operating on device 1050.

The computing device 1050 may be implemented in a number of different forms, as shown in the figure. For example, it may be implemented as a cellular telephone 1080. It may also be implemented as part of a smartphone 1082, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system may include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems.

Accordingly, other embodiments are within the scope of the following claims.

What is claimed is:

1. A system for moving or assisting in movement of a body part of a subject, comprising:
   a body part interface comprising a main housing structure configured to attach the body part interface to a forearm of the subject and a finger stay component configured to attach the body part interface to at least one finger of the subject;
   a motor-actuated assembly connected to the body part interface to move the body part interface to cause flexion and extension movement of the body part; and
   a force sensing module configured to measure forces applied between the body part interface and the motor-actuated assembly to ascertain at least one of volitional flexion and volitional extension movement of the body part by the subject;
   the force sensing module comprising a housing attached to the finger stay component, a force sensor support member attached to the motor-actuated assembly and pivotably connected to the housing, a first force sensor mounted on an upper surface of the force sensor support member and arranged to measure a volitional flexion movement force of the at least one finger when the housing pivots in relation to the force sensor support member in a first direction, and a second force sensor mounted on a lower surface of the force sensor support member opposite the upper surface and arranged to measure a volitional extension movement force of the at least one finger when the housing pivots in relation to the force sensor support member in a second direction that is opposite of the first direction.

2. The system of claim 1, wherein the force sensing module comprises at least one force sensing resistor.

3. The system of claim 1, wherein the force sensing module comprises at least one load cell force sensor.

4. The system of claim 2, wherein the motor-actuated assembly and the body part interface are pivotally connected such that the motor-actuated assembly and the body part interface are configured to pivot relative to each other such that the body part interface is configured to rotate in a first direction and a second direction opposite to the first direction.

5. The system of claim 4, wherein:
the motor-actuated assembly is configured to cause force to be applied to the first force sensor when the motor-actuated assembly rotates the body part interface in the first direction and to cause force to be applied to the second force sensor when the motor-actuated assembly rotates the body part interface in the second direction.

6. The system of claim 5, wherein the first force sensor on the upper surface is aligned with a downwardly facing structure provided on one of the motor-actuated assembly or the body part interface assembly that does not have the force sensor support member, wherein the first force sensor is applied against the downwardly facing structure when the motor-actuated assembly and the body part interface pivot relative to one another in the first direction.

7. The system of claim 6, wherein the second force sensor on the lower surface is aligned with an upwardly facing structure provided on the one of the motor-actuated assembly or the body part interface assembly that does not have the force sensor support member, wherein the second force sensor is applied against the upwardly facing structure when the motor-actuated assembly and the body part interface rock relative to one another in the second direction.

8. The system of claim 5, wherein the system is configured so that the first force sensor is used to detect when the motor-actuated assembly is operating to cause extension motion of the secured body part and the subject is providing little or no contribution to the extension motion.

9. The system of claim 5, wherein the system is configured so that the first force sensor is used to detect when the subject is volitionally causing flexion motion of the secured body part and the motor-actuated assembly is not operating to move or assist in the flexion motion.

10. The system of claim 5, wherein the system is configured so that the second force sensor is used to detect when the motor-actuated assembly is operating to cause flexion motion of the secured body part and the subject is providing little or no contribution to the flexion motion.

11. The system of claim 5, wherein the system is configured so that the second force sensor is used to detect when the subject is volitionally causing extension motion of the secured body part and the motor-actuated assembly is not operating to move or assist in the extension motion.

12. A rehabilitation system for a subject, comprising:
a brain signal acquisition device configured to collect brain signals from the subject; and
an orthosis system for moving or assisting in movement of a body part of the subject in response to the brain signals, comprising:
a body part interface comprising a main housing structure configured to attach the body part interface to a forearm of the subject and a finger stay component configured to attach the body part interface to at least one finger of the subject;
a motor-actuated assembly connected to the body part interface to move the body part interface to cause flexion and extension movement of the body part; and
a force sensing module configured to measure forces applied between the body part interface and the motor-actuated assembly to ascertain volitional flexion and extension movement of the body part by the subject;
the force sensing module comprising a housing attached to the finger stay component, a force sensor support member attached to the motor-actuated assembly and pivotably connected to the housing, a first force sensor mounted on an upper surface of the force sensor support member and arranged to measure a volitional flexion movement force of the at least one finger when the housing pivots in relation to the force sensor support member in a first direction, and a second force sensor mounted on a lower surface of the force sensor support member opposite the upper surface and arranged to measure a volitional extension movement force of the at least one finger when the housing pivots in relation to the force sensor support member in a second direction that is opposite of the first direction.

13. The rehabilitation system of claim 12, wherein the motor-actuated assembly and the body part interface are pivotally connected such that the motor-actuated assembly and the body part interface are configured to pivot relative to each other such that the body part interface is configured to rotate in a first direction and a second direction opposite to the first direction.

14. The rehabilitation system of claim 13, wherein:
the motor-actuated assembly is configured to cause force to be applied to the first force sensor when the motor-actuated assembly rotates the body part interface in the first direction and to cause force to be applied to the second force sensor when the motor-actuated assembly rotates the body part interface in the second direction.

15. The rehabilitation system of claim 14, wherein the first force sensor on the upper surface is aligned with a downwardly facing structure provided on one of the motor-actuated assembly or the body part interface assembly that does not have the force sensor support member, wherein the first force sensor is applied against the downwardly facing structure when the motor-actuated assembly and the body part interface pivot relative to one another in the first direction.

16. The rehabilitation system of claim 15, wherein the second force sensor on the lower surface is aligned with an upwardly facing structure provided on the one of the motor-actuated assembly or the body part interface assembly that does not have the force sensor support member, wherein the second force sensor is applied against the upwardly facing structure when the motor-actuated assembly and the body part interface rock relative to one another in the second direction.

17. The rehabilitation system of claim 14, wherein the rehabilitation system is configured so that the first force sensor is used to detect when the motor-actuated assembly is operating to cause extension motion of the secured body part and the subject is providing little or no contribution to the extension motion.

18. The rehabilitation system of claim 14, wherein the rehabilitation system is configured so that the first force sensor is used to detect when the subject is volitionally causing flexion motion of the secured body part and the motor-actuated assembly is not operating to move or assist in the flexion motion.

19. The rehabilitation system of claim 14, wherein the rehabilitation system is configured so that the second force sensor is used to detect when the motor-actuated assembly is operating to cause flexion motion of the secured body part and the subject is providing little or no contribution to the flexion motion.

20. The rehabilitation system of claim 14, wherein the rehabilitation system is configured so that the second force sensor is used to detect when the subject is volitionally causing extension motion of the secured body part and the motor-actuated assembly is not operating to move or assist in the extension motion.

21. The rehabilitation system of claim 12, wherein the force sensing module comprises at least one force sensing resistor.

22. The rehabilitation system of claim 12, wherein the force sensing module comprises at least one load cell force sensor.

* * * * *

UNITED STATES PATENT AND TRADEMARK OFFICE
CERTIFICATE OF CORRECTION

PATENT NO. : 11,690,774 B2
APPLICATION NO. : 17/069433
DATED : July 4, 2023
INVENTOR(S) : Kern Bhugra and August Anderson It is certified that error appears in the above-identified patent and that said Letters Patent is hereby corrected as shown below:

In the Claims

In Column 54, Line 61, in Claim 4, delete "Claim 2," and insert -- Claim 1, --.

Signed and Sealed this
Twenty-second Day of August, 2023

Katherine Kelly Vidal
*Director of the United States Patent and Trademark Office*